US010626186B2

(12) United States Patent
Lenting et al.

(10) Patent No.: US 10,626,186 B2
(45) Date of Patent: Apr. 21, 2020

(54) ANTI-VWF D'D3 SINGLE-DOMAIN ANTIBODIES AND METHODS OF USE

(71) Applicants: INSERM (INSTITUT NATIONAL DE LA SANTE ET DE LA RECHERCHE MEDICALE), Paris (FR); UNIVERSITE PARIS-SUD, Orsay (FR)

(72) Inventors: Petrus Lenting, Kremlin-Bicetre (FR); Gabriel Ayme, Le Kremlin Bicetre (FR); Cecile Denis, Le Kremlin-Bicetre (FR); Olivier Christophe, Le Kremlin-Bicetre (FR)

(73) Assignees: INSERM (Institut National de la Sante et de la Recherche Medicale), Paris (FR); Universite Paris-Saclay, Saint Aubin (FR)

( * ) Notice: Subject to any disclaimer, the term of this patent is extended or adjusted under 35 U.S.C. 154(b) by 0 days.

(21) Appl. No.: 16/072,784

(22) PCT Filed: Jan. 25, 2017

(86) PCT No.: PCT/EP2017/051569
§ 371 (c)(1),
(2) Date: Jul. 25, 2018

(87) PCT Pub. No.: WO2017/129630
PCT Pub. Date: Aug. 3, 2017

(65) Prior Publication Data
US 2019/0085096 A1    Mar. 21, 2019

(30) Foreign Application Priority Data

Jan. 26, 2016 (EP) .................................. 16305071

(51) Int. Cl.
| | | |
|---|---|---|
| *C07K 16/36* | (2006.01) |
| *C07K 14/755* | (2006.01) |
| *C07K 14/745* | (2006.01) |
| *A61P 7/04* | (2006.01) |
| *A61K 39/00* | (2006.01) |
| *C12N 15/62* | (2006.01) |

(52) U.S. Cl.
CPC .............. *C07K 16/36* (2013.01); *A61P 7/04* (2018.01); *C07K 14/745* (2013.01); *C07K 14/755* (2013.01); *C12N 15/62* (2013.01); *A61K 2039/505* (2013.01); *C07K 2317/33* (2013.01); *C07K 2317/565* (2013.01); *C07K 2317/569* (2013.01); *C07K 2317/92* (2013.01); *C07K 2317/94* (2013.01); *C07K 2319/31* (2013.01)

(58) Field of Classification Search
None
See application file for complete search history.

(56) References Cited

FOREIGN PATENT DOCUMENTS

| WO | 2004/062551 A2 | 7/2004 |
| WO | 2015/106052 A1 | 7/2015 |

OTHER PUBLICATIONS

Lloyd et al., Modelling the human immune response: performance of a 1011 human antibody repertoire against a broad panel of therapeutically relevant antigens. Protein Engineering, Design & Selection, 22,159-168, 2009. (Year: 2009).*
S. R. Madabhushi et al: "von Willebrand factor (VWF) propeptide binding to VWF D'D3 domain attenuates platelet activation and adhesion", Blood, vol. 119, No. 20, pp. 4769-4778, May 17, 2015.
I Tornai et al: "A monoclonal antibody recognizes a von Willebrand factor domain within the amino-terminal portion of the subunit that modulates the function of the glycoprotein IB- and IIB/IIIA-binding domains.", Journal of Clinical Investigation, vol. 91, No. 1, pp. 273-282, Jan. 1, 1993.
A. Yee et al: "A von Willebrand factor fragment containing the D'D3 domains is sufficient to stabilize coagulation factor VIII in mice", Blood, vol. 124, No. 3, pp. 445-452, May 21, 2014.
N. Shiltach et al: "Solution structure of the major factor VIII binding region on von Willebrand factor", Blood, vol. 123, No. 26, pp. 4143-4151, Jun. 26, 2014.
H. Ulrichts et al: "Shielding of the A1 Domain by the D'D3 Domains of von Willebrand Factor Modulates Its Interaction with Platelet Glycoprotein Ib-IX-V", Journal of Biological Chemistry, vol. 281, No. 8, pp. 4699-4707, Feb. 24, 2006.
Muyldermans S: "Single Domain Camel Antibodies: Current Status", Journal of Biotechnology, Elsevier Science Publishers, Amsterdam, NL, vol. 74, No. 4, pp. 277-302, Jan. 1, 2001.

* cited by examiner

*Primary Examiner* — Elly-Gerald Stoica
(74) *Attorney, Agent, or Firm* — W & C IP

(57) ABSTRACT

The invention relates to isolated single-domain antibodies (sdAb) directed against von Willebrand Factor (VWF) D'D3 domain and chimeric polypeptides comprising thereof such as blood clotting factors and their uses in therapy such as in the prevention and treatment of hemostatic disorders. The invention also rotates to a method of extending or increasing half-life of a therapeutic polypeptide comprising a step of adding to the polypeptide sequence of said therapeutic polypeptide at least one sdAb directed against VWF D'D3 domain.

Figure 1:
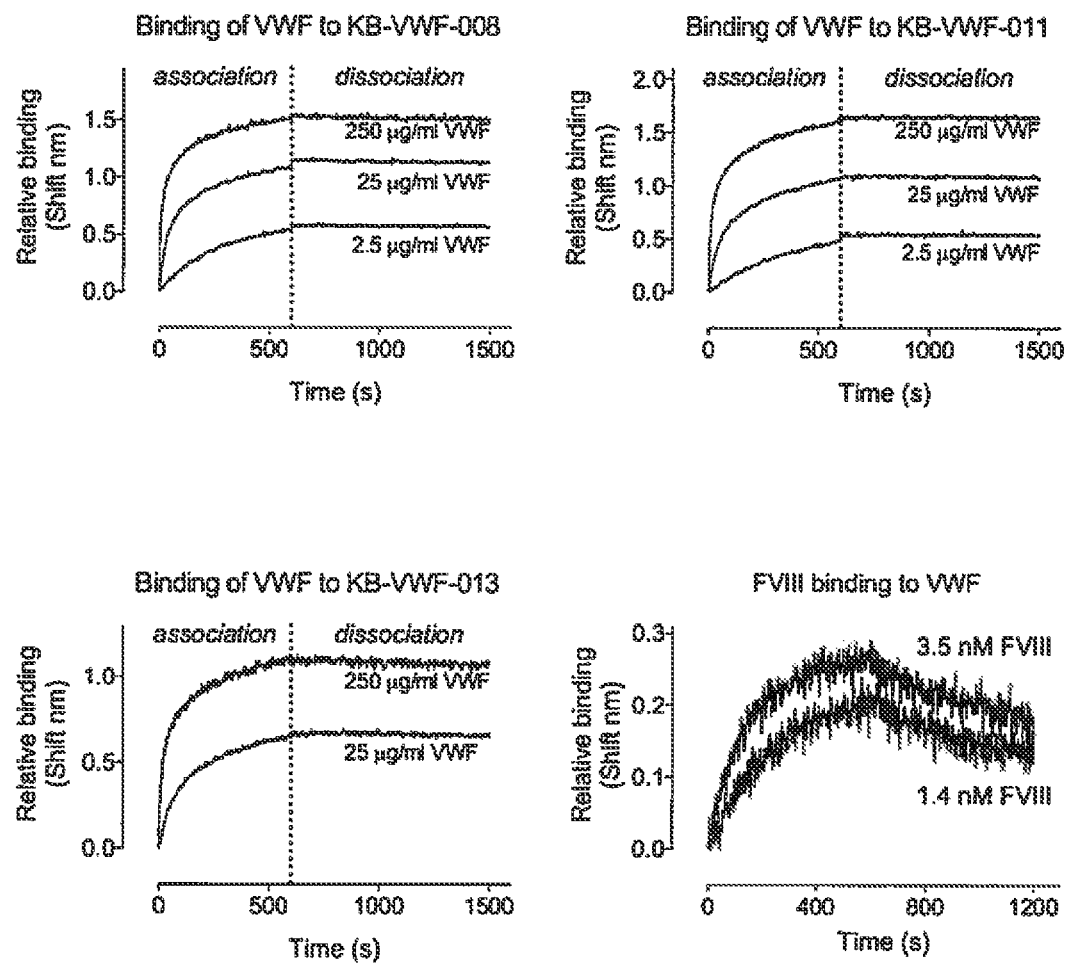

9 Claims, 5 Drawing Sheets
Specification includes a Sequence Listing.

ANTI-VWF D'D3 SINGLE-DOMAIN ANTIBODIES AND METHODS OF USE

FIELD OF THE INVENTION

The invention is in the field of immunotherapy. More particularly, the invention relates to isolated single-domain antibodies (sdAb) directed against von Willebrand Factor (VWF) D'D3 domain and polypeptides comprising thereof such as blood clotting factors and their uses in therapy such as in the prevention and treatment of hemostatic disorders.

BACKGROUND OF THE INVENTION

Extending in vim half-life of therapeutic proteins, thereby enhancing their efficiency is a major concern in the pharmaceutical field. Numerous strategies have been employed towards this end, including covalent modification, such as through PEGylation or Fc-Fusion proteins, which improves protein stability and solubility, prevents proteolytic degradation, and reduces the clearance rate from the bloodstream. Such approaches have been applied to different therapeutic proteins and for different disorders such as Haemophilia A which is a bleeding disorder caused by defects in the gene encoding coagulation factor VIII (FVIII) and affects 1-2 in 10,000 male births. Patients affected with hemophilia A can be treated with infusion of purified plasma-derived or recombinantly produced FVIII. All commercially available FVIII products, however, are known to have a short half-life of several hours (7-21 hours. Van Dijk et al Haematologica 2005 92:494-498), requiring frequent intravenous administration to the patients. Thus, a number of approaches have been tried in order to extend the FVIII half-life. For example, the approaches in development to extend the half-life of clotting factors include chemical (PEGylation)[1] or genetic modification (Fc-fusion)[2] of the FVIII molecule. Regardless of the protein engineering used, however, the long acting FVIII products currently under development are repotted to have limited half-lives—only to about 1-5 to 2 hours in preclinical animal models. Consistent results have been demonstrated in humans, for example, rFVIIIFc was reported to improve half-life up to 1.7 fold compared with ADVATE® in hemophilia A patients.

Due to the frequent dosing and inconvenience caused by the dosing schedule, there is still a need to develop FVIII products requiring less frequent administration, i.e., a FVIII product that has a half-life longer than the 1.5 to 2 fold half-life limitation.

SUMMARY OF THE INVENTION

The invention relates to isolated single-domain antibodies (sdAb) directed against von Willebrand Factor (VWF) D'D3 domain and polypeptides comprising thereof such as blood clotting factors and their uses in therapy such as in the prevention and treatment of hemostatic disorders. In particular, the present invention is defined by the claims.

DETAILED DESCRIPTION OF THE INVENTION

The invention relies on the discovery that introducing an isolated single-domain antibody (sdAb) directed against the von Willebrand factor (VWF) D'D3 domain into a therapeutic peptide leads to obtain a polypeptide with a half-life significantly increased. Indeed, the chimeric polypeptide according to the invention shows a reduced dissociation from VWF leading to more stable complex formation. This results in reduced clearance rates and thus an extended half-life. For instance, the inventors show that a chimeric FVIII polypeptide in which two isolated sdAb directed against VWF D'D3 domain (FVIII-KB013bv) are inserted thereby replacing the B-domain exhibits an extended half-life comparatively to wild-type B-domainless FVIII (T½ for wt-FVIII is 1.10 h (95% confidence interval: 0.88-1.48 h) and T½ for FVIII-KB-013bv is 2.11 h (95% CI: 1.66-2.92 h) when determined in haemophilic mice. Half-life extension is thus 2.11/1.10=1.9-fold. The sdAb directed against VWF D'D3 domain can also be used to induce complex formation with proteins that otherwise do not bind VWF. For example, a fusion protein FVII-KB013bv (consisting of FVII and two isolated sdAbs at the C-terminal end of FVII) but not FVII was found to form a complex with VWF. Furthermore, the inventors also demonstrated that such chimeric FVIII polypeptide may be complexed with VWF variants in order to improve even more its half-life (e.g. FVIII-KB013bv/D'D3-Fc). Thus, for the first time, inventors have demonstrated an increase of half-life with such construction.

Single-Domain Antibodies Directed Against VWF D'D3 Domain of the Invention

In a first aspect, the invention relates to an isolated single-domain antibody (sdAb) directed against von Willebrand Factor (VWF) D'D3 domain.

By "isolated" it is meant, when referring to a single-domain antibody according to the invention, that the indicated molecule is present in the substantial absence of other biological macromolecules of the same type.

As used herein the term "single-domain antibody" (sdAb) has its general meaning in the art and refers to the single heavy chain variable domain of antibodies of the type that can be found in Camelid mammals which are naturally devoid of light chains. Such single-domain antibody are also called VHH or "Nanobody®". For a general description of (single) domain antibodies, reference is also made to the prior art cited above, as well as to EP 0 368 684, Ward et al. (Nature 1989 Oct. 12: 341 (6242): 544-6). Holt et al. Trends Biotechnol, 2003, 21(11):484-490; and WO 06/030220, WO 06/003388. The amino acid sequence and structure of a single-domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementary Determining Region 1" or "CDR1"; as "Complementarity Determining Region 2" or "CDR2" and as "Complementarity Determining Region 3" or "CDR3", respectively. Accordingly, the single-domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single-domain antibody are numbered according to the general numbering for VH domains given by the International ImMunoGeneTics information system aminoacid numbering (http://imgt.cines.fr/).

The term "VWF" has its general meaning in the art and refers to the human von Willebrand factor (VWF) which is a blood glycoprotein involved in blood clotting. VWF is a monomer composed of several homologous domains each covering different functions: D1-D2-D'-D3-A1-A2-A3-D4-C1-C2-C3-C4-C5-C6-CK. The naturally occurring human VWF protein has an aminoacid sequence as shown in GeneBank Accession number NP_000543.2. Monomers are subsequently arranged into dimers or multimers by cross-linking of cysteine residues via disulfide bonds. Multimers of VWF can thus be extremely large and can consist of over 40 monomers also called high molecular weight (HMW)-multimers of VWF.

Preferably, the single-domain antibody directed against von VWF D'D3 domain does not induce the unfolding of VWF (which leads to exposure of platelet-binding sites). Moreover, within the context of the invention the single-domain antibody directed against von VWF D'D3 domain does not block the binding to VWF of a polypeptide such as a clotting factor comprising such single-domain antibody as described below.

The inventors have isolated a single-domain antibody (sdAb) KB-VWF-013 with the required properties and characterized the complementarity determining regions (CDRs) of said KB-VWF-013 and thus determined the CDRs of said sdAb (Table A):

TABLE A

Sequences of KB-VWF-013 domains.

| KB-VWF-013 domains | Sequences |
|---|---|
| CDR1 | SEQ ID NO: 1<br>GRTFIRYAMA |
| CDR2 | SEQ ID NO: 2<br>IPQSGGRSYYADSVKG |
| CDR3 | SEQ ID NO: 3<br>TSTYYGRSAYSSHSGGYDY |
| SEQUENCE KB-VWF-013 | SEQ ID NO: 4<br>QVQLVQSGGGLVQAGDSLRLSCAAS GRTFIRYAMA WFRQAPGKEREFVAA IPQSGGRSYYADSVKG RFTISRDNAKNTVYLQMNSLKPEDTAVYSCAA TSTYYGRSAYSSHSGGYDY WGQGTQVTVSS |

In particular, the invention relates to on isolated single-domain antibody (sdAb) comprising a CDR1 having at least 80$, preferably at least 90%, more preferably at least 95%, even more preferably at least 99% sequence identity with sequence set forth as SEQ ID NO: 1, a CDR2 having at least 80%, preferably at least 90%, more preferably at least 95%, even more preferably at least 99% sequence identity with sequence set forth as SEQ ID NO: 2 and a CDR3 having at least 80%, preferably at least 90%, more preferably at least 95%, even more preferably at least 99% sequence identity with sequence set forth as SEQ ID NO: 3.

Amino acid sequence identity is preferably determined using a suitable sequence alignment algorithm and default parameters, such as BLAST P (Karlin and Altschul, Proc. Natl Acad. Sci. USA 87(6):2264-2268 (1990)).

In some embodiments, the isolated single-domain antibody according to the invention comprises a CDR1 having a sequence set forth as SEQ ID NO: 1, a CDR2 having a sequence set forth as SEQ ID NO: 2 and a CDR3 having a sequence set forth as SEQ ID NO: 3.

In some embodiments, the isolated single-domain antibody according to the invention has the sequence set forth as SEQ ID NO: 4.

It should be further noted that the sdAb KB-VWF-013 cross-react with murine VWF, which is of interest for preclinical evaluation and toxicological studies.

Other examples of sdAb against VWF D'D3 that do not block FVIII binding (potential CDRs are indicated in bold):

TABLE B

Sequences of KB-VWF-008 domains.

| KB-VWF-008 domains | Sequences |
|---|---|
| CDR1 | SEQ ID NO: 5<br>GRTFSDYAMG |
| CDR2 | SEQ ID NO: 6<br>INRSGGRLSYAESVND |
| CDR3 | SEQ ID NO: 7<br>RTNWNPPRPLPEEYNY |
| SEQUENCE KB-VWF-008 | SEQ ID NO: 8<br>QVQLVQSGGGLVQAGDSLKLSCAASG RTFSDYAMG CIL QNPGKERDFVAS INRSGGRLSYAESVND LFTISVDNAK NMLYLQMNSLKPEDTAVHYCVL RTNWNPPRPLPEEYNY WGQETQVTVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO: 5, a CDR2 having at least 80%, preferably at least 90%, more preferably at least 95%, even more preferably at least 99% sequence identity with sequence set forth as SEQ ID NO: 6 and a CDR3 having at least 80%, preferably at least 90%, more preferably at least 95%, even more preferably at least 99% sequence identity with sequence set forth as SEQ ID NO: 7.

In some embodiments, the isolated single-domain antibody according to the invention comprises a CDR1 having a sequence set forth as SEQ ID NO: 5, a CDR2 having a sequence set forth as SEQ ID NO: 6 and a CDR3 having a sequence set forth as SEQ ID NO: 7.

In some embodiments, the isolated single-domain antibody according to the invention has the sequence set forth as SEQ ID NO: 8.

It should be further noted that the sdAb KB-VWF-008 cross-react with canine VWF, which is of interest for preclinical evaluation and toxicological studies.

TABLE C

Sequences of KB-VWF-011 domains.

| KB-VWF-011 domains | Sequences |
|---|---|
| CDR1 | SEQ ID NO: 9<br>GGTFSNYAMG |
| CDR2 | SEQ ID NO: 10<br>ISRSGHRTDYADSAKG |
| CDR3 | SEQ ID NO: 11<br>RSDWSIATTATSYDY |
| SEQUENCE KB-VWF-011 | SEQ ID NO: 12<br>QVQLVQSGGGLVQAGDSLRLSCAAS GGTFSNYAMG WF RQTPGKEREFVAR ISRSGHRTDYADSAKG RFTISRDN AKNTVYLQMNSLKPEDTAVYYCAA RSDWSIATTATSY DY WGQGTQVTVSS |

In particular, the invention relates to an isolated single-domain antibody (sdAb) comprising a CDR1 having at least 80%, preferably at least 90%, more preferably at least 95%, even more preferably at least 99% sequence identity with sequence set forth as SEQ ID NO. 9, a CDR2 having at least 80%, preferably at least 90%, more preferably at least 95%, even more preferably at least 99% sequence identity with sequence set forth as SEQ ID NO: 10 and a CDR3 having at least 80%, preferably at least 90%, more preferably at least 95%, even more preferably at least 99% sequence identity with sequence set forth as SEQ ID NO: 11.

In some embodiments, the isolated single-domain antibody according to the invention comprises a CDR1 having a sequence set forth as SEQ ID NO: 9, a CDR2 having a sequence set forth as SEQ ID NO: 10 and a CDR3 having a sequence set forth as SEQ ID NO: 11.

In some embodiments, the isolated single-domain antibody according to the invention has the sequence set forth as SEQ ID NO: 12.

In some embodiments, the single domain antibody is a "humanized" single-domain antibody. As used herein the term "humanized" refers to a single-domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favorable properties of single-domain antibodies of the invention. The one skilled in the art is able to determine and select suitable humanizing substitutions or suitable combinations of humanizing substitutions.

Chimeric Polypeptides of the Invention

A second aspect of the invention refers to a chimeric polypeptide comprising a polypeptide and at least one single-domain antibody directed against VWF of the invention.

As used herein, the terms "protein" or "polypeptide" refers to a polymer of two or more of the natural amino acids or non-natural amino acids.

A "fusion" or "chimeric" protein or polypeptide comprises a first amino acid sequence linked to a second amino acid sequence with which it is not naturally linked in nature. The amino acid sequences which normally exist in separate proteins can be brought together in the fusion polypeptide. A fusion protein is created, for example, by chemical synthesis, or by creating and translating a polynucleotide in which the polypeptide regions are encoded in the desired relationship. "Fusion" or "chimeric" polypeptides and proteins includes a combination of a first polypeptide chain, e.g., the FVIII protein, with a second polypeptide chain, e.g., a single-domain antibody directed against von VWF D'D3 domain.

In one embodiment, the chimeric polypeptide comprises any polypeptide, in particular therapeutic polypeptide, preferably having a short half-life leading to repealed administration to the patient in need thereof. Such therapeutic polypeptide may be for instance insulin, glucagon, osteoprotegerin (OPG), Angiopoietin-2 (ANGPT2) or furin.

In a particular embodiment, the chimeric polypeptide comprises a clotting factor (also referred as blood coagulation factor).

As used herein, the term "clotting factor," refers to molecules, or analogs thereof naturally occurring or recombinant produced which prevent or decrease the duration of a Weeding episode in a subject. In other words, it means molecules having pro-clotting activity, i.e., are responsible for the conversion of fibrinogen into a mesh of insoluble fibrin causing the blood to coagulate or dot. Clotting factors include factor VIII, prothrombin factors (comprising factor VU, Factor IX, factor X, protein C, protein S, protein Z and prothrombin) and clotting factor V. In a particular embodiment, the chimeric polypeptide according to the invention, wherein the polypeptide is a clotting factor selected from the group consisting of FVII, FVIII, protein C and protein S. Clotting factors of the invention may also be variants of wild-type clotting factors. The term "variants" includes insertions, deletions and substitutions, either conservative or non-conservative, where such changes do not substantially alter the active site, or active domain, which confers the biological activities of the respective clotting factor. Preferably a clotting factor is selected from the group consisting of FVII, FVIII and FX.

In one embodiment, the chimeric polypeptide comprising a polypeptide and at least one single-domain antibody directed against VWF according the invention, wherein said chimeric polypeptide has an increased affinity and/or a reduced dissociation rate constant for VWF comparatively to the wild-type polypeptide.

Without wishing to be bound by theory and knowing that affinity (i.e. affinity for VWF) is defined by Kd=association-rate $(k_{on})$/dissociation-rate $(k_{off})$, the chimeric polypeptide should have an increased affinity mainly due to a reduced $k_{off}$ as a result of the binding of the single-domain antibody directed against von VWF D'D3 domain to VWF.

In a preferred embodiment, the chimeric polypeptide exhibits a reduced clearance rate and thus an extended half-life when administered to a subject, compared to a corresponding polypeptide not linked to said sdAb directed against VWF and administered to said subject.

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid, a-phase and longer P-phase.

Typically, the chimeric polypeptide of the invention comprises at least one single-domain antibody of the invention, which is fused at the N terminal end, at the C terminal end, or both at the N terminal end and at the C terminal end of the therapeutic polypeptide, i.e. so as to provide a fusion protein (eventually via at least one further amino acid sequence).

Alternatively, the chimeric polypeptide of the invention comprises at least one single domain antibody of the invention, which is inserted into the therapeutic polypeptide.

The term "inserted into" as used herein refers to the position of a single-domain antibody directed against von VWF D'D3 domain in a chimeric polypeptide relative to the analogous position in native polypeptide such as mature human FVIII polypeptide. The term refers to the characteristics of the chimeric polypeptide relative to native polypeptide, and do not indicate, imply or infer any methods or process by which the chimeric polypeptide was made. For example, in reference to a chimeric polypeptide provided herein, the phrase "a single-domain antibody directed against von VWF D'D3 domain is inserted downstream of residue 759 of the FVIII polypeptide" means that the chimeric polypeptide comprises a sdAb directed against von VWF D'D3 domain downstream of an amino acid which corresponds to amino acid Arg759 in native human FVIII, e.g., bounded by amino acids corresponding to amino acids Ser760 or Phe761 of native human FVIII. Importantly, to improve exposure of the sdAb in the context of the fusion protein, flexible amino acid tinkers (e.g. one or multiple copies of the Gly-Gly-Gly-Ser motif) may be placed N- or C-terminally of each sdAb sequence.

As used herein, the term "insertion site" refers to a position in a polypeptide, such as a FVIII polypeptide, which is immediately upstream of the position at which a heterologous moiety can be inserted. An "insertion site" is specified as a number, the number being the number of the amino acid in said polypeptide to which the insertion site corresponds, which is immediately N-terminal to the position of the insertion.

According to the invention, the polypeptides that comprise a sole single-domain antibody are referred to herein as "monovalent" polypeptides. Polypeptides that comprise or essentially consist of two or more single-domain antibodies according to the invention are referred to herein as "multivalent" polypeptides.

The chimeric polypeptide according to the invention, comprises at least one single-domain antibody of the invention, wherein said single-domain antibody is fused at the N terminal end, at the C terminal end, both at the N terminal end and at the C terminal end of the therapeutic polypeptide or is inserted within the sequence of the therapeutic polypeptide.

In one embodiment, the polypeptide comprises two, three, four, five sdAb directed against VWF. In certain embodiments, two or more single-domain antibodies according to the invention are fused or inserted to the same terminal end or to the same insertion site.

In one embodiment, the polypeptide comprises at least one single-domain antibody of the invention and at least one other binding unit (i.e. directed against another epitope, antigen, target, protein or polypeptide), which is preferably also a single-domain antibody. Such a polypeptide is referred to herein as "multispecific" polypeptide: in opposition to a polypeptide comprising the same single-domain antibodies ("monospecific" polypeptide).

Thus, in some embodiments, the polypeptide of the invention may also provide at least one further binding site directed against any desired protein, polypeptide, antigen, antigenic determinant or epitope. Said binding site is directed against to the same protein, polypeptide, antigen, antigenic determinant or epitope for which the single domain antibody of the invention is directed again, or may be directed against a different protein, polypeptide, antigen, antigenic determinant or epitope) from the single domain antibody of the invention. A "bispecific" polypeptide of the invention is a polypeptide that comprises at least one single-domain antibody directed against a first antigen (e.g. VWF D'D3 domain) and at least one further binding site directed against a second antigen (i.e. different from VWF D'D3 domain).

In some embodiments, the further binding site is directed against a serum protein so that the half-lie of the single domain antibody is increased. Typically, said serum protein is albumin, to some embodiments, the polypeptides comprise a single domain antibody of the invention that is linked to an immunoglobulin domain. For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half-life on the single domain antibody.

In a particular embodiment, the dotting factor is FVIII. The terms "Factor VIII" and "FVIII" are used interchangeably herein. The FVIII protein is divided into 6 structural domains: a triplicated A domain (A1, A2, A3), a carbohydrate-rich and dispensable central domain (B-domain), and a duplicated C domain (C1, C2). In addition, the A1 and A2 domain, the A2 and B-domain and the B and A3 domain are separated by short sequences known as a1, a2 and a3, respectively, which are characterized by the presence of multiple acidic amino acids. The naturally occurring human FVIII protein has an amino acid sequence as shown in GeneBank Accession number NP_000123. "FVIII" includes wild type FVIII as well as variants of wild type FVIII having the procoagulant activity of wild type FVIII. Variants may have deletions, insertions and/or additions compared with the amino acid sequence of wild type FVIII such as mutants with reduced immunogenicity. The term FVIII includes proteolytically processed forms of FVIII. Commercially available therapeutic FVIII products include plasma derived FVIII (pdFVIII) and recombinant FVIII (rFVIII) products, such as the full-length rFVIII (Kogenate Bayer, Advate Baxter, Helixate CSL-Behring) and a B-domain deleted rFVIII (Refacto Wyeth, now marketed as Xyntha by Pfizer).

In certain embodiments, the polypeptide comprises a FVIII polypeptide and at least one sdAb directed against VWF according to the invention, wherein said FVIII polypeptide comprises A1 domain. A2 domain, A3 domain, C1 domain, C2 domain and optionally all or a portion of B domain, and wherein said at least one single-domain antibody directed against VWF is linked to said FVIII polypeptide at (i) the C-terminus of said FVIII polypeptide; (ii) within B domain of said FVIII polypeptide if all or a portion of B domain is present; (iii) within a surface loop of the A1 domain of said FVIII polypeptide; (iv) within a surface loop of the A2 domain of said FVIII polypeptide; (v) within a surface loop of the A3 domain of said FVIII polypeptide; (vi) within the C1 domain of said FVIII polypeptide; or (vii) within the C2 domain of said FVIII polypeptide; wherein said polypeptide exhibits a half-life that is extended when administered to a subject, compared to a corresponding FVIII not linked to said sdAb directed against von VWF and administered to said subject.

In one embodiment, the portion of B domain, is the portion with 1-20 amino acids of B domain (i.e. a portion comprising with the cleavage site of thrombin at position Arg740).

The typical half-life of a human FVIII in humans is several hours (7-21 hours. Van Dijk et al Haematologica 2005 92:494-498). In some embodiments, the chimeric FVIII polypeptide has extended half-life compared to wild type FVIII polypeptide. In certain embodiments, the half-life of the chimeric FVIII polypeptide is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII.

In a particular embodiment, two sdAb directed against VWF are inserted within the B domain of factor VIII (FVIII-KB13-bv) (SEQ ID NO: 13).

TABLE D

FVIII-KB-103-bv
A1 α1 A2 α2 KB-vwf-013 KB-vwf-013 α3 A3 C1 C2

| FVIII-KB13-bv | Sequence |
|---|---|
| Polypeptide | SEQ ID NO: 13 |

```
   1 M Q I E L S T C F F L C L L R F C F S A
  21 T R R Y Y L G A V E L S W D Y M Q S D L
  41 G E L P V D A R F P P R V P K S F P F N
  61 T S V V Y K K T L F V E F T D H L F N I
  81 A K P R P P W M G L L G P T I Q A E V Y
 101 D T V V I T L K N M A S H P V S L H A V
 121 G V S Y W K A S E G A E Y D D Q T S Q R
 141 E K E D D K V F P G G S H T Y V W Q V L
 161 K E N G P M A S D P L C L T Y S Y L D H
 181 V D L V K D L N S G L I G A L L V C R E
 201 G S L A K E K T Q T L H K F I L L F A V
 221 F D E G K S W H S E T K N S L M Q D R D
 241 A A S A R A W P K M H T V N G Y V N R S
 261 L P G L I G C H R K S V Y W H V I G M G
 281 T T P E V H S I F L E G H T F L V R N H
 301 R Q A S L E I S P I T F L T A Q T L L M
 321 D L G Q F L L F C H I S S H Q D G M E
 341 A Y V K V D S C P E E P Q L R M K N N E
 361 E A E D Y D D D L T D S E M D V V R F D
 381 D D N S P S F I Q I R S V A K K H P K T
 401 W V H Y I A A E E E D W D Y A P L V L A
 421 P D D R S Y K S Q Y L N N G P Q R I G R
 441 K Y K K V R F M A Y T D E T F K T R E A
 461 I Q H E S G I L G P L L Y G E V G D T L
 481 L I I F K N Q A S R P Y N I Y P H G I T
 501 D V R P L Y S R R L P K G V K H L K D F
 521 P I L P G E I F K Y K W T V T V E D G P
 541 T K S D P R C L T R Y Y S S F V N M E R
 561 D L A S G L I G P L L I C Y K E S V D Q
 581 E G N Q I M S D K R N V I L F S V F D E
 601 N R S W Y L T E N I Q R F L P N P A G V
 621 Q L E D P E F Q A S N I M H S I N G Y V
 641 F D S L Q L S V C L H E V A Y W Y I L S
 661 I G A Q T D F L S V F F S G Y T F K H K
 681 M V Y E D T L T L F P F S G E T V F M S
 701 M E N P G L W I L G C H N S D F R N R G
 721 M T A L L K V S S C D K N T G D Y Y E D
 741 S Y E D I S A Y L L S K N N A I E P R S
 761 F S G G G S Q V Q L V Q S G G G L V Q A
 781 G D S L R L S C A A S G R T F I R Y A M
 801 A W F R Q A P G K E R E F V A A I P Q S
 821 G G R S Y Y A D S V K G R F T I S R D N
 841 A K N T V Y L Q M N S L K P E D T A V Y
 861 S C A A T S T Y Y G R S A Y S S H S G G
 881 Y D Y W G Q G T Q V T V S S G G G S G G
 901 G S G G G S G G G S Q V Q L V Q S G G G
 921 L V Q A G D S L R L S C A A S G R T F I
 941 R Y A M A W F R Q A P G K E R E F V A A
 961 I P Q S G G R S Y Y A D S V K G R F T I
 981 S R D N A K N T V Y L Q M N S L K P E D
1001 T A V Y S C A A T S T Y Y G R S A Y S S
1021 H S G G Y D Y W G Q G T Q V T V S S G G
1041 G S E I T R T T L Q S D Q E E I D Y D D
1061 T I S V E M K K E D F D I Y D E D E N Q
1081 S P R S F Q K K T R H Y F I A A V E R L
1101 W D Y G M S S S P H V L R N R A Q S G S
1121 V P Q F K K V V F Q E F T D G S F T Q P
1141 L Y R G E L N E H L G L L G P Y I R A E
1161 V E D N I M V T F R N Q A S R P Y S F Y
1181 S S L I S Y E E D Q R Q G A E P R K N F
1201 V K P N E T K T Y F W K V Q H H M A P T
1221 K D E F D C K A W A Y F S D V D L E K D
1241 V H S G L I G P L L V C H T N T L N P A
1261 H G R Q V T V Q E F A L F F T I F D E T
1281 K S W Y F T E N M E R N C R A P C N I Q
1301 M E D P T F K E N Y R F H A I N G Y I M
1321 D T L P G L V M A Q D Q R I R W Y L L S
1341 M G S N E N I H S I H F S G H V F T V R
1361 K K E E Y K M A L Y N L Y P V V F E T V
1381 E M L P S K A G I W R V E C L I G E H L
1401 H A G M S T L F L V Y S N K C Q T P L G
1421 M A S G H I R D F Q I T A S G Q Y G Q W
1441 A P K L A R L H Y S G S I N A W S T K E
1461 P F S W I K V D L L A P H I I H G I K T
```

TABLE D-continued

FVIII-KB-103-bv
A1 α1 A2 α2 KB-vwf-013 KB-vwf-013 α3 A3 C1 C2

| FVIII-KB13-bv | Sequence |
|---|---|
| | 1481 Q G A R Q K F S S L Y I S Q F I I M Y S |
| | 1501 L D G K K W Q T Y R G N S T G T L M V F |
| | 1521 F G N V D S S G I K H N I F N P P I I A |
| | 1541 R Y I R L H P T H Y S I R S T L R M E W |
| | 1561 M G C D L N S C S M P L G M E S K A I S |
| | 1581 D A Q I T A S S Y F T N M F A T W S P S |
| | 1601 K A R L H L Q G R S N A W R P Q V N N P |
| | 1621 K E W L Q V D F Q K T M K V T G V T T Q |
| | 1641 G V K S L L T S M Y V K E F L I S S S Q |
| | 1661 D G H Q W T L F F Q N G K V K V F Q G N |
| | 1681 Q D S F T P V V N S L D P P L L T R Y L |
| | 1701 R I H P Q S W V H Q I A L R M E V L G C |
| | 1721 E A Q D L Y * |

Italic: signal peptide, not present in the protein that circulates in plasma
Underlined: flexible linkers connecting the various elements of the fusion protein
Bold: sequence of KB-VWF-013

In a particular embodiment, two sdAb directed against VWF are inserted within the B-domain of FVIII (FVIII_KB0013bv (6GGGS)) (SEQ ID NO: 16). Linker between sdAb sequence and FV1H light chain contains 6 GGGS-sequences instead of 1.

TABLE E

Sequences of FVIII-KB13-bv (6GGGS)

| FVIII_KB0013 bv(6GGGS) | Sequence |
|---|---|
| Polypeptide | SEQ ID NO: 16<br>MQIELSTCFFLCLLRFCFSATRRYYLGAVELSWDYMQ<br>SDLGELPVDARFPPRVPKSFPFNTSVVYKKTLFVEF<br>TDHLFNIAKPRPPWMGLLGPTIQAEVYDTVVITLKN<br>MASHPVSLHAVGVSYWKASEGAEYDDQTSQREKEDD<br>KVFPGGSHTYVWQVLKENGPMASDPLCLTYSYLSHV<br>DLVKDLNSGLIGALLVCREGSLAKEKTQTLHKFILL<br>FAVFDEGKSWHSETKNSLMQDRDAASARAWPKMHTV<br>NGYVNRSLPGLIGCHRKSVYWHVIGMGTTPEVHSIF<br>LEGHTFLVRNHRQASLEISPITFLTAQTLLMDLGQF<br>LLFCHISSHQHDGMEAYVKVDSCPEEPQLRMKNNEE<br>AEDYDDDLTDSEMDVVRFDDDNSPSFIQIRSVAKKH<br>PKTWVHYIAAEEEDWDYAPLVLAPDDRSYKSQYLNN<br>GPQRIGRKYKKVRFMAYTDETFKTREAIQHESGILG<br>PLLYGEVGDTLLIIFKNQASRPYNIYPHGITDVRPL<br>YSRRLPKGVKHLKDFPILPGEIFKYKWTVTVEDGPT<br>KSDPRCLTRYYSSFVNMERDLASGLIGPPLICYKES<br>VDQRGNQIMSDKRNVILFSVFDENRSWYLTENIQRF<br>LPNPAGVQLEDPEFQASNIMHSINGYVFDSLQLSVC<br>LHEVAYWYILSIGAQTDFLSVFFSGYTFKHKMVYED<br>TLTLFPFSGETVFMSMENPGLWILGCHNSDFRNRGM<br>TALLKVSSCDKNTGDYYEDSYEDISAYLLSKNNAIE<br>PRSF*SGGGS*QVQLVQSGGGLVQAGDSLRLSCAASGR<br>TFIRYAMAWFRQAPGKEREFVAAIPQSGGRSYYADS<br>VKGRFTISRDNAKNTVYLQMNSLKPEDTAVYSCAAT<br>STYYGRSAYSSHSGGYDYWGQGTQVTVSS*GGGSGGG*<br>*SGGGSGGGS*QVQLVQSGGGLVQAGDSLRLSCAASGR<br>TFIRYAMAWFRQAPGKEREFVAAIPQSGGRSYYADS<br>VKGRFTISRDNAKNTVYLQMNSLKPEDTAVYSCAAT<br>STYYGRSAYSSHSGGYDYWGQGTQVTVSS*GGGSGGG*<br>*SGGGSGGGSGGGSGGGS*EITRTTLQSDQEEIDYDDT<br>ISVEMKKEDFDIYDEDENQSPRSFQKKTRHYFIAAV<br>ERLWDYGMSSSPHVLRNRAQSGSVPQFKKVVFQEFT<br>DGSFTQPLYRGELNEHLGLLGPYIRAEVEDNIMVTF<br>RNQASRPYSFYSSLISYEEDQRQGAEPRKNFVKPNE<br>TKTYFWKVQHHMAPTKDEFDCKAWAYFSDVDLEKDV<br>HSGLIGPLLVCHTNTLNPAHGRQVTVQEFALFFTIF<br>DETKSWYFTENMERNCRAPCNIQMEDPTFKENYRFH<br>AINGYIMDTLPGLVMAQDQRIRWYLLSMGSNENIHS |

TABLE E-continued

Sequences of FVIII-KB13-bv (6GGGS)

| FVIII_KB0013 bv(6GGGS) | Sequence |
|---|---|
| | IHFSGHVFTVRKKEEYKMALYNLYPGVFETVEMLPS<br>KAGIWRVECLIGEHLHAGMSTFLFVYSNKCQTPLGM<br>ASHGHIRDFQITASGQYGQWAPKLARLHYSGSINAW<br>STKEPFSWIKVDLLAPMIIHGIKTQGARQKFSSLYI<br>SQFIIMYSLDGKKWQTYRGNSTGTLMVFFGNVDSSG<br>IKHNIFNPPIIARYIRLHPTHYSIRSTLRMEWMGCD<br>LNSCSMPLGMESKAISDAQITASSYFTNMFATWSPS<br>KARLHLQGRSNAWRPQVNNPKEWLQVDFQKTMKVTG<br>VTTQGVKSLLTSMYVKEFLISSSQDGHQWTLFFQNG<br>KVKVFQGNQDSFTPVVNSLDPPLLTRYLRIHPQSWV<br>HQIALRMEVLGCEAQDLY* |

Italic: GGGS-linker
Bold: sequence KB-VWF-013

In a particular embodiment, two sdAb directed against VWF are inserted within the B-domain of FVIII (FVIII_KB0013bv (6GGGS)_Y1680F) (SEQ ID NO: 17). Linker between sdAb sequence and FVIII light chain contains 6 GGGS-sequences instead of 1. The Y1680F mutation to avoid natural binding of FVIII to VWF (binding is only mediated by sdAb).

TABLE F

Sequences of FVIII_KB0013bv(6GGGS)_Y1680F

| FVIII_KB0013 bv(6GGGS)_Y1680F | Sequence |
|---|---|
| Polypeptide | SEQ ID NO: 17<br>MQIELSTCFFLCLLRFCFSATRRYLGAVELSW<br>DYMQSDLGELPVDARFPPRVPKSFPFNTSVVY<br>KKTLFVEFTDHLFNIAKPRPPWMGLLGPTIQA<br>EVYDTVVITLKNMASHPVSLHAVGVSYWKASE<br>GAEYDDQTSQREKEDDKVFPGGSHTYVWQVLK<br>ENGPMASDPLCLTYSYLSHVDLVKDLNSGLIG<br>ALLVCREGSLAKEKTQTLHKFILLFAVFDEGK<br>SWHSETKNSLMQDRDAASARAWPKMHTVNGYV<br>NRSLPGLIGCHRKSVYWHVIGMGTTPEVHSIF<br>LEGHTFLVRNHRQASLEISPITFLTAQTLLMD<br>LGQFLLFCHISSHQHDGMEAYVKVDSCPEEPQ<br>LRMKNNEEAEDYDDDLTDSEMDVVRFDDDNSP<br>SFIQIRSVAKKHPKTWVHYIAAEEEDWDYAPL<br>VLAPDDRSYKSQYLNNGPQRIGRKYKKVRFMA |

TABLE F-continued

Sequences of FVIII_KB0013bv(6GGGS)_Y1680F

FVIII_KB0013bv(6GGGS)_Y1680F  Sequence

YTDETFKTREAIQHESGILGPLLYGEVGDTLL
IIFKNQASRPYNIYPHGITDVRPLYSRRLPKG
VKHLKDFPILPGEIFKYKWTVTVEDGPTKSDP
RCLTRYYSSFVNMERDLASGLIGPLLICYKES
VDQRGNQIMSDKRNVILFSVFDENRSWYLTEN
IQRFLPNPAGVQLEDPEFQASNIMHSINGYVF
DSLQLSVCLHEVAYWYILSIGAQTDFLSVFFS
GYTFKHKMVYEDTLTLFPFSGETVFMSMENPG
LWILGCHNSDFRNRGMTALLKVSSCDKNTGDY
YEDSYEDISAYLLSKNNAIEPRSFS*GGGS*QVQ
LVQSGGGLVQAGDSLRLSCAASGRTFIRYAMA
WFRQAPGKEREFVAAIPQSGGRSYYADSVKGR
FTISRDNAKNTVYLQMNSLKPEDTAVYSCAAT
STYYGRSAYSSHSGGYDYWGQGTQVTVSS*GGG*
*SGGGSGGGSGGGS*QVQLVQSGGGLVQAGDSLR
LSCAASGRTFIRYAMAWFRQAPGKEREFVAAI
PQSGGRSYYADSVKGRFTISRDNAKNTVYLQM
NSLKPEDTAVYSCAATSTYYGRSAYSSHSGGY
DYWGQGTQVTVSS*GGGSGGGSGGGSGGGSGGG*
*GSGGGGSE*ITRTTLQSDQEEIDYDDTISVEMK
KEDFDI<u>F</u>DEDENQSPRSFQKKTRHYFIAAVER
LWDYGMSSSPHVLRNRAQSGSVPQFKKVVFQE
FTDGSFTQPLYRGELNEHLGLLGPYIRAEVED
NIMVTFRNQASRPYSFYSSLISYEEDQRQGAE
PRKNFVKPNETKTYFWKVQHHMAPTKDEFDCK
AWAYFSDVDLEKDVHSGLIGPLLVCHTNTLNP
AHGRQVTVQEFALFFTIFDETKSWYFTENMER
NCRAPCNIQMEDPTFKENYRFHAINGYIMDTL
PGLVMAQDQRIRWYLLSMGSNENIHSIHFSGH
VFTVRKKEEYKMALYNLYPGVFETVEMLPSKA
GIWRVECLIGEHLHAGMSTLFLVYSNKCQTPL
GMASGHIRDFQITASGQYGQWAPKLARLHYSG
SINAWSTKEPFSWIKVDLLAPMIIHGIKTQGA
RQKFSSLYISQFIIMYSLDGKKWQTYRGNSTG
TLMVFFGNVDSSGIKHNIFNPPIIARYIRLHP
THYSIRSTLRMEWMGCDLNSCSMPLGMESKAI
SDAQITASSYFTNMFATWSPSKARLHLQGRSN
AWRPQVVNNPKEWLQVDFQKTMKVTGVTTQGVK
SLLTSMYVKEFLISSSQDGHQWTLFFQNGKVK
VFQGNQDSFTPVVNSLDPPLLTRYLRIHPQSW
VHQIALRMEVLGCEAQDLY*

Italic: GGGS-linker
Bold: sequence KB-VWF-013
Bold underline: mutation p.Y1680F

In a particular embodiment, two sdAb directed against VWF are inserted at C terminus of FVIII (FVIII_BD_Cter-0013bv) (SEQ ID NO. 18).

TABLE G

Sequences of FVIII_BD_Cter-0013bv

FVIII_BD_Cter-0013bv  Sequence

Polypeptide  SEQ ID NO: 18
MQIELSTCFFLCLLRFCFSATRRYYLGAVELSWDY
MQSDLGELPVDARFPPRVPKSFPFNTSVVYKKTLF
VEFTDHLFNIAKPRPPWMGLLGPTIQAEVYDTVVI
TLKNMASHPVSLHAVGVSYWKASEGAEYDDQTSQR
EKEDDKVFPGGSHTYVWQVLKENGPMASDPLCLTY
SYSHVDLVKDLNSGLIGALLVCREGSLAKEKTQTL
HKFILLFAVFDEGKSWHSETKNSLMQDRDAASARA
WPKMHTVNGYVNRSLPGLIGCHRKSVYWHVIGMGT
TPEVHSIFLEGHTFLVRNHRQASLEISPITFLTAQ
TLLMDLGQFLLFCHISSHQHDGMEAYVKVDSCPEE
PQLRMKNNEEAEDYDDDLTDSEMDVVRFDDDNSPS
FIQIRSVAKKHPKTWVHYIAAEEEDWDYAPLVLAP
DDRSYKSQYLNNGPQRIGRKYKKVRFMAYTDETFK
TREAIQHESGILGPLLYGEVGDTLLIIFKNQASRP
YNIYPHGITDVRPLYSRRLPKGVKHLKDFPILPGE
IFKYKWTVTVEDGPTKSDPRCLTRYYSSFVNMERD

TABLE G-continued

Sequences of FVIII_BD_Cter-0013bv

FVIII_BD_Cter-0013bv  Sequence

LASGLIGPLLICYKESVDQRGNQIMSDKRNVILFS
VFDENRSWYLTENIQRFLPNPAGVQLEDPEFQASN
IMHSINGYVFDSLQLSVCLHEVAYWYILSIGAQTD
FLSVFFSGYTFKHKMVYEDTLTLFPFSGETVFMSM
ENPGLWILGCHNSDFRNRGMTALLKVSSCDKNTGD
YYEDSYEDISAYLLSKNNAIEPRSFSQNPPVLKRH
QREITRTTLQSDQEEIDYDDTISVEMKKEDFDIYD
EDENQSPRSFQKKTRHYFIAAVERLWDYGMSSSPH
VLRNRAQSGSVPQFKKVVFQEFTDGSFTQPLYRGE
LNEHLGLLGPYIRAEVEDNIMVTFRNQASRPYSFY
SSLISYEEDQRQGAEPRKNFVKPNETKTYFWKVQH
HMAPTKDEFDCKAWAYFSFVFLEKDVHSGLIGPLL
VCHTNTLNPAHGRQVTVQEFALFFTIFDETKSWYF
TENMERNCRAPCNIQMEDPTFKENYRFHAINGYIM
DTLPFLVMAQDQRIRWYLLSMGSNENIHFSGHVFT
VRKKEEYKMALYNLPGVFETVEMLPSKAGIWRVE
CLIGEHLHAGMSTLFLVYSNKCQTPLGMASGHIRD
FQITASGQYGQWAPKLARLHYSGSINAWSTKEPFS
WIKVDLLAPMIIHGIKTQGARQKFSSLYISQFIIM
YSLDGKKWQTYRGNSTGTLMVFFGNVDSSGIKHNI
FNPPIIARYIRLHPTHYSIRSTLRMEWMGCDLNSC
SMPLGMESKAISDAQITASSYFTNMFATWSPSKAR
LHLQGRSNAWRPQVVNNPKEWLQVDFQKTMKVTGVT
TQGVKSLLTSMYVKEFLISSSQDGHQTLFFQNGK
VKVFQGNQDSFTPVVNSLDPPLLTRYLRIHPQSWV
HQIALRMEVLGCEAQDLY<u>LTRPGVRL</u>*GGGSGGGSG*
*GGSGGGS*QVQLVQSGGGLVQAGDSLRLSCAASGRT
FIRYAMAWFRQAPGKEREFVAAIPQSGGRSYYADS
VKGRFTISRDNAKNTVYLQMNSLKPEDTAVYSCAA
TSTYYGRSAYSSHSGGYDYWGQGTQVTVSS*GGGSG*
*GGSGGGSGGGS*
QVQLVQSGGGLVQAGDSLRLSCAAS
GRTFIRYAMAWFRQAPGKEREFVAA
IPQSGGRSYYA
DSVKGRFTISRDNAKNTVYLQMNSL
KPEDTAVYSCA
ATSTYYGRSAYSSHSGGYDYWGQGTQVTVSS*

Italic: GGGS-linker
Bold: sequence KB-VWF-013
Underline: thrombin-cleavage site

In a particular embodiment, two sdAb directed against VWF are inserted at C terminus of FVIII (FVIII_BD_Cter-0013bv_Y1680F) (SEQ ID NO: 19). The Y1680F mutation to avoid natural binding of FVIII to VWF (binding is only mediated by sdAb).

TABLE H

Sequences of FVIII-BD-Cter-0013bv_Y1680F

FVIII_BD_Cter-0013bv_Y1680F  Sequence

Polypeptide  SEQ ID NO: 19
MQIELSTCFFLCLLRFCFSATRRYYLGAVELSWD
YMQSDLGELPVDARFPPRVPKSFPFNTSVVYKKT
LFVEFTDHLFNIAKPRPPWMGLLGPTIQAEVYDT
VVITLKNMASHPVSLHAVGVSYWKASEGAEYDDQ
TSQREKEDDKVFPGGSHTYVWQVLKENGPMASDP
LCLTYSYLSHVDLVKDLNSGLIGALLVCREGSLA
KEKTQTLHKFILLFAVFDEGKSWHSETKNSLMQD
RDAASARAWPKMHTVNGYVNRSLPGLIGCHRKSV
YWHVIGMGTTPEVHSIFLEGHTFLVRNHRQASLE
ISPITFLTAQTLLMDLGQFLLFCHISSHQHDGME
AYVKVDSCPEEPQLRMKNNEEAEDYDDDLTDSEM
DVVRFDDDNSPSFIQIRSVAKKHPKTWVHYIAAE
EEDWDYAPLVLAPDDRSYKSQYLNNGPQRIGRKY
KKVRFMAYTDETFKTREAIQHESGILGPLLYGEV
GDTLLIIFKNQASRPYNIYPHGITDVRPLYSRRL
PKGVKHLKDFPILPGEIFKYKWTVTVEDGPTKSD
PRCLTRYYSSFVNMERDLASGLIGPLLICYKESV

TABLE H-continued

Sequences of FVIII-BD-Cter-0013bv_Y1680F

| FVIII_BD_Cter-0013bv_Y1680F | Sequence |
|---|---|
| | DQRGNQIMSDKRNVILFSVFDENRSWYLTENIQR<br>FLPNPAGVQLEDPEFQASNIMHSINGYVFDSLQL<br>SVCLHEAVYWYILISGAQTDFLSVFFSGYTFKHK<br>MVYEDTLTLFPFSGETVFMSMENPGLWILGCHNS<br>DFRNRGMTALLKVSSCDKNTGDYYEDSYEDISAY<br>LLSKNNAIEPRSFSQNPPVLKRHQREITRTTLQS<br>DQEEIDYDDTISVEMKKEDFDIFDEDENQSPRSF<br>QKKTRHYFIAAVERLWDYGMSSSPHVLRNRAQSG<br>SVPQFKKVVFQEFTDGSFTQPLYRGELNEHLGLL<br>GPYIRAEVEDNIMVTFRNQASRPYSFYSSLISYE<br>EDQRQGAEPRKNFVKPNETKTYFWKVQHHMAPTK<br>DEFDCKAWAYFSDVDLEKDVHSGLIGPLLVCHTN<br>TLNPAHGRQVTVQEFALFFTIFDETKSWYFTENM<br>ERNCRAPCNIQMEDPTFKENYRFHAINGYIMDTL<br>PGLVMAQDQRIRWYLLSMGSNENIHSIHFSGHVF<br>RVRKKEEYKMALYNLYPGVFETVEMLPSKAGIWR<br>VECLIGEHLHAGMSTLFLVYSNKCQTPLGMASGH<br>IRDFQITASGQYGQWAPKLARLHYSGSINAWSTK<br>EPFSWIKVDLLAPMIIHGIKTQGARQKFSSLYIS<br>QFIIMYSLDGKKWQTYRGNSTGTLMVFFGNVDSS<br>GIKHNIFNPPIIARYIRLHPTHYSIRSTLRMEWM<br>GCDLNSCSMPLGMESKAISDAQITASSYPTNMFA<br>TWSPSKARLHLQGRSNAWRPQVNNPKEWLQVDFQ<br>KTMKVTGVTTQGVKSLLTSMYVKEFLISSSQDGH<br>QWTLFFQNGKVKVFQGNQDSFTPVVNSLDPPLLT<br>RYLRIHPQSWVHQIALRMEVLGCEAQDLY*LTPRG*<br>*RLGGGSGGGSGGGSGGGSQVQLVQSGGGLVQAGD<br>SLRLSCAASGRTFIRYAMAWFRQAPGKEREFVAA<br>IPQSGGRSYYADSVKGRFTISRDNAKNTVYLQMN<br>SLKPEDTAVYSCAATSTYYGRSAYSSHSGGYDYW<br>GQGTQVTVSS*GGGSGGGSGGGSGGGS*QVQLVQSG<br>GGLVQAGDSLRLSCAASGRTFIRYAMAWFRQAPG<br>KEREFVAAIPQSGGRSYYADSVKGRFTISRDNAK<br>NTVYLQMNSLKPEDTAVYSCAATSTYYGRSAYSS<br>HSGGYDYWGQGTQVTVSS*** |

Italic: GGGS-linker
Bold: sequence KB-VWF-013
Underline: thrombin-cleavage site
Bold underline: mutation p.Y1680F In a particular embodiment, two sdAb directed against VWF are inserted within the B-domain of FVIII, while two sdAb are inserted at the C-terminus (FVIII_KB0013bv_Cter-0013bv) (SEQ ID NO: 20).

TABLE I

Sequences of FVIII-KB0013bv_Cter-0013bv

| FVIII_KB0013bv_Cter-0013bv | Sequence |
|---|---|
| Polypeptide | SEQ ID NO: 20<br>MQIELSTCFFLCLLRFCFSATRRYYLGAVELSW<br>DYMQSDLGELPVDARFPPRVPKSFPFNTSVVYK<br>KTLFVEFTDHLFNIAKPRPPWMGLLGPTIQAEV<br>YDTVVITLKNMASHPVSLHAVGVSYWKASEGAE<br>YDDQTSQREKEDDKVFPGGSHTYVWQVLKENGP<br>MASDPLCLTYSYLSHVDLVKDLNSGLIGALLVC<br>REGSLAKEKTQTLHKFILLFAVFDEGKSWHSET<br>KNSLMQDRDAASARAWPKMHTVNGYVNRSLPGL<br>IGCHRKSVYWHVIGMGTTPEVHSIFLEGHTFLV<br>RNHRQASLEISPITFLTAQTLLMDLGQFLLFCH<br>ISSHQHDGMEAYVKVDSCPEEPQLRMKNNEEAE<br>DYDDDLTDSEMDVVRFDDDNSPSFIQIRSVAKK<br>KPKTWVHYIAAEEEDWDYAPLVLAPDDRSYKSQ<br>YLNNGPQRIGRKYKKVRFMAYTDETFKTREAIQ<br>HESGILGPLLYGEVGDTLLIIFKNQASRPYNIY<br>PHGITDVRPLYSRRLPKGVKHLKDFPILPGEIF<br>KYKWTVTVEDGPTKSDPRCLTRYYSSFVNMERD<br>LASGLIGPLLICYKESVDQRGNQIMSDKRNVIL<br>FSVFDENRSWYLTENIQRFLPNPAGVQLEDPEF<br>QASNIMHSINGYVFDSLQLSVCLHEVAYWYILS |

TABLE I-continued

Sequences of FVIII-KB0013bv_Cter-0013bv

| FVIII_KB0013bv_Cter-0013bv | Sequence |
|---|---|
| | IGAQTDFLSVFFSGYTFKHKMVYEDTLTLFPFS<br>GETVFMSMENPGLWILGCHNSDFRNRGMTALLK<br>VSSCDKNTGDYYEDSYEDISAYLLSKNNAIEPR<br>SFS*GGGS*QVQLVQSGGGLVQAGDSLRLSCAASG<br>RTFIRYAMAWFRQAPGKEREFVAAIPQSGGRSY<br>YADSVKGRFTISRDNAKNTVYLQMNSLKPEDTA<br>VYSCAATSTYYGRSAYSSHSGGYDYWGQGTQVT<br>VSS*GGGSGGGSGGGSGGGS*QVQLVQSGGGLVQA<br>GDSLRLSCAASGRTFIRYAMAWFRQAPGKEREF<br>VAAIPQSGGRSYYADSVKGRFTISRDNAKNTVY<br>LQMNSLKPEDTAVYSCAATSTYYGRSAYSSHSG<br>GYDYWGQGTQVTVSS*GGGS***EITRTTLQSDQEEI<br>DYDDTISVEMKKEDFDIYDEDENQSPRSFQKKT<br>RHYFIAAVERLWDYGMSSSPHVLRNRAQSGSVP<br>QFKKVVFQEFTDGSFTQPLYRGELNEHLGLLGP<br>YIRAEVEDNIMVTFRNQASRPYSFYSSLISYEE<br>DQRQGAEPRKNFVKPNETKTYFWKVQHHMAPTK<br>DEFDCKAWAYFSDVDLEKDVHSGLIGPLLVCHT<br>NTLNPAHGRQVTVQEFALFFTIFDETKSWYFTE<br>NMERNCRAPCNIQMEDPTFKENYRFHAINGYIM<br>DTLPGLVMAQDQRIRWYLLSMGSNENIHSIHFS<br>GHVFTVRKKEEYKMALYNLYPGVFETVEMLPSK<br>AGIWRVECLIGEHLHAGMSTLFLVYSNKCQTPL<br>GMASGHIRDFQITASGQYGQWAPKLARLHYSGS<br>INAWSTKEPFSWIKVDLLAPMIIHGIKTQGARQ<br>KFSSLYISQFIIMYSLDGKKWQTYRGNSTGTLM<br>VFFGNVDSSGIKHNIFNPPIIARYIRLHPTHYS<br>IRSTLRMEWMGCDLNSCSMPLGMESKAISDAQI<br>TASSYFTNMFATWSPSKARLHLQGRSNAWRPQV<br>NNPKEWLQVDFQKTMKVTGVTTQGVKSLLTSMY<br>VKEFLISSSQDGHQWTLFFQNGKVKVFQGNQDS<br>FTPVVNSLDPPLLTRYLRIHPQSWVHQIALRME<br>VLGCEAQDLY*LTPRGVRLGGGSGGGSGGGSGGG*<br>*S*QVQLVQSGGGLVQAGDSLRLSCAASGRTFIRY<br>AMAWFRQAPGKEREFVAAIPQSGGRSYYADSVK<br>GRFTISRDNAKNTVYLQMNSLKPEDTAVYSCAA<br>TSTYYGRSAYSSHSGGYDYWGQGTQVTVSS*GGG*<br>*SGGGSGGGSGGGS*QVQLVQSGGGLVQAGDSLRL<br>SCAASGRTFIRYAMAWFRQAPGKEREFVAAIPQ<br>SGGRSYYADSVKGRFTISRDNAKNTVYLQMNSL<br>KPEDTAVYSCAATSTYYGRSAYSSHSGGYDYWG<br>QGTQVTVSS* |

Italic: GGGS-linker
Bold: sequence KB-VWF-013
Underline: thrombin-cleavage site

In a particular embodiment, two sdAb directed against VWF are inserted within the B-domain of FVIII, while two sdAb are inserted at the C-terminus (FVIII_KB0013bv_Cter-0013bv_Y1680F) (SEQ ID NO: 21). The Y1680F mutation allows to avoid natural binding of FVIII to VWF (binding is only mediated by sdAb). C-terminal thrombin cleavage site allows to release sdAb upon FVIII activation.

TABLE J

Sequences of FVIII_KB0013bv_Cter-0013bv_Y1680F

| FVIII_KB0013bv_Cter-0013bv_Y1680F | Sequence |
|---|---|
| Polypeptide | SEQ ID NO: 21<br>MQIELSTCFFLCLLRFCFSATRRYYLGAVE<br>LSWDYMQSDLGELPVDARFPPRVPKSFPFN<br>TSVVYKKTLFVEFTDHLFNIAKPRPPWMGL<br>LGPTIQAEVYDTVVITLKNMASHPVSLHAV<br>GVSYWKASEGAEYDDQTSQREKEDDKVFPG<br>GSHTYVWQVLKENGPMASDPLCLTYSYLSH<br>VDLVKDLNSGLIGALLVCREGSLAKEKTQT<br>LHKFILLFAVFDEGKSWHSETKNSLMQDRD<br>AASARAWPKMHTVNGYVNRSLPGLIGCHRK |

TABLE J-continued

Sequences of FVIII_KB0013bv_Cter-0013bv_Y1680F

FVIII_KB0013bv_Cter-0013bv_Y1680F    Sequence

SVYWHVIGMGTTPEVHSIFLEGHTFLVRNH
RQASLEISPITFLTAQTLLMDLGQFLLFCH
ISSHQHDDGMEAYVKVDSCPEEPQLRMKNNE
EAEDYDDDLTDSEMDVVRFDDDNSPSFIQI
RSVAKKHPKTWVHYIAAEEEDWDYAPLVLA
PDDRSYKSQYLNNGPQRIGRKYKKVRFMAY
TDETFKTREAIQHESGILGPLLYGEVGDTL
LIIFKNQASRPYNIYPHGITDVRPLYSRRL
PKGVKHLKDFPILPGEIFKYKWTVTVEDGP
TKSDPRCLTRYYSSFVNMERDLASGLIGPL
LICYKESVDQRGNQIMSDKRNVILFSVFDE
NRSWYLTENIQRFLPNPAGVQLEDPEFQAS
NIMHSINGYVFDSLQLSVCLHEVAYWYILS
IGAQTDFLSVFFSGYTFKHKMVYEDTLTLF
PFSGETVFMSMENPGLWILGCHNSDFRNRG
MTALLKVSSCDKNTGDYYEDSYEDISAYLL
SKNNAIEPRSFS*GGGS*QVQLVQSGGGLVQA
GDSLRLSCAASGRTFIRYAMAWFRQAPGKE
REFVAAIPQSGGRSYYADSVKGRFTISRDN
AKNTVYLQMNSLKPEDTAVYSCAATSTYYG
RSAYSSHSGGYDYWGQGTQVTVSS*GGGSGG*
*GSGGGSGGGS*QVQLVQSGGGLVQAGDSLRL
SCAASGRTFIRYAMAWFRQAPGKEREFVAA
IPQSGGRSYYADSVKGRFTISRDNAKNTVY
LQMNSLKPEDTAVYSCAATSTYYGRSAYSS
HSGGYDYWGQGTQVTVSS*GGGS*EITRTTLQ
SDQEEIDYDDTISVEMKKEDFDIFDEDENQ
SPRSFQKKTRHYFIAAVERLWDYGMSSSPH
VLRNRAQSGSVPQFKKVVFQEFTDGSFTQP
LYRGELNEHLGLLGPYIRAEVEDNIMVTFR
NQASRPYSFYSSLISYEEDQRQGAEPRKNF
VKPNETKTYFWKVQHHMAPTKDEFDCKAWA
YFSDVDLEKDVHSGLIGPLLVCHTNTLNPA
HGRQVTVQEFALFFTIFDETKSWYFTENME
RNCRAPCNIQMEDPTFKENYRFHAINGYIM
DTLPGLVMAQDQRIRWYLLSMGSNENIHSI
HFSGHVFTVRKKEEYKMALYNLYPGVFETV
EMLPSKAGIWRVECLIGEHLHAGMSTLFLV
YSNKCQTPLGMASGHIRDFQITASGQYGQW
APKLARLHYSGSINAWSTKEPFSWIKVDLL
APMIIHGIKTQGARQKFSSLYISQFIIMYS
LDDGKKWQTYRGNSTGTLMVFFGNVDSSGI
KHNIFNPPIIARYIRLHPTHYSIRSTLRME
WMGCDLNSCSMPLGMESKAISDAQITASSY
FTNMFATWSPSKARLHLQGRSNAWRPQVNN
PKEWLQVDFQKTMKVTGVTTQGVKSLLTSM
YVKEFLISSSQDGHQWTLFFQNGKVKVFQG
NQDSFTPVVNSLDPPLLTRYLRIHPQSWVH
QIALRMEVLGCEAQDL<u>YLTPRGVRL</u>*GGGSG*
*GGSGGGSGGGS*QVQLVQSGGGLVQAGDSLR
LSCAASGRTFIRYAMAWFRQAPGKEREFVA
AIPQSGGRSYYADSVKGRFTISRDNAKNTV
YLQMNSLKPEDTAVYSCAATSTYYGRSAYS
SHSGGYDYWGQGTQVTVSS*GGGSGGGSGGG*
*SGGGS*QVQLVQSGGGLVQAGDSLRLSCAAS
GRTFIRYAMAWFRQAPGKEREFVAAIPQSG
GRSYYADSVKGRFTISRDNAKNTVYLQMNS
LKPEDTAVYSCAATSTYYGRSAYSSHSGGY
DYWGQGTQVTVSS*

Italic: GGGS-linker
Bold: sequence KB-VWF-013
Underline: thrombin-cleavage site
Bold underline: mutation p.Y1680F In a particular embodiment, two sdAb directed against VWF are inserted within the B-domain of FVIII, while two sdAb are inserted at the C-terminus (FVIII_KB0013bv (6GGGS)_Cter-0013bv) (SEQ ID NO: 22). Linker between sdAb sequence and FVIII light chain contains 6 GGGS-sequences instead of 1. The C-terminal thrombin cleavage site allows to release sdAb upon FVIII activation.

TABLE K

Sequences of FVIII_KB0013bv(6GGGS)_Cter-0013bv

FVIII_KB0013bv (6GGGS)_Cter-0013bv    Sequence

Polypeptide    SEQ ID NO: 22
MQIELSTCFFLCLLRFCFSATRRYYLGA
VELSWDYMQSDLGELPVDARFPPRVPKS
FPFNTSVVYKKTLFVEFTDHLFNIAKPR
PPWMGLLGPTIQAEVYDTVVITLKNMAS
HPVSLHAVGVSYWKASEGAEYDDQTSQR
EKEDDKVFPGGSHTYVWQVLKENGPMAS
DPLCLTYSYLSHVDLVKDLNSGIGALLV
CREGSLAKEKTQTLHKFILLFAVFDEGK
SWHSETKNSLMQDRDAASARAWPKMHTV
NGYVNRSLPGLIGCHRKSVYWHVIGMGT
TPEVHSIFLEGHTFLVRNHRQASLEISP
ITFLTAQTLLMDLGQFLLFCHISSHQHD
GMEAYVKVDSCPEEPQLRMKNNEEAEDY
DDDLTDSEMDVVRFDDDNSPSFIQIRSV
AKKHPKTWVHYIAAEEEDWDYAPLVLAP
DDRSYKSQYLNNGPQRIGRKYKKVRFMA
YTDETFKTREAIQHESGILGPLLGEVGD
TLLIIFKNQASRPYNIYPHGITDVRPLY
SRRLPKGVKHLKDFPILPGEIFKYKWTV
TVEDGPTKSDPRCLTRYYSSFVNMERDL
ASGLIGPLLICYKESVDQRGNQIMSDKR
NVILFSVFDENRSWYLTENIQRFLPNPA
GVQLEDPEFQASNIMHSINGYVFDSLQL
SVCLHEVAYWYILSIGAQTDFLSVFFSG
YTFKHKMVYEDTLTLFPFSGETVFMSME
NPGLWILGCHNSDFRNRGMTALLKVSSC
DKNTGDYYEDSYEDISAYLLSKNNAIEP
RSFS*GGGS*QVQLVQSGGGLVQAGDSLRL
SCAASGRTFIRYAMAWFRQAPGKEREFV
AAIPQSGGRSYYADSVKGRFTISRDNAK
NTVYLQMNSLKPEDTAVYSCAATSTYYG
RSAYSSHSGGYDYWGQGTQVTVSS*GGGS*
*GGGSGGGSGGGS*QVQLVQSGGGLVQAGD
SLRLSCAASGFTFIRYAMAWFRQAPGKE
REFVAAIPQSGGRSYYADSVKGRFTISR
DNAKNTVYLQMNSLKPEDTAVYSCAATS
TYYGRSAYSSHSGGYDYWGQGTQVTVSS
*GGGSGGGSGGGSGGGSGGGSGGGS*EITR
TTLQSDQEEIDYDDTISVEMKKEDFDIY
DEDENQSPRSFQKKTRHYFIAAVERLWD
YGMSSSPHVLRNRAQSGSVPQFKKVVFQ
EFTDGSFTQPLYRGELNEHLGLLGPYIR
AEVEDNIMVTFRNQASRPYSFYSSLISY
EEDQRQGAEPRKNFVKPNETKTYFWKVQ
HHMAPTKDEFDCKAWAYFSDVDLEKDVH
SGLIGPLLVCHTNTLNPAHGRQVTVQEF
ALFFTIFDETKWWYFTENMERNCRAPCN
IQMEDPTFKENYRFHAINGYIMDTLPGL
VMAQDQRIRWYLLSMGSNENIHSIHFSG
HVFTVRKKEEYKMALYNLYPGVEFTVEM
LPSKAGIWRVECLIGEHLHAGMSTLFLV
YSNKCQTPLGMASGHIRDFQITASGQYG
QWAPKLARLHYSGSINAWSTKEPFSWIK
VDLLAPMIIHGIKTQGARQKFSSLYISQ
FIIMYSLDDGKKWQTYRGNSTGTLMVFFG
NVDSSGIKHNIFNPPIIARYIRLHPTHY
SIRSTLRMEWMGCDLNSCSMPLGMESKA
ISDAQITASSYFTNMFATWSPSKARLHL
QGRSNAWRPQVNNPKEWLQVDFQKTMKV
TGVTTQGVKSLLTSMYVKEFLISSSQDG
HQWTLFFQNGKVKVFQGNQDSFTPVVNS
LDPPLLTRYLRIHPQSWVHQIALRMEVL
GCEAQDLYLTPRGVRL*GGGSGGGSGGGS*
*GGGS*QVQLVQSGGGLVQAGDSLRLSCAA
SGRTFIRYAMAWFRQAPGKEREFVAAIP
QSGGRSYYADSVKGRFTISRDNAKNTVY
LQMNSLKPEDTAVYSCAATSTYYGRSAY
SSHSGGYDYWGQGTQVTVSS*GGGSGGGS*
*GGGSGGGS*QVQLVQSGGGLVQAGDSLRL
SCAASGRTFIRYAMAWFRQAPGKEREFV
AAIPQSGGRSYYADSVKGRFTISRDNAK

TABLE K-continued

Sequences of FVIII_KB0013bv(6GGGS)_Cter-0013bv

| FVIII_KB0013bv (6GGGS)_Cter-0013bv | Sequence |
|---|---|
| | NTVYLQMNSLKPEDTAVYSCAATSTYYG RSAYSSHSGGYDYWGQGTQVTVSS* |

Italic: GGGS-linker
Bold: sequence KB-VWF-013
Underline: thrombin-cleavage site

In a particular embodiment, two sdAb directed against VWF are inserted within the B-domain of FVIII, while two sdAb are inserted at the C-terminus (FVIII_KB0013bv (6GGGS)_Cter-0013bv_Y1680F) (SEQ ID NO: 23). The linker between sdAb sequence and FVIII light chain contains 6 GGGS-sequences instead of 1. The Y1680F mutation allows to avoid natural binding of FVIII to VWF (binding is only mediated by sdAb). The C-terminal thrombin cleavage site allows to release sdAb upon FVIII activation.

TABLE L

Sequences of FVIII_KB0013bv(6GGGS)_Cter-0013bv_Y1680F

| FVIII_KB0013bv (6GGGS)_Cter-0013bv_Y1680F | Sequence |
|---|---|
| Polypeptide | SEQ ID NO: 23<br>MQIELSTCFFLCLLRFCFSATRRYYLGAVELSWD<br>YMQSDLGELPVDARFPPRVPKSFPFNTSVVYKKT<br>LFVEFTDHLFNIAKPRPPWMGLLGPTIQAEVYDT<br>VVITLKNMASHPVSLHAVGVSYWKASEGAEYDDQ<br>TSREKEDDKVFPGGSHTYVWQVLEKNGPMASDPL<br>CLTYSYLSHVDLVKDLNSGLIGALLVCREGSLAK<br>EKTQTLHKFILLFAVFDEGKSWHSETKNSLMQDR<br>DAASARAWPKMHTVNGYVNRSLPGLIGCHRKSVY<br>WHVIGMTTPEVHSIFLEGHTFLVRNHRQASLEI<br>SPITFLTAQTLLMDLGQPLLFCHISSHQHDGMEA<br>YVKVDSCPEEPQLRMKNNEEAEDYDDDLTDSEMD<br>VVRFDDDNSPSFIQIRSVAKKHPKTWVHYIAAEE<br>EWDYAPLVLAPDDRSYKSQYLNNGPQRIGRKYKK<br>VRFMAYTDETFKTREAIQHESGILGPLLYGEVGD<br>TLLIIFKNQASRPYNIYPHGITDVRPLYSRRLPK<br>GVKHLKDFPILPGEIFKYKWTVTVEDGPTKSDPR<br>CLTRYYSSFVNMERDLASGLIGPLLICYKESVDQ<br>RGNQIMSDKRNVILFSVFDENRSWYLTENIQRFL<br>PNPAGVQLEDPEFQASNIMHSINGYVFDSLQLSV<br>CLHEVAYWYILSIGAQTDFLSVFFSGYTFKHKMV<br>YEDTLTLFPFSGETVFMSMENPGLWILGCHNSDF<br>RNRGMTALLKVSSCDKNTGDYYEDSYEDISAYLL<br>SKNNAIEPRSFS*GGGS*QVQLVQSGGGLVQAGDSL<br>RLSCAASGRTFIRYAMAWFRQAPGKEREFVAIIP<br>QSGGRSYYADSVKGRFTISRDNAKNTVYLQMNSL<br>KPEDTAVYSCAATSTYYGRSAYSSHSGGYDYWGQ<br>GTQVTVSS*GGGSGGGSGGGSGGGS*QVQLVQSGGG<br>LVQAGDSLRLSCAASGRTFIRYAMAWFRQAPGKE<br>REFVAAIPQSGGRSYYADSVKGRFTISRDNAKNT<br>VYLQMNSLKPEDTAVYSCAATSTYYGRSAYSSHS<br>GGYDYWGQGTQVTVSS*GGGSGGGSGGGSGGGSGG<br>GSGGGS*EITRTTLQSDQEEIDYDDTISVEMKKED<br>FDIFDEDENQSPRSFQKKTRHYFIAAVERLWDYG<br>MSSSPHVLRNRAQSGSVPQFKKVVFQEFTDGSFT<br>QPLYRGELNEHLGLLGPYIRAEVEDNIMVTFRNQ<br>ASRPYSFYSSLISYEEDQRQGAEPEKNFVKPNET<br>KTYFWKVQHHMAPTKDEFDCKAWAYFSDVDLEKD<br>VHSGLIGPLLVCHTNTLNPAHGRQVTVQEFALFF<br>TIFDETKSWYFTENMERNCRAPCNIQMEDPTFKE<br>NYRFHAINGYIMDTLPGLVMAQSQRIRWYLLSMG<br>SNENIHSIHFSGHVFTVRKKEEYKMALYNLYPGV<br>FETVEMLPSKAGIWRVECLIGEHLHAGMSTLFLV<br>YSNKCQTPLGMASGHIRDFQITASGQYGQWAPKL<br>ARLHYSGSINAWSTKEPFSWIKVDLLAPMIIHGI<br>KTQGARQKFSSLYISQFIIMYSLDGKKWQTYRGN<br>STGTLMVFFGNVDSSGIKHNIFNPPIIARYIRLH |

TABLE L-continued

Sequences of FVIII_KB0013bv(6GGGS)_Cter-0013bv_Y1680F

| FVIII_KB0013bv (6GGGS)_Cter-0013bv_Y1680F | Sequence |
|---|---|
| | PTHYSIRSTLRMEWMGCDLNSCSMPLGMESKAIS<br>DAQITASSYFTNMFATWSPSKARLHLQGRSNAWR<br>PQVNNPKEWLQVDFQKTMKVTGVTTQGVKSLLTS<br>MYVKEFLISSSQDGHQWTLFFQNGKVKVFQGNQD<br>SFTPVVNSLDPPLLTRYLRIHPQSWVHQIALRME<br>VLGCEAQDLYLTPRGVL*GGGSGGGSGGGSGGGS*Q<br>VQLVQSGGGLVQAGDSLRLSCAASGRTFIRYAMA<br>WFRQAPGKEREFVAAIPQSGGRSYYADSVKGRFT<br>ISRDNAKNTVYLQMNSLKPEDTAVYSCAATSTYY<br>GRSAYSSHSGGYDYWGQGTQVTVSS*GGGSGGGSG<br>GGSGGGS*QVQLVQSGGGLVQAGDSLRLSCAASGR<br>TFIRYAMAWFRQAPGKEREFVAAIPQSGGRSYYA<br>DSVKGRFTISRDNAKNTVYLQMNSLKPEDTAVYS<br>CAATSTYYGRSAYSSHSGGYDYWGQGTQVTVSS* |

Italic: GGGS-linker
Bold: sequence KB-VWF-013
Underline: thrombin-cleavage site
Bold underline: mutation p.Y1680F In a particular embodiment, the clotting factor is FVII. The terms "Factor VII" and "FVII" are used interchangeably herein. Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa or thrombin in vitro. Factor Xa is believed to be the major physiological activator of Factor VII. Like several other plasma proteins involved in haemostasis. Factor VII is dependent on vitamin K for its activity, which is required for the γ-carboxylation of multiple glutamic acid residues that are clustered in the amino terminus of the protein. These γ-carboxylated glutamic acids are required for the metal-associated interaction of Factor VII with phospholipids.

The conversion of zymogen Factor VII into the activated two-chain molecule occurs by cleavage of an internal peptide bond located approximately in the middle of the molecule. In human Factor VII, the activation cleavage site is at Arg152-Ile153. In the presence of tissue Factor, phospholipids and calcium ions, the two-chain Factor VIIa rapidly activates Factor X or Factor IX by limited proteolysis. Commercially available therapeutic FVII products include plasma derived FVII (pdFVII), such as Factor VII® (=Immuseven commercialized by Baxter) and recombinant FVII (rFVII) products, such as NovoSeven® which is commercialized by NovoNordisk, and other recombinant FVII products which are on clinical trials: prLA-rFVIIa of Novonordisk (phase I/II trial), CSL689 rVIIa-FP of CSL Behring (phase II/III trial), BAX 817 of Baxter (phase III trial), LR769 of rEVO Biologies and LFB Biotechnologies (phase III trial), BAY 86-6150 eptacog alfa of Bayer (phase II/III trial), Factor VIIa-CTP of OPKO Health (phase 11 trial) or PF-05280602 of Pfizer (phase 1 trial).

In certain embodiments, the polypeptide comprises a FVII polypeptide and at least one sdAb directed against VWF according to the invention, wherein said FVII polypeptide comprises Gla domain, hydrophobic region, EGF1 and EGF2 domains, catalytic domains (His-Asp-Ser) and wherein said at least one single-domain antibody directed against VWF is linked to said FVII polypeptide at the C-terminus of said FVII polypeptide.

The typical half-life of a human FVII in humans is several hours (42 hours, Osterm et al 2007, Thromb Haemostas vol 98, pp 790-797). In some embodiments, the chimeric FVII polypeptide has extended half-life compared to wild type FVII polypeptide. In certain embodiments, the half-life of the chimeric FVII polypeptide is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVII.

In a particular embodiment, the sdAb directed against VWF are inserted at the C-ter domain of factor VII (FVII-KB13-bv) (SEQ ID NO: 14).

TABLE M

Sequences of FVII-KB13-bv

| FVII-KB13-bv | Sequence |
|---|---|
| Polypeptide | SEQ ID NO: 14<br>MVSQALRLLCLLLGLQGCLAAGGVAKASGGETRDMP<br>WKPGPHRVFVTQEEAHGVLHRRRRANAFLEELRPGS<br>LERECKEEQCSFEEAREIFKDAERTKLFWISYSDGD<br>QCASSPCQNGGSCKDQLQSYICFCLPAFEGRNCETH<br>KDDQLICVNENGGCEQYCSDHTGTKRSCRCHEGYSL<br>LADGVSCTPTVEYPCGKIPILEKRNASKPQGRIVGG<br>KVCPKGECPQVLLLVNGAQLCGGTLINTIWVVSAAH<br>CFDKIKNWRNLIAVLGEHDLSEHDGDEQSRRVAQVI<br>IPSTYYVPGTTNHDIALLRLHQPVVLTDHVVPLCLP<br>ERTFSERTLAFVRFSLVSGWGQLLDRGATALELMVL<br>NVPRLMTQDCLQQSRKVGDSPNITEYMFCAGYSDGS<br>KDSCKGDSGGPHATHYRGTWYLTGIVSWGQGCATVG<br>HFGVYTRVSQYIEWLQKLMRSEPRPGVLLRAPFPLT<br>PRGVRLGGGSGGGSGGGSGGGSQVQLVQSGGGLVQA<br>GDSLRLSCAASGRTFIRYAMAWFRQAPGKEREFVAA<br>IPQSGGRSYYADSVKGRFTISRDNAKNTVYLQMNSL<br>KPEDTAVYSCAATSTYYGRSAYSSHSGGYDYWGQGT<br>QVTVSSGGGSGGGSGGGSGGGSQVQLVQSGGGLVQA<br>GDSLRLSCAASGRTFIRYAMAWFRQAPGKEREFVAA<br>IPQSGGRSYYADSVKGRFTISRDNAKNTVYLQMNSL<br>KPEDTAVYSCAATSTYYGRSAYSSHSGGYDYWGQGT<br>QVTVSS |

In a particular embodiment, the chimeric polypeptide according to the invention, wherein two sdAb directed against VWF: i) are replacing the C-terminal part of the B domain of factor VIII (FVIII-KB13-bv) (SEQ ID NO: 13; SEQ ID NO: 16: SEQ ID NO: 17); ii) are fused to the C-terminus of FVIII (SEQ ID NO: 18; SEQ ID NO: 19); iii) are simultaneously replacing the C-terminal part of the B domain of factor VIII and fused to C-terminus of factor VIII (SEQ ID NO: 20; SEQ ID NO: 21; SEQ ID NO 22; SEQ ID NO 23); or iv) are inserted at the C-terminus of factor VII (SEQ ID NO: 14).

In a particular embodiment, the chimeric polypeptide according to the invention, wherein the polypeptide comprises at least one single-domain antibody directed against a first antigen and at least one further binding site directed against a second antigen.

According to the invention, the single domain antibodies and polypeptides of the invention may be produced by conventional automated peptide synthesis methods or by recombinant expression. General principles for designing and making proteins are well known to those of skill in the art.

The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a polypeptide of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors: yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), WI38, BHK, HepG2, 3T3. RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the single domain antibodies and polypeptides of the invention, it would be necessary to employ vectors comprising polynucleotide molecules for encoding the single domain antibodies and polypeptides of the invention. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence.

Chimeric Polypeptide/VWF Complexes According to the Invention

In another aspect, the invention relates to a chimeric polypeptide/VWF complex wherein the chimeric polypeptide is a chimeric polypeptide of the invention above-described and a VWF polypeptide with extended half-life.

As used herein, the term "VWF polypeptide with extended half-life" refers to variants of VWF or fragments thereof (including especially D'D3 domain) with insertions, deletions and substitutions, either conservative or non-conservative, where such changes do not alter the biological activities of VWF, or derivatives of WVF such as Fc-fusion, leading to an extended half-life compared to the native VWF. The typical half-life of a human VWF in humans is 16 hours (Goudemand et al 2005).

In one embodiment, the VWF polypeptide with extended half-life is a PEGylated rVWF (PEGrVWF).

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

In a particular embodiment, the VWF polypeptide with extended half-life is a PEGylated VWF D'D3.

In a particular embodiment, the VWF polypeptide with extended half-life is a VWF D'D3 conjugated to albumin (D'D3-Alb).

In a particular embodiment, the VWF polypeptide with extended half-life is VWF D'D3-Fc (VWF D'D3-Fc has a prolonged half-life relative to VWF D'D3 because of interactions with the Fc receptor FcRn recycling pathway)[3].

Other possibilities of modifications to prolong the half-life of VWF or VWF D'D3 are HEPylation, polysialylation or the attachment of XTEN-polypeptides.

Therapeutic Methods and Uses

In another aspect, the invention relates to an isolated single-domain antibody (sdAb) directed against von Willebrand Factor (VWF) D'D3 domain for use as drug.

In another aspect, the invention relates to a chimeric polypeptide comprising a polypeptide and at least one single-domain antibody of the invention for use as drug.

In still another aspect, the invention relates to a chimeric polypeptide/VWF complex of the invention for use as drug.

According to the invention, a single domain antibody of the invention or a chimeric polypeptide of the invention, or a chimeric polypeptide/VWF complex of the invention is administered to the patient with a therapeutically effective amount.

In a particular embodiment, the isolated sdAb directed against VWF D'D3 domain according to the invention, a chimeric polypeptide comprising a polypeptide and at least one sdAb directed against VWF according to the invention, or the chimeric polypeptide/VWF complex according to the invention for use in a method for preventing or treating bleeding disorders.

In another embodiment, the invention is suitable for a method of preventing or treating bleeding disorders in a subject in need thereof, comprising administering to said subject a therapeutically effective amount of a chimeric polypeptide according to the invention or a chimeric polypeptide/VWF complex as described above.

For instance the modified clotting factors according to the invention may be used in a method for preventing and/or treating Weeding disorders. The bleeding disorders that may be treated by administration of the modified dotting factors of the invention include, but are not limited to, hemophilia, as well as deficiencies or structural abnormalities in fibrinogen, prothrombin, Factor V, Factor VII or Factor X.

In a particular embodiment, the bleeding disorders that may be treated by administration of the modified clotting factors of the invention is hemophilia A or hemophilia B.

By a "therapeutically effective amount" is meant a sufficient amount of the polypeptide (or the nucleic acid encoding for the polypeptide) to prevent for use in a method for the treatment of acute exacerbation of chronic obstructive pulmonary disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1.000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Another aspect relates to a pharmaceutical composition comprising a single-domain antibody directed against VWF D'D3 domain, a chimeric polypeptide, a chimeric polypeptide/VWF complex as described herein, and a pharmaceutically acceptable carrier.

The single-domain antibodies and polypeptides of the invention (or the nucleic acid encoding thereof) may be combined with pharmaceutically acceptable excipients, and optionally sustained-release matrices, such as biodegradable polymers, to form pharmaceutical compositions. As used herein, the terms "pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above, in the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The polypeptide (or nucleic acid encoding thereof) may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. The invention will be further illustrated by the following figures and examples.

Methods of Extending or Increasing Half-Life of a Therapeutic Polypeptide

Also disclosed is a method of extending or increasing half-life of a therapeutic polypeptide comprising a step of adding to the polypeptide sequence of said therapeutic polypeptide at least one single-domain antibody directed against VWF D'D3 domain.

In one embodiment, said at least one single-domain antibody directed against VWF is fused or inserted in the polypeptide sequence of said therapeutic polypeptide as above-described. In a particular embodiment, said at least one single-domain antibody directed against VWF is inserted within the B domain of factor VIII as above-described.

Methods for Reducing the Formation of Allo-Antibodies

In some embodiments, the sdAbs of the invention are suitable to reduce the formation of allo-antibodies. In a particular embodiment, at least one single-domain antibody directed against VWF is inserted within the B domain of factor VIII as above-described to reduce the formation of allo-antibodies.

The term "allo-antibodies" has the general meaning in the art and refers to an antibody that occurs naturally against foreign tissues from a person of the same species. Typically, in the context of the invention, incorporating sdAbs against VWF in the FVIII protein avoid the dissociation of FVIII from VWF (FVIII-KB013bv), thus, the subject does not develop allo-antibodies against FVIII-KB013bv which is less immunogenic compared to FVIII that displays normal association-dissociation kinetics.

The invention will be further illustrated by the following figures and examples. However, these examples and figures should not be interpreted in any way as limiting the scope of the present invention.

FIGURES

FIG. 1: Real-time analysis of association and dissociation of VWF interactions with FVIII and sdAbs. Association and dissociation curves for the binding of VWF to immobilized sdAbs and the binding of FVIII to immobilized VWF are plotted in FIG. 1. For the analysis, we focused on the dissociation phase. Apparent dissociation constants were 2.0±1.1×10-5 s-1 (KB-VWF-008), 0.6±0.5×10-5 s-1 (KB-VWF-011), 1.3-3.5×10-5 s-1 (KB-VWF013) and 2.2-3.0× 10-3 s-1 (FVIII).

Figure 2:
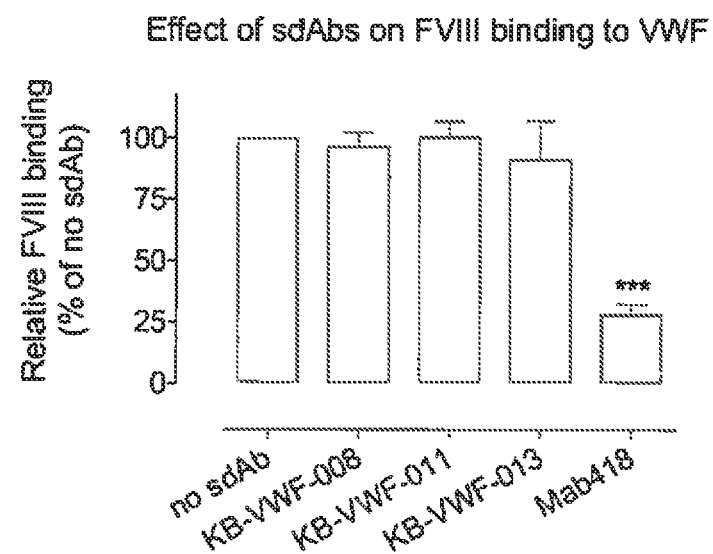

FIG. 2: Effect of sdAbs on VWF binding to Factor VIII. Binding of FVIII to immobilized VWF was determined in the absence or presence of sdAbs or Mab418. Plotted is the percentage FVIII binding relative to FVIII binding in the absence of antibodies. FVIII binding is unaffected by the presence of KB-VWF-008, -011 or -013.

Figure 3:
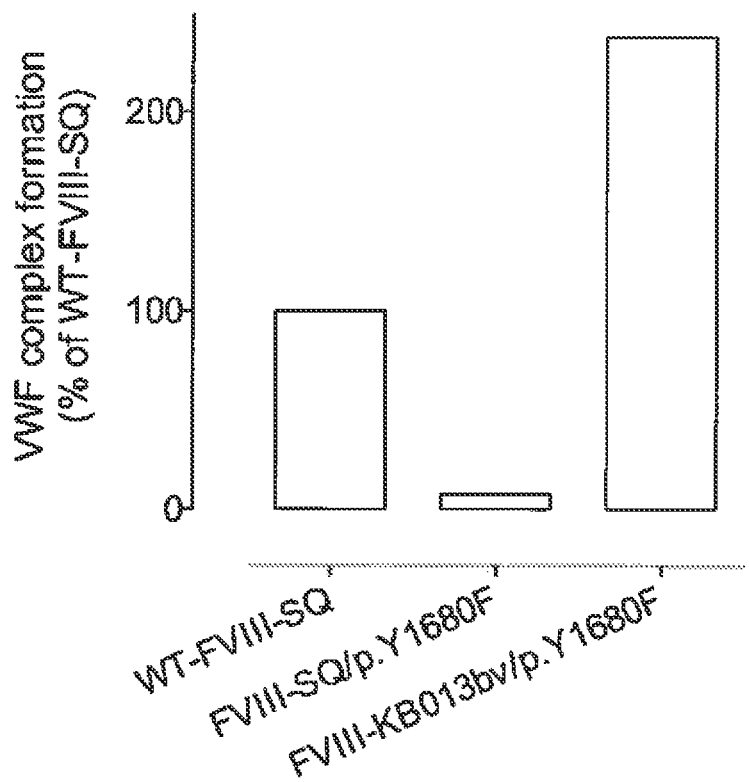

FIG. 3: Factor VIII-sdAb fusion protein binds to VWF. The ability to form a complex with VWF was tested via transient expression of WT-FVIII-SQ, FVIII-SQ/p.Y1680F or FVIII-KB013bv/p.Y1680F in hemophilic mice. Four days after gene transfer, VWF/FVIII complexes were determined, which are expressed as the percentage of complex relative to WT-FVIII-SQ. As expected, the presence of the p.Y1680F mutation abrogated binding of FVIII to VWF (FVM-SQ/p.Y1680F). In contrast, the introduction of KB-VWF-013 restored and even improved binding to VWF despite the presence of the p.Y1680F mutation.

Figure 4:
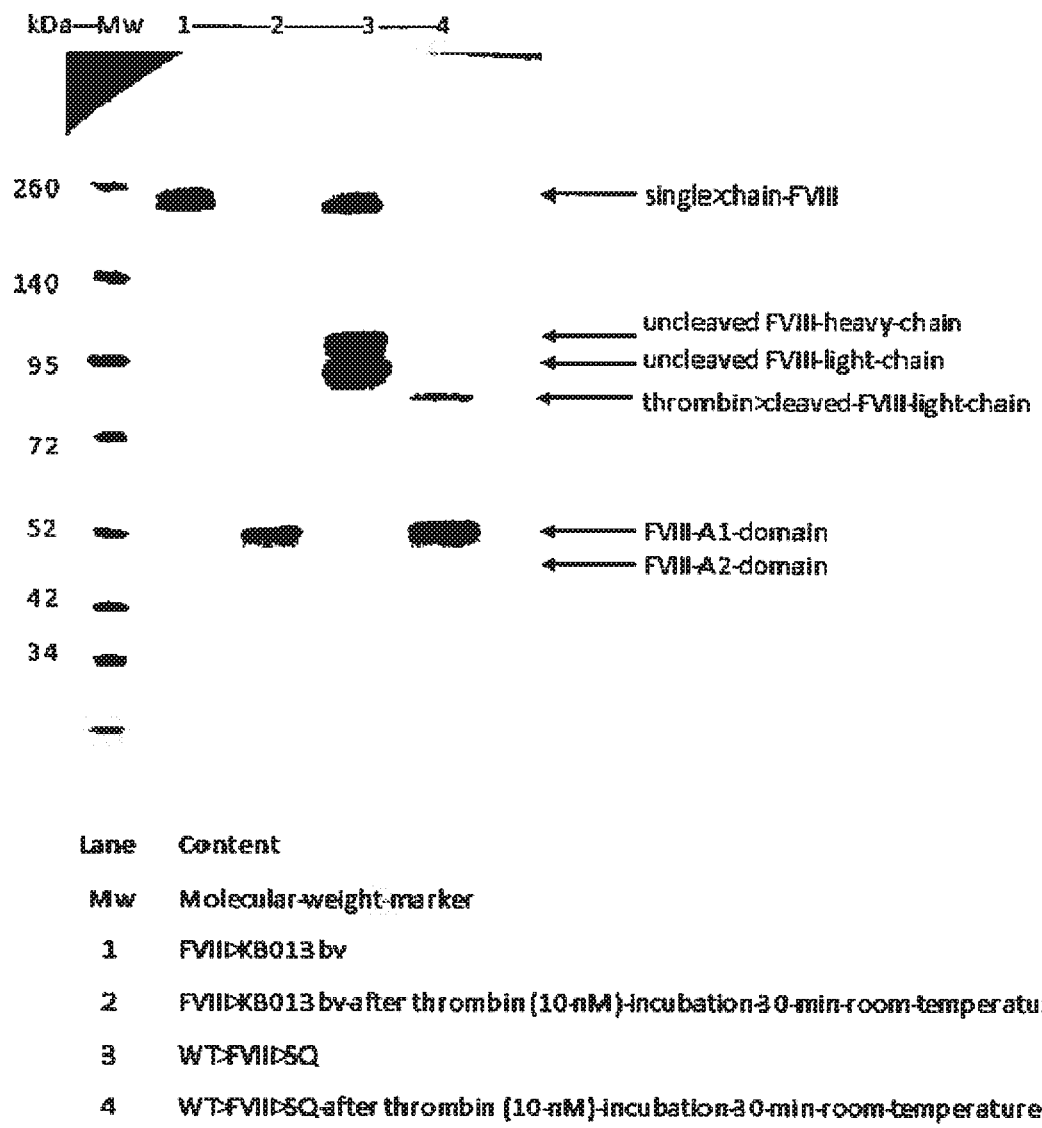

FIG. 4: Expression and functional analysis of FVIII-KB013bv. Purified FVIII-KB013 and WT-FVIII-SQ were incubated in the absence or presence of thrombin. Western blot analysis was performed to determine the presence of FVIII fragments. FVIII-KB013bv migrates predominantly as a single-chain protein when incubated in the absence of thrombin (lane 1), whereas WT-FVIII-SQ predominantly migrates as a heterodimeric protein (lane 3). After thrombin incubation, both FVIII-KB013bv and WT-FVIII-SQ are present as a heterodimeric protein, consisting of the thrombin-cleaved light chain and the heavy-chain derived A1 and A2 domains (lanes 2 & 4).

Figure 5:
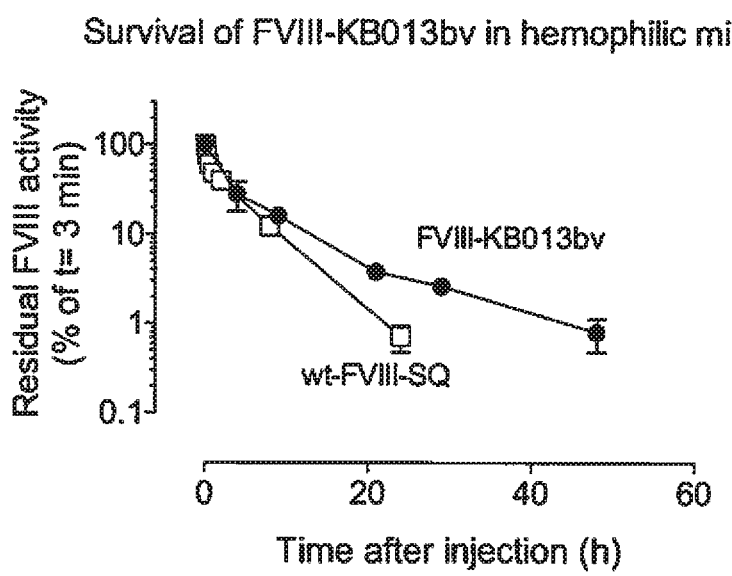

FIG. 5: In vivo survival of FVIII-KB-013bv. FVIII-KB013bv or WT-FVIII-SQ were given intravenously to FVIII-deficient mice. At indicate time-points, blood was collected and FVIII activity was determined. Residual activity relative to activity at 3 min after injection is plotted against time after injection. FVIII-KB013bv is removed from the circulation slower than is WT-FVIII-SQ.

Figure 6:
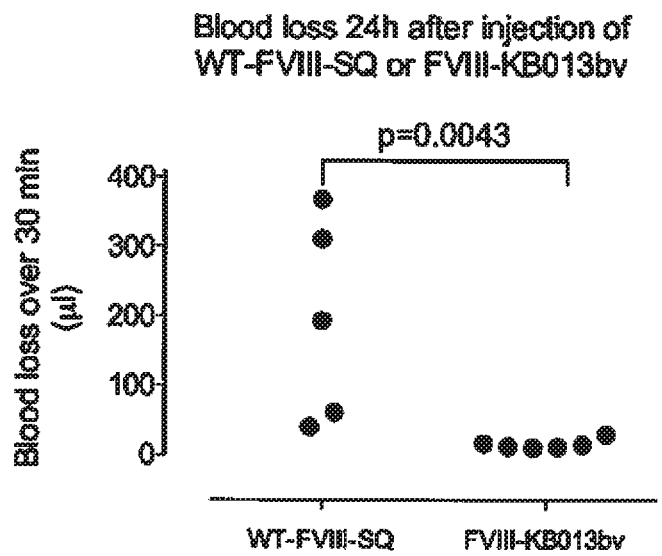

FIG. 6: Correction of hemostasis in hemophilic mice 24 h alter injection of FVIII-KB013bv. FVIII-KB013bv or B-domainless FVIII (Xyntha) were given intravenously to FVIII-deficient mice and 24 h after injection the terminal tip of the tail was amputated in anesthetized mice. Blood loss was monitored for 30 min. The volume of shed blood was determined and is presented for each mouse. Mice treated with FVIII-KB013bv lost significantly less blood compared to mice treated with wild-type B-domainless FVIII.

Figure 7:
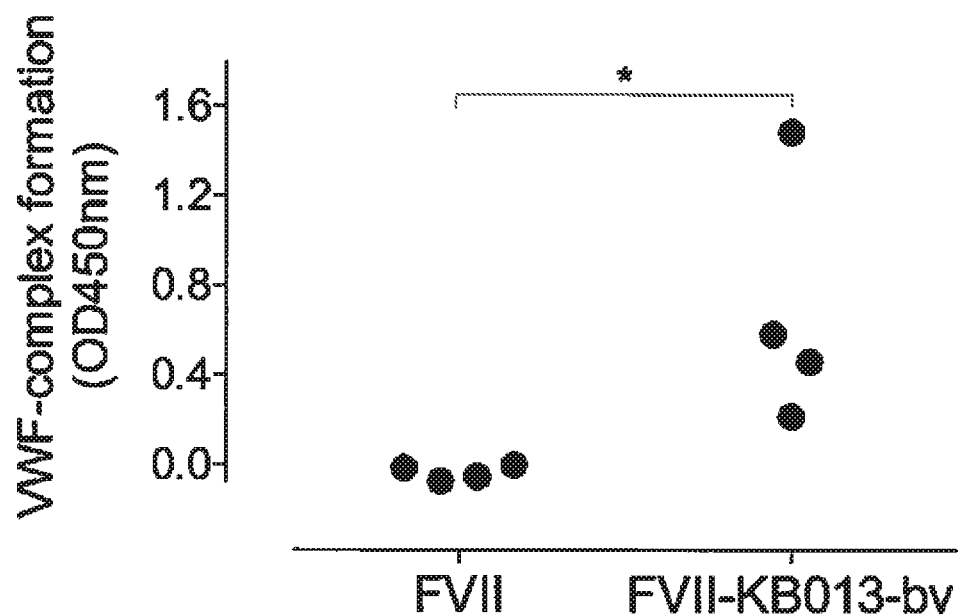

FIG. 7: Fusion of KB-VWF-013 to coagulation factor VII induces complex formation with VWF. The ability to form a complex with VWF was tested via transient expression of wild-type FVII and FVII-KB013-bv in wild-type C57Bl6 mice. Four days after gene transfer, VWF/FVIII complexes were determined, which are expressed as OD450 nm. As expected, no complex formation with VWF could be detected for wild-type FVII. In contrast, VWF-FVII complexes were detected in all mice expressing FVII-KB013-bv. Thus, the fusion of FVII to KB-VWF-013 induces the capacity of FVII to bind to VWF.

EXAMPLES

Example A: Protein Domain Structure of VWF

Bio-informatic analysis of the cDNA and protein sequences of VWF has revealed that the protein architecture distinguishes different types of domain structures. Originally, this domain structure consisted of a signal peptide (SP), A-domains, B-domains, C-domains, D-domains and a CK-domain arranged in the order SP-D1-D2-D'-D3-A1-A2-A3-D4-B1-B2-B3-C1-C2-CK (Verweij C L et al. (1986) EMBO Journal, vol. 5, pp. 1839-1847). More recently an updated domain organization has been proposed, in which the domains are arranged in the following order SP-D1-D2-D'-D3-A1-A2-A3-D4-C1-C2-C3-C4-C5-C6-CK (Zhou Y F et al. (2012) Blood, vol 120. pp. 449-458). Since the boundaries of the different domains may be varying from one publication to another, we use in this application the boundaries as defined in FIG. 1 of Lenting P J et al. (2015) Blood, vol 125, pp. 2019-2028).

Example B: Binding of sdAb to VWF or Fragments Thereof sdAbs KB-VWF-008, -011 and -013 were immobilized (5 μg/ml) in 10 mM NaHCO3, 50 mM Na2CO3 (pH 9.5) in a volume of 50 μl in half-well microtiter plates (Greiner Bio-One, Les Ulis, France) for 16 h at 4° C. As a positive control, polyclonal rabbit anti-VWF antibodies (Dalco, Glostrup, Denmark) were immobilized in a similar fashion. As a negative control, no antibodies were immobilized. After washing the wells three times with 75 μl/well using Tris-buffered saline (pH 7.6) supplemented with 0.1% Tween-20 (TBS-T), wells were blocked with 75 μl/well of TBS-T supplemented with 3% bovine scrum albumin (BSA) for 30 min at 37° C. Wells were washed as described above, and subsequently the following VWF preparations (diluted in Tris-buffered saline (pH 7.6) supplemented with 3% BSA, all at 2 μg/ml, 50 μl per well, 2 hours at 37° C.) were added to each of the immobilized sdAbs and both types of control wells:
  purified recombinant human VWF (rhVWF),
  purified recombinant murine VWF (rmVWF),
  VWF fragment SpII (a proteolytic fragment of plasma-derived (pd)-VWF following incubation with *S. aureus* V8-protease, which encompasses residues 2129-2813 of VWF; Denis C et al. (1993) Arteriosclerosis Thrombosis, vol 13, pp. 398-406),
  VWF fragment SpIII (a proteolytic fragment of pd-VWF following incubation with *S. aureus* V8-protease, which encompasses residues 764-2128 of VWF; Kalafatis M et al. (1987) Blood, vol 70. pp. 1577-1583),
  D'D3-HPC4 fragment (human VWF residues 764-1247 fused to the amino acid sequence EDQVDPRLIDGK (SEQ ID NO: 15), representing a recognition site for antibody HPC4),
  A1-A2-A3-HPC4 fragment (human VWF residues 1260-1874 fused to the amino acid sequence EDQVDPRLIDGK),
  hD1-D2-HPC4 fragment (human VWF residues 23-762 fused to the amino acid sequence EDQVDPRLIDGK),
  mD1-D2*HPC4 fragment (murine VWF residues 23-762 fused to the amino acid sequence EDQVDPRLIDGK)

Wells were then washed three times with 75 μl/well using TBS-T. Bound VWF preparations were probed with peroxidase-labeled polyclonal rabbit anti-VWF antibodies (Dako, Glostrup, Danmark: diluted 1/6000) for rhVWF, rmVWF, SpII and SpIII or with peroxidase-labeled monoclonal antibody HPC4 (diluted 1/1000) for D'D3-HPC4, A1A2A3-HPC4, hD1D2-HPC4 and mD1-D2-HFC4 for 2 hours at 37° C. with 50 μl per well. Wells were then washed three times with 75 μl/well using TBS-T. Residual peroxidase activity was detected by measuring peroxidase-mediated hydrolysis of 3,3',5,5'-tetramethylbenzidine.

Negative binding (−) was defined as optical density (OD) being ≤0.5, moderate positive binding (+) was defined as OD being >0.5 and <1.0, strongly positive binding (++) was defined as OD being ≥1.0. Based on these definitions, none of the VWF preparations displayed moderate or strongly positive binding to the negative control (Table 1). All VWF preparations with the exception of mD1-D2-HPC4 had moderate or strongly positive binding to the positive control (polyclonal anti-VWF antibodies). None of the sdAbs bound to SpII, A1A2A3-HPC4, hD1-D2-HPC4 or mD1-D2-HPC4. In contrast, KB-VWF-008, -011 and -013 had moderate or strongly positive binding to rhVWF, spIII and D'D3-HPC4, suggesting that the epitope of these three sdAbs is located within VWF residues 764-1247. Furthermore, sdAb KB-VWF-013 was the only one of the three tested sdAbs that reacted positively with rmVWF, showing that this sdAb cross-re acts with murine VWF.

| sdAb | rhVWF | rmVWF | SpI | SpII | D'D3-HPC4 | A1A2A3-HPC4 | hD1D2-HPC4 | mD1D2-HPC4 |
|---|---|---|---|---|---|---|---|---|
| 008 | + | − | − | + | ++ | − | − | − |
| 011 | ++ | − | − | + | ++ | − | − | − |
| 013 | ++ | + | − | ++ | ++ | − | − | − |
| Control | ++ | + | ++ | ++ | ++ | ++ | + | − | rhVWF: recombinant human VWF;
rmVWF: recombinant murine VWF;
spI: a proteolytic fragment of plasma-derived (pd)-VWF following incubation with *S. aureus* V8-protease, which encompasses residues 2129-2813 of VWF;
spII: a proteolytic fragment of pd-VWF following incubation with *S. aureus* V8-protease, which encompasses residues 764-2128 of VWF;
D'D3-HPC4: human VWF residues 764-1247 fused to the amino acid sequence EDQVDPRLIDGK;
A1-A2-A3-HPC4: human VWF residues 1260-1874 fused to the amino acid sequence EDQVDPRLIDGK;
hD1-D2-HPC4: human VWF residues 23-762 fused to the amino acid sequence EDQVDPRLIDGK;
mD1-D2-HPC4; murine VWF residues 23-762 fused to the amino acid sequence EDQVDPRLIDGK;
control: polyclonal rabbit-antihuman VWF antibodies (Dako).
−: Negative binding defined as OD being ≤0.5;
+: Moderate positive binding defined as OD being >0.5-<1.0;
++: Strongly positive binding defined as being ≥1.0

Example C: Real-Time Analysis of Association and Dissociation of VWF Interactions with FVIII and sdAbs The interaction between VWF and sdAbs was analyzed via bio-layer interferometry using Octet-QK equipment (Fortébio, Menlo Park, Calif., USA). To this end, sdAbs KB-VWF-008, -011 and -013 were diluted in 0.1 M Mes (pH 5.0) to a concentration of 10 μg/ml for coupling to EDC/NHS-activated amine-reactive biosensors (Fortébio, Menlo Park, Calif., USA). Sensors were rehydrated in 0.2 ml 0.1 M MES. pH 5.0 for 300 sec. Sensors were then activated via incubation with 0.1 ml 02 M EDC/0.095 M NHS mixture for 300 sec and subsequently incubated with 0.1 ml sdAb-solution for 600 sec. Unoccupied amine-reactive sites were quenched by incubating with 1M ethanolamine for 180 sec, and sensors were allowed to reach stable baseline levels via incubation with phosphate-buffered saline supplemented with 0.1% Tween-20 (PBS-T) for 300 sec. sdAb-coated sensors were then transferred to wells containing various concentrations of purified plasma-derived VWF (2.5, 25 & 250 µg/ml in PBS-T for KB-VWF-008 and -011 versus 25 & 250 µg/ml for KB-VWF-013) and incubated for 600 sec in order to visualize association of VWF to immobilized sdAbs. Following this association phase, sensors were transferred to wells containing PBS-T and incubated for 900 sec, allowing dissociation of the VWF-sdAb complex.

In another set of experiments, we determined the association and dissociation of factor VIII to immobilized recombinant human VWF via biolayer-interferometry analysis, also using Octet-QK equipment. Amine-reactive biosensors were used to immobilize recombinant VWF (50 µg/ml in 0.1 M MES, pH 5.0). After hydration of the sensors via a 600-sec incubation with 0.1 M MES pH 5.0, sensors were activated with 0.1 ml 0.2 M EDC/0.095 M NHS mixture for 420 sec and subsequently incubated with 0.1 ml VWF-solution for 420 sec. Unoccupied amine-reactive sites were quenched by incubating with 1M ethanolamine for 420 sec, and sensors were allowed to reach stable baseline levels via incubation with Hepes-buffer (20 mM Hepes, 0.11 M NaCl, 0.005% Tween-20, 5 mM CaCl2, pH 7.3) for 600 sec. VWF-coated sensors were then transferred to wells containing various concentrations of purified recombinant full-length factor VIII (Kogenate; diluted to 3.5 nM or 1.4 nM in Hepes-buffer) and incubated for 600 sec in order to visualize association of FVIII to immobilized VWF. Following this association phase, sensors were transferred to wells containing Hepes-buffer and incubated for 600 sec, allowing dissociation of the VWF-FVIII complex.

Association and dissociation curves are plotted in FIG. 1. When analyzing the data for the interaction between sdAbs and VWF versus the interaction between VWF and FVIII, we focused on the dissociation phase for both types of interaction. The dissociation rate constant for the VWF-FVIII interaction was calculated using an equation for a single exponential decay, and the dissociation rate constants were calculated to be $2.2 \times 10^{-3}$ s-1 and $3.0 \times 10^{-3}$ s-1 for FVIII concentrations of 3.5 nM and 1.4 nM, respectively. These values are similar to those described in the literature ($0.3-6.0 \times 10^{-3}$ s-1; Sandberg et al (2012) Thromb Res vol 130, pp 808-817; Dimitrov et al (2012) Biochemistry vol 51, pp 4108-4116; Zollner et al (2014) Thromb Res vol 134, pp 125-131). The dissociation constants for the sdAbs were could not be calculated accurately using an equation for a single exponential decay, as the dissociation was too slow during the period that was monitored. We used therefore a linear regression approach to determine the slope of the dissociation curve, which represents an apparent dissociation rate constant that probably over-estimates the true dissociation rate constant (i.e. in reality dissociation is slower titan represented by the apparent dissociation rate constant). For KB-VWF-008, the apparent dissociation rate constant was $2.0 \pm 1.1 \times 10^{-5}$ s-1 (mean±standard deviation; n=3 concentrations). For KB-VWF-011, the apparent dissociation rate constant was $0.6 \pm 0.3 \times 10^{-5}$ s-1 (mean±standard deviation; n=3 concentrations). For KB-VWF-013, the apparent dissociation rate constants was $1.3 \times 10^{-5}$ s-1 and $3.5 \times 10^{-5}$ s-1 (for 250 g/ml and 25 g/ml, respectively). Thus, for each of the three sdAbs, the apparent dissociation rates constants for the interaction with VWF are at least 15-300-fold slower compared to those dissociation rates constants reported in the literature for the FVIII-VWF interaction, and at least 100-fold slower compared to the dissociation rate constant calculated for the VWF-FVIII interaction analyzed in the same Octet-QK equipment.

Example D: Effect of sdAbs on VWF Binding to Factor VIII

Polyclonal rabbit anti-VWF antibodies (Dako. Glostrup. Danmark) were immobilized onto microtiter wells at 5 µg/ml in 50 mM Na2CO3 (pH 9.5) overnight at 4° C. in a volume of 50 µl. After washing thrice with Tris-buffered saline supplemented with 0.1% Tween-20 (TBS-T), wells were saturated with 3% BSA in TBS-T. Then rVWF (0.03-1.0 µg/ml; 50 µl/well) was added to the wells and incubated overnight at 4° C. After washing in TBS-T, wells were incubated twice with 75 µl of 0.35 M CaCl2 for 10 min at 37° C., followed by 6 washes with TBTS-T (75 µl/well). Then rFVIII (Kogenate-FS, Bayer Healthcare) diluted to a concentration of 1.5 U/mJ was added in the presence or absence of 20 µg/ml of sdAb KB-VWF-008, -11 or -013 in a total volume of 50 µl. As a control, FVIII was added in the presence of the murine monoclonal anti-VWF antibody Mab418, which blocks binding of FVIII to VWF (Takahashi Y et al. (1987) Blood vol 70, pp 1679-1682). After 2 h at 37° C. and 3 washes with TBS-T (75 µl/well), bound FVIII was probed using peroxidase-labeled polyclonal sheep-anti-FVIII antibodies (Stago BNL, Leiden, the Netherlands) and detected by measuring peroxidase-mediated hydrolysis of 3,3',5,5'-amethylbenzidine. For each VWF concentration, FVIII binding in the presence of sdAb or Mab418 was calculated relative to FVIII binding in the absence of sdAb or Mab418, and expressed in percentage binding (FIG. 2). Whereas the presence of Mab418 reduced binding of FVIII to VWF by 72±5% (mean±standard deviation; n=6; p<0.001 compared to control), the presence of each of the sdAbs left FVIII binding similar to that in the absence of any antibody (p>0.05 when tested using one-way ANOVA with multiple comparisons). This shows that sdAbs KB-VWF-008, -011 and -013 do not interfere with the binding of FVIII to VWF.

Example E: Factor VIII-sdAb Fusion Protein Binds to VWF cDNA constructs encoding wild-type B-domainless FVIII (WT-FVIII-SQ). B-domainless FVIII containing a Tyr to Phe replacement at position 1680 (FVIII-SQ/p.Y1680F) and FVIII-KB013bv containing a Tyr to Phe replacement at position 1680 (FVIII-KB013bv/p.Y1680F) were cloned into the pLIVE-plasmid (Minis Bio, Madison, Wis. USA). Tyrosine at position 1680 is sulfated in WT-FVIII-SQ, a requirement for the binding to von Willebrand factor (VWF) and mutation of p.Tyr1680 to Phe is associated with a loss of VWF binding (Leyte A et al. (1991) J Biol Chem vol 266, pp 740-746). Plasmids (100 g/mouse) were injected into factor VIII-deficient mice via hydrodynamic gene transfer plasmids are diluted in 0.9% saline with the volume corresponding to 10% of the animal's bodyweight (i.e. 2 ml for a 20-gram mouse). The solution is injected in the tail vein within 5 seconds. Four days after gene transfer, blood was collected via retro-orbital puncture from isoflurane-anesthetized mice and plasma was prepared by centrifugation (1500 g for 20 min at 22° C.). Plasma was then used to measure VWF-FVIII complexes that were formed in the plasma of the mice. Complexes were determined as follows: microtiter wells were coated with polyclonal rabbit anti-VWF antibodies (5 µg/ml) as described in example D. After washing thrice with Tris-buffered saline supplemented with 0.1% Tween-20 (TBS-T), wells were saturated with 3% BSA in TBS-T. Then murine plasma samples (diluted 10-fold in TBS-T) were added to the wells and incubated 2 hours at 37° C. After 3 washes with TBS-T (75 µl/well), bound FVIII was probed using peroxidase-labeled polyclonal sheep-anti-FVIII antibodies (Stage BNL Leiden, the Netherlands) and detected by measuring peroxidase-mediated hydrolysis of 3,3',5,5'-tetramethylbenzidine. The amount of VWF-complex for mutants FVIII-SQ/p.Y1680F and FVIII-KB013bv/p.Y1680F was related to that of WT-FVIII-SQ, which was arbitrarily set as 100%. As anticipated, complex formation with VWF was strongly reduced for mutant FVIII-SQ/p.Y1680F (8% compared to 100% for WT-FVIII-SQ; see FIG. 3). In contrast, binding was increased 2.4 fold (238%) for variant FVIII-KB013bv/p.Y1680F, which contains the VWF-binding sdAbs. Since the p.Y1680F mutation abrogates natural VWF binding, these data show that while incorporated in the factor VIII protein, sdAb KB-VWF-013 is able to rescue binding to VWF. Thus, in the context of the fusion protein, sdAb KB-VWF-013 contributes to VWF binding.

Example F: Expression and Functional Analysis of FVIII-KB013bv

Baby Hamster Kidney (BHK)-cells were transfected with cDNA encoding FVIII-KB013bv cloned in pcDNA3.1/Hygro and stable cell lines were obtained via selection with hygromycin. One clone was selected for the production of FVIII-KB013bv. FVIII-KB013bv was purified from the culture medium via affinity chromatography using VIIISelect-matrix as instructed by the manufacturer (GE Healthcare, Vélizy-Villacoublay, France). Purified FVIII-KB013bv was tested for activity and antigen. Five top-fractions were selected and chromogenic two-stage activity (Biophen FVIII:C; Hyphen Biomed, Neuville-sur-Oise, France) and factor VIII antigen levels (Girma J P et al (1998) Haemophilia vol 4 pp 98-103) were determined. Average activity was found to be 188±42 U/ml (mean±SD; n=5 consecutive elution fractions) and antigen was calculated to be 176±28 U/ml. Average activity/antigen ratio was 1.1±0.3, showing that FVIII-KB013bv displays full activity in the chromogenic two-stage activity assay.

In a second analysis, FVIII-KB013bv and WT-FVIII-SQ were incubated with in the absence or presence of thrombin (10 nM) for 30 min at room temperature. Subsequently samples were analyzed via Western blotting using polyclonal sheep anti-FVIII antibodies. For samples incubated in the absence of thrombin. WT-FVIII-SQ is predominantly present in a cleaved form, consisting of a 90-kDa heavy chain and an 80-kDa light chain while some uncleaved material was also present (Lane 3 in FIG. 4). In contrast, for FVIII-KB013bv>90% of the preparation was present as a single-chain protein, appearing as a doublet (Lane 1 in FIG. 4). Of note, the size of the uncleaved FVIII-013bv is slightly larger than that of WT-FVIII-SQ, due to the insertion of two copies of sdAb KB-VWF-013 between the FVIII heavy and tight chain (Lanes 1 & 3 in FIG. 4). In contrast, following incubation with thrombin, WT-FVIII-SQ and FVIII-013bv displayed a similar pattern for thrombin-activated FVIII, with a 70-kDa light chain and the separate A1 and A2 domains (Lanes 2 & 4 in FIG. 4). This analysis indicates that following thrombin activation, the inserted sdAb KB-VWF-013bv is removed from the protein, giving rise to the natural heterotrimeric FVIIIa protein.

Example G: In Vivo Survival of FVIII-KB-013bv

Purified WT-FVIII-SQ or FVIII-kb013bv (both produced in BHK-M cells and purified using VIIISelect-affinity chromatography) were given intravenously (250-500 U/kg) to FVIII-deficient mice. At different time-points after injection (3 min, 30 min, 1 h, 2 h, 8 h and 24 h for WT-FVIII-SQ and 3 min, 4 h, 9 h, 21 h, 29 h and 48 h for FVIII-KB013bv) blood samples were obtained via retro-orbital puncture from isoflurane-anesthetized mice and plasma was prepared by centrifugation (1500 g for 20 min at 22° C.). Residual FVIII activity was measured using a chromogenic two-stage assay as instructed by the manufacturer (Biophen FVIII:C; Hyphen Biomed, Neuville-sur-Oise, France). Residual FVIII activity relative to activity at 3 min after injection was plotted against the time after injection (FIG. 5). This approach revealed that activity for FVIII-KB013bv remained higher WT-FVIII-SQ at later time-points. For instance, relative residual FVIII activity for WT-FVIII at 24 h was 0.72±0.23% (n=3), whereas for FVIII-KB013bv the relative residual activity at 29 h was more than 3-fold higher (2.62±0.25%; n=3; p=0.0007 in student t-test). When data where analyzed using an equation describing a single exponential decay (Graph Prism 5 for Mac OSX, GraphPad Software, La Jolla, Calif., USA), the half-life calculated for WT-FVIII-SQ was 1.1 h (95% confidence interval 0.9-1.5 h). For FVIII-KB013bv the half-life was calculated to be 2.1 h (95% confidence interval 1.7-2.9 h; p=0.0032 compared to WT-FVIII-SQ), 2-fold longer than the half-life for WT-FVIII-SQ. These results show that the presence of two copies of sdAb KB-VWF-013 has a significant beneficial effect on the survival of FVIII.

Example H: Correction of Hemostasis in Hemophilic Mice 24 h Alter Injection of FVIII-KB013bv 8-12 week old hemophilic mice were given WT-FVIII-SQ (Xyntha) or FVIII KB013bv at a dose of 500 U/kg via intravenous tail injection. Twenty-four hours after injection, the terminal 3 mm of the tail-tip was amputated from ketamine/xylazine-anesthetized mice. The amputated tail was immersed immediately after transection in a 50 ml tube full of warm physiological saline. Blood was collected for 30 min at 37° C. After 30 min, the mixture of blood and physiological saline was centrifuged at 1500 g. The red blood cells pellet was then lysed in H2O and the amount of hemoglobin was obtained by reading the absorbance at 416 nm. The volume of blood lost in each sample was calculated from a standard curve, which is obtained by lysing defined volumes (20 µl, 40 µl, 60 µl, 80 µl and 100 µl) of mouse blood in H2G to extract hemoglobin as described above. Blood loss for each mouse is presented in FIG. 6. For mice injected with FVIII-KB013bv, average blood loss was calculated to be 13±3 µl (mean±standard deviation; n=3 mice). For mice that received WT-FVIII-SQ, average blood loss was 194±146 µl (mean±standard deviation; n=5 mice), which is significantly more compared the mice injected with FVIII-KB013bv (p=0.0043 as determined using the Mann-Whitney test). Thus, FVIII-KB013bv displays hemostatic activity for a longer period of time than does WT-FVIII-SQ.

Example 1: Use of FVIII-KB013bv as a Therapeutic Protein to Reduce the Formation of Allo-Antibodies Although VWF and FVIII circulate in plasma as a complex, there is a striking difference in the extent by which allo-antibodies develop following therapeutic application of these proteins. Development of allo-antibodies to VWF in response to replacement therapy is estimated to involve 5-10% of the patients with severe von Willebrand disease (James et al (2013) *Blood* vol 122, pp 636-640), in contrast, inhibitory allo-antibodies arise in up to 27% of previously untreated haemophilia A patients (Iorio et al. (2010) *JTH* vol 8, pp 1256-1265).

The underlying reason for this difference in antibody development rate is unknown. Recently, it has been shown by Sorvillo and colleagues (Haematologica 2016 in press; doi:10.3324/haematol.2015.137067) that VWF remains associated at the surface of antigen-presenting cells without being endocytosed. In contrast, FVIII that was bound to this VWF is actually taken up by these cells and processed for incorporation into MHC-class Q molecules, thereby allowing presentation to CD4+ T-cells. The notion that FVIII but not VWF enters into antigen-presenting cells could explain the antibody development is increased upon FVIII replacement therapy compared to VWF replacement therapy. A method that prevents dissociation of FVIII at the surface of the antigen presenting cell, and thereby uptake of FVIII by the antigen presenting cell would thus be a means to reduce the formation of allo-antibodies upon FVIII replacement therapy. One way to reduce dissociation of FVIII from VWF is by incorporating sdAbs against VWF in the FVIII protein, and an example hereof is FVIII-KB013bv of the present invention. FVIII-KB013bv could therefore be used as a therapeutic protein that is less immunogenic compared to FVIII that displays normal association-dissociation kinetics.

Example J: Fusion of KB-VWF-013 to Coagulation Factor VII Induces Complex Formation with VWF To determine whether sdAbs recognizing VWF can mediate binding of other proteins than FVIII to VWF, a cDNA was constructed encoding the sequence of human coagulation factor VII (FVII) fused to two copies of KB-VWF-013. Sequences encoding FVII and KB-VWF-013 were separated by a linker-sequence encoding a thrombin-cleavage site. The full sequence of this cDNA and corresponding protein is referred to as FVII-KB13-bv. FVII-KB-13-bv and WT-FVII were cloned into the pLIVE-plasmid (Mints Bio, Madison, Wis., USA). Plasmids (100 μg/mouse) were injected into wild-type C57Bl6-mice via hydrodynamic gene transfer plasmids are diluted in 0.9% saline with the volume corresponding to 10% of the animal's bodyweight (i.e. 2 ml for a 20-gram mouse). The solution is injected in the tail vein within 5 seconds. Four days after gene transfer, blood was collected via retro-orbital puncture from isoflurane-anesthetized mice and plasma was prepared by centrifugation (1500 g for 20 min at 22° C.). Plasma was then used to measure complexes between VWF and FVII or FVII-KB13-bv that were formed in the plasma of the mice. Complexes were determined as follows: microtiter wells were coated with polyclonal sheep anti-human FVII antibodies (Affinity Biologicals, Ancaster ON, Canada) at a concentration of 25 μg/ml in 50 μl carbonate-buffer (0.07 M NaHCO3, 0.03 M Na2HCO3, pH 9.6) overnight at 4° C. Wells were washed thrice with Tris-buffered saline supplemented with 0.1% Tween-20 (TBS-T), then saturated with 5% BSA, 1% polyvinylpyrrolidone (PVP) in TBS-T for 2 hours at 37° C. and again washed 5 limes with TBS-T. Then murine plasma samples (diluted 10-fold in 50 μl TBS-T containing 1% BSA) were added to the wells and incubated 2 hours at 37° C. After 5 washes with TBS-T (75 μl/well), bound FVII or FVII-KB13-bv was probed using peroxidase-labeled polyclonal rabbit anti-VWF antibodies (Dako) and detected by measuring peroxidase-mediated hydrolysis of 3,3',5,5'-tetramethylbenzidine. Whereas for mice expressing FVII no signal above the background could be detected (OD450 nm=−0.038±0.033; mean±standard deviation; n=4 mice), suggesting the absence of complexes between VWF and FVII. In contrast, a clear signal was observed for plasma from each mouse expressing FVII-KB13-bv (OD450 nm=0.684±0.554; n=4; p=0.029 analyzed using Mann-Whitney test). This demonstrates that the fusion of FVII to sdAb KB-VWF-013 induces the protein to associate to circulating VWF.

REFERENCES

Throughout this application, various references describe the state of the art to which this invention pertains. The disclosures of these references are hereby incorporated by reference into the present disclosure.
1. Mei B, Pan C, Jiang H, et al. Rational design of a fully active, long-acting PEGylated factor VIII for hemophilia A treatment. Blood 2010; 116(2):270-279.
2. Dumont J A, Liu T, Low S C, et al. Prolonged activity of a recombinant factor VIII-Fc fusion protein in hemophilia A mice and dogs. Blood 2012; 119(13):3024-3030.
3. Yee A, Gildersleeve R D, Gu S, et al. A von Willebrand factor fragment containing the D'D3 domains is sufficient to stabilize coagulation factor VIII in mice. Blood 2014; 124(3):445-452.

The invention claimed is:

1. An isolated single-domain antibody (sdAb) directed against von Willebrand Factor (VWF) D'D3 domain, wherein said sdAb comprises a CDR1 having a sequence set forth as SEQ ID NO: 1, a CDR2 having a sequence set forth as SEQ ID NO: 2 and a CDR3 having a sequence set forth as SEQ ID NO: 3.

2. The isolated single-domain antibody according to claim 1, wherein said sdAb is KB-VWF-013 (SEQ ID NO: 4).

3. An isolated single-domain antibody (sdAb) directed against von Willebrand Factor (VWF) D'D3 domain, wherein said sdAb comprises a CDR1 having a sequence set forth as SEQ ID NO: 5, a CDR2 having a sequence set forth as SEQ ID NO: 6 and a CDR3 having a sequence set forth as SEQ ID NO: 7.

4. The isolated single-domain antibody according to claim 3, wherein said sdAb is KB-VWF-008 (SEQ ID NO: 8).

5. An isolated single-domain antibody (sdAb) directed against von Willebrand Factor (VWF) D'D3 domain, wherein said sdAb comprises a CDR1 having a sequence set forth as SEQ ID NO: 9, a CDR2 having a sequence set forth as SEQ ID NO: 10 and a CDR3 having a sequence set forth as SEQ ID NO: 11.

6. The isolated single-domain antibody according to claim 5, wherein said sdAb is KB-VWF-011 (SEQ ID NO: 12).

7. A method of preventing or treating bleeding disorders in a subject in need thereof, comprising administering to said subject a therapeutically effective amount of a polypeptide, wherein said polypeptide is selected from the group consisting of:
　KB-VWF-013 (SEQ ID NO: 4);
　KB-VWF-008 (SEQ ID NO: 8);
　KB-VWF-011 (SEQ ID NO: 12);
　a sdAb comprising a CDR1 having a sequence set forth as SEQ ID NO: 1, a CDR2 having a sequence set forth as SEQ ID NO: 2 and a CDR3 having a sequence set forth as SEQ ID NO: 3;
　a sdAb comprising a CDR1 having a sequence set forth as SEQ ID NO: 5, a CDR2 having a sequence set forth as SEQ ID NO: 6 and a CDR3 having a sequence set forth as SEQ ID NO: 7; and
　a sdAb comprising a CDR1 having a sequence set forth as SEQ ID NO: 9, a CDR2 having a sequence set forth as SEQ ID NO: 10 and a CDR3 having a sequence set forth as SEQ ID NO: 11.

8. The method according to claim 7 wherein the bleeding disorder is hemophilia A or hemophilia B.

9. A method of extending or increasing half-life of a therapeutic polypeptide comprising a step of adding to the polypeptide sequence of said therapeutic polypeptide at least one sdAb directed against VWF D'D3 domain, wherein said sdAb directed against VWF D'D3 domain is selected from the group consisting of:
　KB-VWF-013 (SEQ ID NO: 4);
　KB-VWF-008 (SEQ ID NO: 8);
　KB-VWF-011 (SEQ ID NO: 12);
　a sdAb comprising a CDR1 having a sequence set forth as SEQ ID NO: 1, a CDR2 having a sequence set forth as SEQ ID NO: 2 and a CDR3 having a sequence set forth as SEQ ID NO: 3;
　a sdAb comprising a CDR1 having a sequence set forth as SEQ ID NO: 5, a CDR2 having a sequence set forth as SEQ ID NO: 6 and a CDR3 having a sequence set forth as SEQ ID NO: 7 and
a sdAb comprising a CDR1 having a sequence set forth as SEQ ID NO: 9, a CDR2 having a sequence set forth as SEQ ID NO: 10 and a CDR3 having a sequence set forth as SEQ ID NO: 11.

* * * * *

SEQUENCE LISTING

<160> NUMBER OF SEQ ID NOS: 23

<210> SEQ ID NO 1
<211> LENGTH: 9
<212> TYPE: PRT
<213> ORGANISM: Artificial
<220> FEATURE:
<223> OTHER INFORMATION: Synthetic KB-VWF-013 CDR1SEQ ID NO: 1

<400> SEQUENCE: 1

Gly Arg Thr Phe Ile Arg Tyr Ala Met
1               5

<210> SEQ ID NO 2
<211> LENGTH: 16
<212> TYPE: PRT
<213> ORGANISM: Artificial

```
<220> FEATURE:
<223> OTHER INFORMATION: Synthetic KB-VWF-013 CDR2 SEQ ID NO: 2

<400> SEQUENCE: 2

Ile Pro Gln Ser Gly Gly Arg Ser Tyr Tyr Ala Asp Ser Val Lys Gly
1               5                   10                  15

<210> SEQ ID NO 3
<211> LENGTH: 19
<212> TYPE: PRT
<213> ORGANISM: Artificial
<220> FEATURE:
<223> OTHER INFORMATION: Synthetic KB-VWF-013 CDR3 SEQ ID NO: 3

<400> SEQUENCE: 3

Thr Ser Thr Tyr Tyr Gly Arg Ser Ala Tyr Ser Ser His Ser Gly Gly
1               5                   10                  15

Tyr Asp Tyr

<210> SEQ ID NO 4
<211> LENGTH: 128
<212> TYPE: PRT
<213> ORGANISM: Artificial
<220> FEATURE:
<223> OTHER INFORMATION: Synthetic KB-VWF-013 SEQ ID NO: 4

<400> SEQUENCE: 4

Gln Val Gln Leu Val Gln Ser Gly Gly Gly Leu Val Gln Ala Gly Asp
1               5                   10                  15

Ser Leu Arg Leu Ser Cys Ala Ala Ser Gly Arg Thr Phe Ile Arg Tyr
            20                  25                  30

Ala Met Ala Trp Phe Arg Gln Ala Pro Gly Lys Glu Arg Glu Phe Val
        35                  40                  45

Ala Ala Ile Pro Gln Ser Gly Gly Arg Ser Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Ser Cys
                85                  90                  95

Ala Ala Thr Ser Thr Tyr Tyr Gly Arg Ser Ala Tyr Ser Ser His Ser
            100                 105                 110

Gly Gly Tyr Asp Tyr Trp Gly Gln Gly Thr Gln Val Thr Val Ser Ser
        115                 120                 125

<210> SEQ ID NO 5
<211> LENGTH: 10
<212> TYPE: PRT
<213> ORGANISM: Artificial
<220> FEATURE:
<223> OTHER INFORMATION: Synthetic KB-VWF-008 CDR1 SEQ ID NO:5

<400> SEQUENCE: 5

Gly Arg Thr Phe Ser Asp Tyr Ala Met Gly
1               5                   10

<210> SEQ ID NO 6
<211> LENGTH: 16
<212> TYPE: PRT
<213> ORGANISM: Artificial
<220> FEATURE:
<223> OTHER INFORMATION: Synthetic KB-VWF-008 CDR2 SEQ ID NO: 6

<400> SEQUENCE: 6
```

```
Ile Asn Arg Ser Gly Gly Arg Leu Ser Tyr Ala Glu Ser Val Asn Asp
1               5                   10                  15

<210> SEQ ID NO 7
<211> LENGTH: 16
<212> TYPE: PRT
<213> ORGANISM: Artificial
<220> FEATURE:
<223> OTHER INFORMATION: Synthetic KB-VWF-008 CDR3 SEQ ID NO: 7

<400> SEQUENCE: 7

Arg Thr Asn Trp Asn Pro Pro Arg Pro Leu Pro Glu Glu Tyr Asn Tyr
1               5                   10                  15

<210> SEQ ID NO 8
<211> LENGTH: 125
<212> TYPE: PRT
<213> ORGANISM: Artificial
<220> FEATURE:
<223> OTHER INFORMATION: Synthetic KB-VWF-008 SEQ ID NO: 8

<400> SEQUENCE: 8

Gln Val Gln Leu Val Gln Ser Gly Gly Gly Leu Val Gln Ala Gly Asp
1               5                   10                  15

Ser Leu Lys Leu Ser Cys Ala Ala Ser Gly Arg Thr Phe Ser Asp Tyr
            20                  25                  30

Ala Met Gly Cys Ile Leu Gln Asn Pro Gly Lys Glu Arg Asp Phe Val
        35                  40                  45

Ala Ser Ile Asn Arg Ser Gly Gly Arg Leu Ser Tyr Ala Glu Ser Val
    50                  55                  60

Asn Asp Leu Phe Thr Ile Ser Val Asp Asn Ala Lys Asn Met Leu Tyr
65                  70                  75                  80

Leu Gln Met Asn Ser Leu Lys Pro Glu Asp Thr Ala Val His Tyr Cys
                85                  90                  95

Val Leu Arg Thr Asn Trp Asn Pro Pro Arg Pro Leu Pro Glu Glu Tyr
            100                 105                 110

Asn Tyr Trp Gly Gln Glu Thr Gln Val Thr Val Ser Ser
        115                 120                 125

<210> SEQ ID NO 9
<211> LENGTH: 10
<212> TYPE: PRT
<213> ORGANISM: Artificial
<220> FEATURE:
<223> OTHER INFORMATION: Synthetic KB-VWF-011 CDR1 SEQ ID NO:9

<400> SEQUENCE: 9

Gly Gly Thr Phe Ser Asn Tyr Ala Met Gly
1               5                   10

<210> SEQ ID NO 10
<211> LENGTH: 16
<212> TYPE: PRT
<213> ORGANISM: Artificial
<220> FEATURE:
<223> OTHER INFORMATION: Synthetic KB-VWF-011 CDR2 SEQ ID NO: 10

<400> SEQUENCE: 10

Ile Ser Arg Ser Gly His Arg Thr Asp Tyr Ala Asp Ser Ala Lys Gly
1               5                   10                  15

<210> SEQ ID NO 11
```

```
<211> LENGTH: 15
<212> TYPE: PRT
<213> ORGANISM: Artificial
<220> FEATURE:
<223> OTHER INFORMATION: Synthetic KB-VWF-011 CDR3 SEQ ID NO: 11

<400> SEQUENCE: 11

Arg Ser Asp Trp Ser Ile Ala Thr Thr Ala Thr Ser Tyr Asp Tyr
1               5                   10                  15

<210> SEQ ID NO 12
<211> LENGTH: 124
<212> TYPE: PRT
<213> ORGANISM: Artificial
<220> FEATURE:
<223> OTHER INFORMATION: Synthetic KB-VWF-011SEQ ID NO: 12

<400> SEQUENCE: 12

Gln Val Gln Leu Val Gln Ser Gly Gly Gly Leu Val Gln Ala Gly Asp
1               5                   10                  15

Ser Leu Arg Leu Ser Cys Ala Ala Ser Gly Gly Thr Phe Ser Asn Tyr
                20                  25                  30

Ala Met Gly Trp Phe Arg Gln Thr Pro Gly Lys Glu Arg Glu Phe Val
            35                  40                  45

Ala Arg Ile Ser Arg Ser Gly His Arg Thr Asp Tyr Ala Asp Ser Ala
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ser Asp Trp Ser Ile Ala Thr Thr Ala Thr Ser Tyr Asp
            100                 105                 110

Tyr Trp Gly Gln Gly Thr Gln Val Thr Val Ser Ser
        115                 120

<210> SEQ ID NO 13
<211> LENGTH: 1726
<212> TYPE: PRT
<213> ORGANISM: Artificial
<220> FEATURE:
<223> OTHER INFORMATION: Synthetic SEQ ID NO: 13

<400> SEQUENCE: 13

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125
```

-continued

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg

-continued

```
545                 550                 555                 560
Asp Leu Ala Ser Gly Leu Ile Gly Pro Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gly Gly Gly Ser Gln Val
                755                 760                 765

Gln Leu Val Gln Ser Gly Gly Gly Leu Val Gln Ala Gly Asp Ser Leu
                770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
                805                 810                 815

Ile Pro Gln Ser Gly Gly Arg Ser Tyr Tyr Ala Asp Ser Val Lys Gly
                820                 825                 830

Arg Phe Thr Ile Ser Arg Asp Asn Ala Lys Asn Thr Val Tyr Leu Gln
                835                 840                 845

Met Asn Ser Leu Lys Pro Glu Asp Thr Ala Val Tyr Ser Cys Ala Ala
                850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                885                 890                 895

Gly Ser Gly Gly Gly Ser Gly Gly Ser Gly Gly Gly Ser Gln Val
                900                 905                 910

Gln Leu Val Gln Ser Gly Gly Gly Leu Val Gln Ala Gly Asp Ser Leu
                915                 920                 925

Arg Leu Ser Cys Ala Ala Ser Gly Arg Thr Phe Ile Arg Tyr Ala Met
                930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
                965                 970                 975
```

-continued

```
Arg Phe Thr Ile Ser Arg Asp Asn Ala Lys Asn Thr Val Tyr Leu Gln
            980                 985                 990

Met Asn Ser Leu Lys Pro Glu Asp Thr Ala Val Tyr Ser Cys Ala Ala
            995                1000                1005

Thr Ser Thr Tyr Tyr Gly Arg Ser Ala Tyr Ser Ser His Ser Gly
    1010                1015                1020

Gly Tyr Asp Tyr Trp Gly Gln Gly Thr Gln Val Thr Val Ser Ser
    1025                1030                1035

Gly Gly Gly Ser Glu Ile Thr Arg Thr Thr Leu Gln Ser Asp Gln
    1040                1045                1050

Glu Glu Ile Asp Tyr Asp Asp Thr Ile Ser Val Glu Met Lys Lys
    1055                1060                1065

Glu Asp Phe Asp Ile Tyr Asp Glu Asp Glu Asn Gln Ser Pro Arg
    1070                1075                1080

Ser Phe Gln Lys Lys Thr Arg His Tyr Phe Ile Ala Ala Val Glu
    1085                1090                1095

Arg Leu Trp Asp Tyr Gly Met Ser Ser Ser Pro His Val Leu Arg
    1100                1105                1110

Asn Arg Ala Gln Ser Gly Ser Val Pro Gln Phe Lys Lys Val Val
    1115                1120                1125

Phe Gln Glu Phe Thr Asp Gly Ser Phe Thr Gln Pro Leu Tyr Arg
    1130                1135                1140

Gly Glu Leu Asn Glu His Leu Gly Leu Leu Gly Pro Tyr Ile Arg
    1145                1150                1155

Ala Glu Val Glu Asp Asn Ile Met Val Thr Phe Arg Asn Gln Ala
    1160                1165                1170

Ser Arg Pro Tyr Ser Phe Tyr Ser Ser Leu Ile Ser Tyr Glu Glu
    1175                1180                1185

Asp Gln Arg Gln Gly Ala Glu Pro Arg Lys Asn Phe Val Lys Pro
    1190                1195                1200

Asn Glu Thr Lys Thr Tyr Phe Trp Lys Val Gln His His Met Ala
    1205                1210                1215

Pro Thr Lys Asp Glu Phe Asp Cys Lys Ala Trp Ala Tyr Phe Ser
    1220                1225                1230

Asp Val Asp Leu Glu Lys Asp Val His Ser Gly Leu Ile Gly Pro
    1235                1240                1245

Leu Leu Val Cys His Thr Asn Thr Leu Asn Pro Ala His Gly Arg
    1250                1255                1260

Gln Val Thr Val Gln Glu Phe Ala Leu Phe Phe Thr Ile Phe Asp
    1265                1270                1275

Glu Thr Lys Ser Trp Tyr Phe Thr Glu Asn Met Glu Arg Asn Cys
    1280                1285                1290

Arg Ala Pro Cys Asn Ile Gln Met Glu Asp Pro Thr Phe Lys Glu
    1295                1300                1305

Asn Tyr Arg Phe His Ala Ile Asn Gly Tyr Ile Met Asp Thr Leu
    1310                1315                1320

Pro Gly Leu Val Met Ala Gln Asp Gln Arg Ile Arg Trp Tyr Leu
    1325                1330                1335

Leu Ser Met Gly Ser Asn Glu Asn Ile His Ser Ile His Phe Ser
    1340                1345                1350

Gly His Val Phe Thr Val Arg Lys Lys Glu Glu Tyr Lys Met Ala
    1355                1360                1365
```

```
Leu Tyr Asn Leu Tyr Pro Gly Val Phe Glu Thr Val Glu Met Leu
1370            1375                1380

Pro Ser Lys Ala Gly Ile Trp Arg Val Glu Cys Leu Ile Gly Glu
1385            1390                1395

His Leu His Ala Gly Met Ser Thr Leu Phe Leu Val Tyr Ser Asn
1400            1405                1410

Lys Cys Gln Thr Pro Leu Gly Met Ala Ser Gly His Ile Arg Asp
1415            1420                1425

Phe Gln Ile Thr Ala Ser Gly Gln Tyr Gly Gln Trp Ala Pro Lys
1430            1435                1440

Leu Ala Arg Leu His Tyr Ser Gly Ser Ile Asn Ala Trp Ser Thr
1445            1450                1455

Lys Glu Pro Phe Ser Trp Ile Lys Val Asp Leu Leu Ala Pro Met
1460            1465                1470

Ile Ile His Gly Ile Lys Thr Gln Gly Ala Arg Gln Lys Phe Ser
1475            1480                1485

Ser Leu Tyr Ile Ser Gln Phe Ile Ile Met Tyr Ser Leu Asp Gly
1490            1495                1500

Lys Lys Trp Gln Thr Tyr Arg Gly Asn Ser Thr Gly Thr Leu Met
1505            1510                1515

Val Phe Phe Gly Asn Val Asp Ser Ser Gly Ile Lys His Asn Ile
1520            1525                1530

Phe Asn Pro Pro Ile Ile Ala Arg Tyr Ile Arg Leu His Pro Thr
1535            1540                1545

His Tyr Ser Ile Arg Ser Thr Leu Arg Met Glu Trp Met Gly Cys
1550            1555                1560

Asp Leu Asn Ser Cys Ser Met Pro Leu Gly Met Glu Ser Lys Ala
1565            1570                1575

Ile Ser Asp Ala Gln Ile Thr Ala Ser Ser Tyr Phe Thr Asn Met
1580            1585                1590

Phe Ala Thr Trp Ser Pro Ser Lys Ala Arg Leu His Leu Gln Gly
1595            1600                1605

Arg Ser Asn Ala Trp Arg Pro Gln Val Asn Asn Pro Lys Glu Trp
1610            1615                1620

Leu Gln Val Asp Phe Gln Lys Thr Met Lys Val Thr Gly Val Thr
1625            1630                1635

Thr Gln Gly Val Lys Ser Leu Leu Thr Ser Met Tyr Val Lys Glu
1640            1645                1650

Phe Leu Ile Ser Ser Ser Gln Asp Gly His Gln Trp Thr Leu Phe
1655            1660                1665

Phe Gln Asn Gly Lys Val Lys Val Phe Gln Gly Asn Gln Asp Ser
1670            1675                1680

Phe Thr Pro Val Val Asn Ser Leu Asp Pro Pro Leu Leu Thr Arg
1685            1690                1695

Tyr Leu Arg Ile His Pro Gln Ser Trp Val His Gln Ile Ala Leu
1700            1705                1710

Arg Met Glu Val Leu Gly Cys Glu Ala Gln Asp Leu Tyr
1715            1720                1725

<210> SEQ ID NO 14
<211> LENGTH: 761
<212> TYPE: PRT
<213> ORGANISM: Artificial
<220> FEATURE:
<223> OTHER INFORMATION: Synthetic FVII-KB13-bv SEQ ID NO: 14
```

<400> SEQUENCE: 14

```
Met Val Ser Gln Ala Leu Arg Leu Leu Cys Leu Leu Leu Gly Leu Gln
 1               5                  10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
                100                 105                 110

Ser Pro Cys Gln Asn Gly Gly Ser Cys Lys Asp Gln Leu Gln Ser Tyr
            115                 120                 125

Ile Cys Phe Cys Leu Pro Ala Phe Glu Gly Arg Asn Cys Glu Thr His
130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
210                 215                 220

Pro Gln Val Leu Leu Val Asn Gly Ala Gln Leu Cys Gly Gly Thr
225                 230                 235                 240

Leu Ile Asn Thr Ile Trp Val Val Ser Ala Ala His Cys Phe Asp Lys
                245                 250                 255

Ile Lys Asn Trp Arg Asn Leu Ile Ala Val Leu Gly Glu His Asp Leu
            260                 265                 270

Ser Glu His Asp Gly Asp Glu Gln Ser Arg Arg Val Ala Gln Val Ile
        275                 280                 285

Ile Pro Ser Thr Tyr Val Pro Gly Thr Thr Asn His Asp Ile Ala Leu
290                 295                 300

Leu Arg Leu His Gln Pro Val Val Leu Thr Asp His Val Val Pro Leu
305                 310                 315                 320

Cys Leu Pro Glu Arg Thr Phe Ser Glu Arg Thr Leu Ala Phe Val Arg
                325                 330                 335

Phe Ser Leu Val Ser Gly Trp Gly Gln Leu Leu Asp Arg Gly Ala Thr
            340                 345                 350

Ala Leu Glu Leu Met Val Leu Asn Val Pro Arg Leu Met Thr Gln Asp
        355                 360                 365

Cys Leu Gln Gln Ser Arg Lys Val Gly Asp Ser Pro Asn Ile Thr Glu
370                 375                 380

Tyr Met Phe Cys Ala Gly Tyr Ser Asp Gly Ser Lys Asp Ser Cys Lys
385                 390                 395                 400

Gly Asp Ser Gly Gly Pro His Ala Thr His Tyr Arg Gly Thr Trp Tyr
```

```
            405                 410                 415
Leu Thr Gly Ile Val Ser Trp Gly Gln Gly Cys Ala Thr Val Gly His
        420                 425                 430

Phe Gly Val Tyr Thr Arg Val Ser Gln Tyr Ile Glu Trp Leu Gln Lys
        435                 440                 445

Leu Met Arg Ser Glu Pro Arg Pro Gly Val Leu Leu Arg Ala Pro Phe
450                 455                 460

Pro Leu Thr Pro Arg Gly Val Arg Leu Gly Gly Ser Gly Gly Gly
465                 470                 475                 480

Ser Gly Gly Gly Ser Gly Gly Gly Ser Gln Val Gln Leu Val Gln Ser
                485                 490                 495

Gly Gly Gly Leu Val Gln Ala Gly Asp Ser Leu Arg Leu Ser Cys Ala
                500                 505                 510

Ala Ser Gly Arg Thr Phe Ile Arg Tyr Ala Met Ala Trp Phe Arg Gln
            515                 520                 525

Ala Pro Gly Lys Glu Arg Glu Phe Val Ala Ala Ile Pro Gln Ser Gly
530                 535                 540

Gly Arg Ser Tyr Tyr Ala Asp Ser Val Lys Gly Arg Phe Thr Ile Ser
545                 550                 555                 560

Arg Asp Asn Ala Lys Asn Thr Val Tyr Leu Gln Met Asn Ser Leu Lys
                565                 570                 575

Pro Glu Asp Thr Ala Val Tyr Ser Cys Ala Ala Thr Ser Thr Tyr Tyr
                580                 585                 590

Gly Arg Ser Ala Tyr Ser Ser His Ser Gly Gly Tyr Asp Tyr Trp Gly
            595                 600                 605

Gln Gly Thr Gln Val Thr Val Ser Ser Gly Gly Ser Gly Gly Gly
        610                 615                 620

Ser Gly Gly Gly Ser Gly Gly Gly Ser Gln Val Gln Leu Val Gln Ser
625                 630                 635                 640

Gly Gly Gly Leu Val Gln Ala Gly Asp Ser Leu Arg Leu Ser Cys Ala
                645                 650                 655

Ala Ser Gly Arg Thr Phe Ile Arg Tyr Ala Met Ala Trp Phe Arg Gln
            660                 665                 670

Ala Pro Gly Lys Glu Arg Glu Phe Val Ala Ala Ile Pro Gln Ser Gly
        675                 680                 685

Gly Arg Ser Tyr Tyr Ala Asp Ser Val Lys Gly Arg Phe Thr Ile Ser
        690                 695                 700

Arg Asp Asn Ala Lys Asn Thr Val Tyr Leu Gln Met Asn Ser Leu Lys
705                 710                 715                 720

Pro Glu Asp Thr Ala Val Tyr Ser Cys Ala Ala Thr Ser Thr Tyr Tyr
                725                 730                 735

Gly Arg Ser Ala Tyr Ser Ser His Ser Gly Gly Tyr Asp Tyr Trp Gly
            740                 745                 750

Gln Gly Thr Gln Val Thr Val Ser Ser
        755                 760

<210> SEQ ID NO 15
<211> LENGTH: 12
<212> TYPE: PRT
<213> ORGANISM: Artificial
<220> FEATURE:
<223> OTHER INFORMATION: Synthetic SEQ ID NO: 15

<400> SEQUENCE: 15

Glu Asp Gln Val Asp Pro Arg Leu Ile Asp Gly Lys
```

-continued

<210> SEQ ID NO 16
<211> LENGTH: 1746
<212> TYPE: PRT
<213> ORGANISM: Artificial
<220> FEATURE:
<223> OTHER INFORMATION: Synthetic FVIII_KB0013bv(6GGGS) SEQ ID NO: 16

<400> SEQUENCE: 16

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp

-continued

```
                355                 360                 365
Leu Thr Asp Ser Glu Met Asp Val Val Arg Phe Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                    405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
            435                 440                 445
Ala Tyr Thr Asp Glu Thr Phe Lys Thr Arg Glu Ala Ile Gln His Glu
        450                 455                 460
Ser Gly Ile Leu Gly Pro Leu Leu Tyr Gly Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
            515                 520                 525
Lys Tyr Lys Trp Thr Val Thr Val Glu Asp Gly Pro Thr Lys Ser Asp
        530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
            595                 600                 605
Asn Ile Gln Arg Phe Leu Pro Asn Pro Ala Gly Val Gln Leu Glu Asp
        610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
        690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
Asn Asn Ala Ile Glu Pro Arg Ser Phe Ser Gly Gly Gly Ser Gln Val
            755                 760                 765
Gln Leu Val Gln Ser Gly Gly Gly Leu Val Gln Ala Gly Asp Ser Leu
        770                 775                 780
```

```
Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
            805                 810                 815

Ile Pro Gln Ser Gly Gly Arg Ser Tyr Tyr Ala Asp Ser Val Lys Gly
        820                 825                 830

Arg Phe Thr Ile Ser Arg Asp Asn Ala Lys Asn Thr Val Tyr Leu Gln
    835                 840                 845

Met Asn Ser Leu Lys Pro Glu Asp Thr Ala Val Tyr Ser Cys Ala Ala
850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                885                 890                 895

Gly Ser Gly Gly Gly Ser Gly Gly Ser Gly Gly Gly Ser Gln Val
                900                 905                 910

Gln Leu Val Gln Ser Gly Gly Gly Leu Val Gln Ala Gly Asp Ser Leu
        915                 920                 925

Arg Leu Ser Cys Ala Ala Ser Gly Arg Thr Phe Ile Arg Tyr Ala Met
930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
            965                 970                 975

Arg Phe Thr Ile Ser Arg Asp Asn Ala Lys Asn Thr Val Tyr Leu Gln
        980                 985                 990

Met Asn Ser Leu Lys Pro Glu Asp Thr Ala Val Tyr Ser Cys Ala Ala
            995                 1000                1005

Thr Ser Thr Tyr Tyr Gly Arg Ser Ala Tyr Ser Ser His Ser Gly
    1010                1015                1020

Gly Tyr Asp Tyr Trp Gly Gln Gly Thr Gln Val Thr Val Ser Ser
        1025                1030                1035

Gly Gly Gly Ser Gly Gly Gly Ser Gly Gly Gly Ser Gly Gly Gly
    1040                1045                1050

Ser Gly Gly Ser Gly Gly Gly Ser Glu Ile Thr Arg Thr Thr
    1055                1060                1065

Leu Gln Ser Asp Gln Glu Glu Ile Asp Tyr Asp Thr Ile Ser
    1070                1075                1080

Val Glu Met Lys Lys Glu Asp Phe Asp Ile Tyr Asp Glu Asp Glu
    1085                1090                1095

Asn Gln Ser Pro Arg Ser Phe Gln Lys Lys Thr Arg His Tyr Phe
    1100                1105                1110

Ile Ala Ala Val Glu Arg Leu Trp Asp Tyr Gly Met Ser Ser Ser
    1115                1120                1125

Pro His Val Leu Arg Asn Arg Ala Gln Ser Gly Ser Val Pro Gln
    1130                1135                1140

Phe Lys Lys Val Val Phe Gln Glu Phe Thr Asp Gly Ser Phe Thr
    1145                1150                1155

Gln Pro Leu Tyr Arg Gly Glu Leu Asn Glu His Leu Gly Leu Leu
    1160                1165                1170

Gly Pro Tyr Ile Arg Ala Glu Val Glu Asp Asn Ile Met Val Thr
    1175                1180                1185
```

-continued

Phe Arg Asn Gln Ala Ser Arg Pro Tyr Ser Phe Tyr Ser Ser Leu
1190                1195                1200

Ile Ser Tyr Glu Glu Asp Gln Arg Gln Gly Ala Glu Pro Arg Lys
1205                1210                1215

Asn Phe Val Lys Pro Asn Glu Thr Lys Thr Tyr Phe Trp Lys Val
1220                1225                1230

Gln His His Met Ala Pro Thr Lys Asp Glu Phe Asp Cys Lys Ala
1235                1240                1245

Trp Ala Tyr Phe Ser Asp Val Asp Leu Glu Lys Asp Val His Ser
1250                1255                1260

Gly Leu Ile Gly Pro Leu Leu Val Cys His Thr Asn Thr Leu Asn
1265                1270                1275

Pro Ala His Gly Arg Gln Val Thr Val Gln Glu Phe Ala Leu Phe
1280                1285                1290

Phe Thr Ile Phe Asp Glu Thr Lys Ser Trp Tyr Phe Thr Glu Asn
1295                1300                1305

Met Glu Arg Asn Cys Arg Ala Pro Cys Asn Ile Gln Met Glu Asp
1310                1315                1320

Pro Thr Phe Lys Glu Asn Tyr Arg Phe His Ala Ile Asn Gly Tyr
1325                1330                1335

Ile Met Asp Thr Leu Pro Gly Leu Val Met Ala Gln Asp Gln Arg
1340                1345                1350

Ile Arg Trp Tyr Leu Leu Ser Met Gly Ser Asn Glu Asn Ile His
1355                1360                1365

Ser Ile His Phe Ser Gly His Val Phe Thr Val Arg Lys Lys Glu
1370                1375                1380

Glu Tyr Lys Met Ala Leu Tyr Asn Leu Tyr Pro Gly Val Phe Glu
1385                1390                1395

Thr Val Glu Met Leu Pro Ser Lys Ala Gly Ile Trp Arg Val Glu
1400                1405                1410

Cys Leu Ile Gly Glu His Leu His Ala Gly Met Ser Thr Leu Phe
1415                1420                1425

Leu Val Tyr Ser Asn Lys Cys Gln Thr Pro Leu Gly Met Ala Ser
1430                1435                1440

Gly His Ile Arg Asp Phe Gln Ile Thr Ala Ser Gly Gln Tyr Gly
1445                1450                1455

Gln Trp Ala Pro Lys Leu Ala Arg Leu His Tyr Ser Gly Ser Ile
1460                1465                1470

Asn Ala Trp Ser Thr Lys Glu Pro Phe Ser Trp Ile Lys Val Asp
1475                1480                1485

Leu Leu Ala Pro Met Ile Ile His Gly Ile Lys Thr Gln Gly Ala
1490                1495                1500

Arg Gln Lys Phe Ser Ser Leu Tyr Ile Ser Gln Phe Ile Ile Met
1505                1510                1515

Tyr Ser Leu Asp Gly Lys Lys Trp Gln Thr Tyr Arg Gly Asn Ser
1520                1525                1530

Thr Gly Thr Leu Met Val Phe Phe Gly Asn Val Asp Ser Ser Gly
1535                1540                1545

Ile Lys His Asn Ile Phe Asn Pro Pro Ile Ile Ala Arg Tyr Ile
1550                1555                1560

Arg Leu His Pro Thr His Tyr Ser Ile Arg Ser Thr Leu Arg Met
1565                1570                1575

Glu Trp Met Gly Cys Asp Leu Asn Ser Cys Ser Met Pro Leu Gly

```
                    1580                1585                1590

Met Glu Ser Lys Ala Ile Ser Asp Ala Gln Ile Thr Ala Ser Ser
    1595                1600                1605

Tyr Phe Thr Asn Met Phe Ala Thr Trp Ser Pro Ser Lys Ala Arg
    1610                1615                1620

Leu His Leu Gln Gly Arg Ser Asn Ala Trp Arg Pro Gln Val Asn
    1625                1630                1635

Asn Pro Lys Glu Trp Leu Gln Val Asp Phe Gln Lys Thr Met Lys
    1640                1645                1650

Val Thr Gly Val Thr Thr Gln Gly Val Lys Ser Leu Leu Thr Ser
    1655                1660                1665

Met Tyr Val Lys Glu Phe Leu Ile Ser Ser Ser Gln Asp Gly His
    1670                1675                1680

Gln Trp Thr Leu Phe Phe Gln Asn Gly Lys Val Lys Val Phe Gln
    1685                1690                1695

Gly Asn Gln Asp Ser Phe Thr Pro Val Val Asn Ser Leu Asp Pro
    1700                1705                1710

Pro Leu Leu Thr Arg Tyr Leu Arg Ile His Pro Gln Ser Trp Val
    1715                1720                1725

His Gln Ile Ala Leu Arg Met Glu Val Leu Gly Cys Glu Ala Gln
    1730                1735                1740

Asp Leu Tyr
    1745

<210> SEQ ID NO 17
<211> LENGTH: 1746
<212> TYPE: PRT
<213> ORGANISM: Artificial
<220> FEATURE:
<223> OTHER INFORMATION: Synthetic FVIII_KB0013bv(6GGGS)_Y1680F SEQ ID
      NO: 17

<400> SEQUENCE: 17

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175
```

-continued

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu

```
                595                 600                 605
Asn Ile Gln Arg Phe Leu Pro Asn Pro Ala Gly Val Gln Leu Glu Asp
            610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gly Gly Gly Ser Gln Val
        755                 760                 765
Gln Leu Val Gln Ser Gly Gly Gly Leu Val Gln Ala Gly Asp Ser Leu
    770                 775                 780
Arg Leu Ser Cys Ala Ala Ser Gly Arg Thr Phe Ile Arg Tyr Ala Met
785                 790                 795                 800
Ala Trp Phe Arg Gln Ala Pro Gly Lys Glu Arg Glu Phe Val Ala Ala
                805                 810                 815
Ile Pro Gln Ser Gly Gly Arg Ser Tyr Tyr Ala Asp Ser Val Lys Gly
            820                 825                 830
Arg Phe Thr Ile Ser Arg Asp Asn Ala Lys Asn Thr Val Tyr Leu Gln
        835                 840                 845
Met Asn Ser Leu Lys Pro Glu Asp Thr Ala Val Tyr Ser Cys Ala Ala
    850                 855                 860
Thr Ser Thr Tyr Tyr Gly Arg Ser Ala Tyr Ser Ser His Ser Gly Gly
865                 870                 875                 880
Tyr Asp Tyr Trp Gly Gln Gly Thr Gln Val Thr Val Ser Ser Gly Gly
                885                 890                 895
Gly Ser Gly Gly Gly Ser Gly Gly Ser Gly Gly Gly Ser Gln Val
            900                 905                 910
Gln Leu Val Gln Ser Gly Gly Gly Leu Val Gln Ala Gly Asp Ser Leu
        915                 920                 925
Arg Leu Ser Cys Ala Ala Ser Gly Arg Thr Phe Ile Arg Tyr Ala Met
    930                 935                 940
Ala Trp Phe Arg Gln Ala Pro Gly Lys Glu Arg Glu Phe Val Ala Ala
945                 950                 955                 960
Ile Pro Gln Ser Gly Gly Arg Ser Tyr Tyr Ala Asp Ser Val Lys Gly
                965                 970                 975
Arg Phe Thr Ile Ser Arg Asp Asn Ala Lys Asn Thr Val Tyr Leu Gln
            980                 985                 990
Met Asn Ser Leu Lys Pro Glu Asp Thr Ala Val Tyr Ser Cys Ala Ala
        995                 1000                1005
Thr Ser Thr Tyr Tyr Gly Arg Ser Ala Tyr Ser Ser His Ser Gly
    1010                1015                1020
```

```
Gly Tyr Asp Tyr Trp Gly Gln Gly Thr Gln Val Thr Val Ser Ser
1025                1030                1035

Gly Gly Gly Ser Gly Gly Gly Ser Gly Gly Gly Ser Gly Gly Gly
1040                1045                1050

Ser Gly Gly Ser Gly Gly Gly Ser Glu Ile Thr Arg Thr Thr
1055                1060                1065

Leu Gln Ser Asp Gln Glu Glu Ile Asp Tyr Asp Asp Thr Ile Ser
1070                1075                1080

Val Glu Met Lys Lys Glu Asp Phe Asp Ile Phe Asp Glu Asp Glu
1085                1090                1095

Asn Gln Ser Pro Arg Ser Phe Gln Lys Lys Thr Arg His Tyr Phe
1100                1105                1110

Ile Ala Ala Val Glu Arg Leu Trp Asp Tyr Gly Met Ser Ser Ser
1115                1120                1125

Pro His Val Leu Arg Asn Arg Ala Gln Ser Gly Ser Val Pro Gln
1130                1135                1140

Phe Lys Lys Val Val Phe Gln Glu Phe Thr Asp Gly Ser Phe Thr
1145                1150                1155

Gln Pro Leu Tyr Arg Gly Glu Leu Asn Glu His Leu Gly Leu Leu
1160                1165                1170

Gly Pro Tyr Ile Arg Ala Glu Val Glu Asp Asn Ile Met Val Thr
1175                1180                1185

Phe Arg Asn Gln Ala Ser Arg Pro Tyr Ser Phe Tyr Ser Ser Leu
1190                1195                1200

Ile Ser Tyr Glu Glu Asp Gln Arg Gln Gly Ala Glu Pro Arg Lys
1205                1210                1215

Asn Phe Val Lys Pro Asn Glu Thr Lys Thr Tyr Phe Trp Lys Val
1220                1225                1230

Gln His His Met Ala Pro Thr Lys Asp Glu Phe Asp Cys Lys Ala
1235                1240                1245

Trp Ala Tyr Phe Ser Asp Val Asp Leu Glu Lys Asp Val His Ser
1250                1255                1260

Gly Leu Ile Gly Pro Leu Leu Val Cys His Thr Asn Thr Leu Asn
1265                1270                1275

Pro Ala His Gly Arg Gln Val Thr Val Gln Glu Phe Ala Leu Phe
1280                1285                1290

Phe Thr Ile Phe Asp Glu Thr Lys Ser Trp Tyr Phe Thr Glu Asn
1295                1300                1305

Met Glu Arg Asn Cys Arg Ala Pro Cys Asn Ile Gln Met Glu Asp
1310                1315                1320

Pro Thr Phe Lys Glu Asn Tyr Arg Phe His Ala Ile Asn Gly Tyr
1325                1330                1335

Ile Met Asp Thr Leu Pro Gly Leu Val Met Ala Gln Asp Gln Arg
1340                1345                1350

Ile Arg Trp Tyr Leu Leu Ser Met Gly Ser Asn Glu Asn Ile His
1355                1360                1365

Ser Ile His Phe Ser Gly His Val Phe Thr Val Arg Lys Lys Glu
1370                1375                1380

Glu Tyr Lys Met Ala Leu Tyr Asn Leu Tyr Pro Gly Val Phe Glu
1385                1390                1395

Thr Val Glu Met Leu Pro Ser Lys Ala Gly Ile Trp Arg Val Glu
1400                1405                1410
```

```
Cys Leu Ile Gly Glu His Leu His Ala Gly Met Ser Thr Leu Phe
    1415            1420            1425

Leu Val Tyr Ser Asn Lys Cys Gln Thr Pro Leu Gly Met Ala Ser
    1430            1435            1440

Gly His Ile Arg Asp Phe Gln Ile Thr Ala Ser Gly Gln Tyr Gly
    1445            1450            1455

Gln Trp Ala Pro Lys Leu Ala Arg Leu His Tyr Ser Gly Ser Ile
    1460            1465            1470

Asn Ala Trp Ser Thr Lys Glu Pro Phe Ser Trp Ile Lys Val Asp
    1475            1480            1485

Leu Leu Ala Pro Met Ile Ile His Gly Ile Lys Thr Gln Gly Ala
    1490            1495            1500

Arg Gln Lys Phe Ser Ser Leu Tyr Ile Ser Gln Phe Ile Ile Met
    1505            1510            1515

Tyr Ser Leu Asp Gly Lys Lys Trp Gln Thr Tyr Arg Gly Asn Ser
    1520            1525            1530

Thr Gly Thr Leu Met Val Phe Phe Gly Asn Val Asp Ser Ser Gly
    1535            1540            1545

Ile Lys His Asn Ile Phe Asn Pro Pro Ile Ile Ala Arg Tyr Ile
    1550            1555            1560

Arg Leu His Pro Thr His Tyr Ser Ile Arg Ser Thr Leu Arg Met
    1565            1570            1575

Glu Trp Met Gly Cys Asp Leu Asn Ser Cys Ser Met Pro Leu Gly
    1580            1585            1590

Met Glu Ser Lys Ala Ile Ser Asp Ala Gln Ile Thr Ala Ser Ser
    1595            1600            1605

Tyr Phe Thr Asn Met Phe Ala Thr Trp Ser Pro Ser Lys Ala Arg
    1610            1615            1620

Leu His Leu Gln Gly Arg Ser Asn Ala Trp Arg Pro Gln Val Asn
    1625            1630            1635

Asn Pro Lys Glu Trp Leu Gln Val Asp Phe Gln Lys Thr Met Lys
    1640            1645            1650

Val Thr Gly Val Thr Thr Gln Gly Val Lys Ser Leu Leu Thr Ser
    1655            1660            1665

Met Tyr Val Lys Glu Phe Leu Ile Ser Ser Ser Gln Asp Gly His
    1670            1675            1680

Gln Trp Thr Leu Phe Phe Gln Asn Gly Lys Val Lys Val Phe Gln
    1685            1690            1695

Gly Asn Gln Asp Ser Phe Thr Pro Val Val Asn Ser Leu Asp Pro
    1700            1705            1710

Pro Leu Leu Thr Arg Tyr Leu Arg Ile His Pro Gln Ser Trp Val
    1715            1720            1725

His Gln Ile Ala Leu Arg Met Glu Val Leu Gly Cys Glu Ala Gln
    1730            1735            1740

Asp Leu Tyr
    1745

<210> SEQ ID NO 18
<211> LENGTH: 1753
<212> TYPE: PRT
<213> ORGANISM: Artificial
<220> FEATURE:
<223> OTHER INFORMATION: Synthetic FVIII_BD_Cter-0013bv SEQ ID NO: 18

<400> SEQUENCE: 18
```

-continued

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
            85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
            165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
            210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
            245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
            325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
            405                 410                 415

Leu Val Leu Ala Pro Asp Asp Arg Ser Tyr Lys Ser Gln Tyr Leu Asn

-continued

```
                420             425             430
Asn Gly Pro Gln Arg Ile Gly Arg Lys Tyr Lys Lys Val Arg Phe Met
            435                 440             445
Ala Tyr Thr Asp Glu Thr Phe Lys Thr Arg Glu Ala Ile Gln His Glu
        450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Pro Pro Val Leu
        755                 760                 765
Lys Arg His Gln Arg Glu Ile Thr Arg Thr Thr Leu Gln Ser Asp Gln
    770                 775                 780
Glu Glu Ile Asp Tyr Asp Asp Thr Ile Ser Val Glu Met Lys Lys Glu
785                 790                 795                 800
Asp Phe Asp Ile Tyr Asp Glu Asp Glu Asn Gln Ser Pro Arg Ser Phe
                805                 810                 815
Gln Lys Lys Thr Arg His Tyr Phe Ile Ala Ala Val Glu Arg Leu Trp
            820                 825                 830
Asp Tyr Gly Met Ser Ser Ser Pro His Val Leu Arg Asn Arg Ala Gln
        835                 840                 845
```

```
Ser Gly Ser Val Pro Gln Phe Lys Val Val Phe Gln Glu Phe Thr
    850             855             860

Asp Gly Ser Phe Thr Gln Pro Leu Tyr Arg Gly Glu Leu Asn Glu His
865             870             875             880

Leu Gly Leu Leu Gly Pro Tyr Ile Arg Ala Glu Val Glu Asp Asn Ile
                885             890             895

Met Val Thr Phe Arg Asn Gln Ala Ser Arg Pro Tyr Ser Phe Tyr Ser
            900             905             910

Ser Leu Ile Ser Tyr Glu Glu Asp Gln Arg Gln Gly Ala Glu Pro Arg
        915             920             925

Lys Asn Phe Val Lys Pro Asn Glu Thr Lys Thr Tyr Phe Trp Lys Val
    930             935             940

Gln His His Met Ala Pro Thr Lys Asp Glu Phe Asp Cys Lys Ala Trp
945             950             955             960

Ala Tyr Phe Ser Asp Val Asp Leu Glu Lys Asp Val His Ser Gly Leu
                965             970             975

Ile Gly Pro Leu Leu Val Cys His Thr Asn Thr Leu Asn Pro Ala His
            980             985             990

Gly Arg Gln Val Thr Val Gln Glu Phe Ala Leu Phe Phe Thr Ile Phe
        995             1000            1005

Asp Glu Thr Lys Ser Trp Tyr Phe Thr Glu Asn Met Glu Arg Asn
    1010            1015            1020

Cys Arg Ala Pro Cys Asn Ile Gln Met Glu Asp Pro Thr Phe Lys
    1025            1030            1035

Glu Asn Tyr Arg Phe His Ala Ile Asn Gly Tyr Ile Met Asp Thr
    1040            1045            1050

Leu Pro Gly Leu Val Met Ala Gln Asp Gln Arg Ile Arg Trp Tyr
    1055            1060            1065

Leu Leu Ser Met Gly Ser Asn Glu Asn Ile His Ser Ile His Phe
    1070            1075            1080

Ser Gly His Val Phe Thr Val Arg Lys Lys Glu Glu Tyr Lys Met
    1085            1090            1095

Ala Leu Tyr Asn Leu Tyr Pro Gly Val Phe Glu Thr Val Glu Met
    1100            1105            1110

Leu Pro Ser Lys Ala Gly Ile Trp Arg Val Glu Cys Leu Ile Gly
    1115            1120            1125

Glu His Leu His Ala Gly Met Ser Thr Leu Phe Leu Val Tyr Ser
    1130            1135            1140

Asn Lys Cys Gln Thr Pro Leu Gly Met Ala Ser Gly His Ile Arg
    1145            1150            1155

Asp Phe Gln Ile Thr Ala Ser Gly Gln Tyr Gly Gln Trp Ala Pro
    1160            1165            1170

Lys Leu Ala Arg Leu His Tyr Ser Gly Ser Ile Asn Ala Trp Ser
    1175            1180            1185

Thr Lys Glu Pro Phe Ser Trp Ile Lys Val Asp Leu Leu Ala Pro
    1190            1195            1200

Met Ile Ile His Gly Ile Lys Thr Gln Gly Ala Arg Gln Lys Phe
    1205            1210            1215

Ser Ser Leu Tyr Ile Ser Gln Phe Ile Ile Met Tyr Ser Leu Asp
    1220            1225            1230

Gly Lys Lys Trp Gln Thr Tyr Arg Gly Asn Ser Thr Gly Thr Leu
    1235            1240            1245
```

```
Met Val Phe Phe Gly Asn Val Asp Ser Ser Gly Ile Lys His Asn
1250                1255                1260

Ile Phe Asn Pro Pro Ile Ile Ala Arg Tyr Ile Arg Leu His Pro
1265                1270                1275

Thr His Tyr Ser Ile Arg Ser Thr Leu Arg Met Glu Trp Met Gly
1280                1285                1290

Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr Leu
1445                1450                1455

Thr Pro Arg Gly Val Arg Leu Gly Gly Gly Ser Gly Gly Gly Ser
1460                1465                1470

Gly Gly Gly Ser Gly Gly Gly Ser Gln Val Gln Leu Val Gln Ser
1475                1480                1485

Gly Gly Gly Leu Val Gln Ala Gly Asp Ser Leu Arg Leu Ser Cys
1490                1495                1500

Ala Ala Ser Gly Arg Thr Phe Ile Arg Tyr Ala Met Ala Trp Phe
1505                1510                1515

Arg Gln Ala Pro Gly Lys Glu Arg Glu Phe Val Ala Ala Ile Pro
1520                1525                1530

Gln Ser Gly Gly Arg Ser Tyr Tyr Ala Asp Ser Val Lys Gly Arg
1535                1540                1545

Phe Thr Ile Ser Arg Asp Asn Ala Lys Asn Thr Val Tyr Leu Gln
1550                1555                1560

Met Asn Ser Leu Lys Pro Glu Asp Thr Ala Val Tyr Ser Cys Ala
1565                1570                1575

Ala Thr Ser Thr Tyr Tyr Gly Arg Ser Ala Tyr Ser Ser His Ser
1580                1585                1590

Gly Gly Tyr Asp Tyr Trp Gly Gln Gly Thr Gln Val Thr Val Ser
1595                1600                1605

Ser Gly Gly Gly Ser Gly Gly Gly Ser Gly Gly Gly Ser Gly Gly
1610                1615                1620

Gly Ser Gln Val Gln Leu Val Gln Ser Gly Gly Gly Leu Val Gln
1625                1630                1635

Ala Gly Asp Ser Leu Arg Leu Ser Cys Ala Ala Ser Gly Arg Thr
```

```
              1640                1645                1650
    Phe Ile Arg Tyr Ala Met Ala Trp Phe Arg Gln Ala Pro Gly Lys
              1655                1660                1665

Glu Arg Glu Phe Val Ala Ala Ile Pro Gln Ser Gly Gly Arg Ser
              1670                1675                1680

Tyr Tyr Ala Asp Ser Val Lys Gly Arg Phe Thr Ile Ser Arg Asp
              1685                1690                1695

Asn Ala Lys Asn Thr Val Tyr Leu Gln Met Asn Ser Leu Lys Pro
              1700                1705                1710

Glu Asp Thr Ala Val Tyr Ser Cys Ala Ala Thr Ser Thr Tyr Tyr
              1715                1720                1725

Gly Arg Ser Ala Tyr Ser Ser His Ser Gly Gly Tyr Asp Tyr Trp
              1730                1735                1740

Gly Gln Gly Thr Gln Val Thr Val Ser Ser
              1745                1750

<210> SEQ ID NO 19
<211> LENGTH: 1753
<212> TYPE: PRT
<213> ORGANISM: Artificial
<220> FEATURE:
<223> OTHER INFORMATION: Synthetic FVIII_BD_Cter-0013bv_Y1680F SEQ ID
      NO: 19

<400> SEQUENCE: 19

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240
```

-continued

```
Ala Ala Ser Ala Arg Ala Trp Pro Lys Met His Thr Val Asn Gly Tyr
            245                 250                 255

Val Asn Arg Ser Leu Pro Gly Leu Ile Gly Cys His Arg Lys Ser Val
        260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
```

```
                660             665             670
Ser Gly Tyr Thr Phe Lys His Lys Met Val Tyr Glu Asp Thr Leu Thr
            675             680             685
Leu Phe Pro Phe Ser Gly Glu Thr Val Phe Met Ser Met Glu Asn Pro
            690             695             700
Gly Leu Trp Ile Leu Gly Cys His Asn Ser Asp Phe Arg Asn Arg Gly
705             710             715             720
Met Thr Ala Leu Leu Lys Val Ser Ser Cys Asp Lys Asn Thr Gly Asp
                725             730             735
Tyr Tyr Glu Asp Ser Tyr Glu Asp Ile Ser Ala Tyr Leu Leu Ser Lys
            740             745             750
Asn Asn Ala Ile Glu Pro Arg Ser Phe Ser Gln Asn Pro Pro Val Leu
            755             760             765
Lys Arg His Gln Arg Glu Ile Thr Arg Thr Thr Leu Gln Ser Asp Gln
            770             775             780
Glu Glu Ile Asp Tyr Asp Asp Thr Ile Ser Val Glu Met Lys Lys Glu
785             790             795             800
Asp Phe Asp Ile Phe Asp Glu Asp Glu Asn Gln Ser Pro Arg Ser Phe
                805             810             815
Gln Lys Lys Thr Arg His Tyr Phe Ile Ala Ala Val Glu Arg Leu Trp
            820             825             830
Asp Tyr Gly Met Ser Ser Pro His Val Leu Arg Asn Arg Ala Gln
            835             840             845
Ser Gly Ser Val Pro Gln Phe Lys Lys Val Val Phe Gln Glu Phe Thr
            850             855             860
Asp Gly Ser Phe Thr Gln Pro Leu Tyr Arg Gly Glu Leu Asn Glu His
865             870             875             880
Leu Gly Leu Leu Gly Pro Tyr Ile Arg Ala Glu Val Glu Asp Asn Ile
                885             890             895
Met Val Thr Phe Arg Asn Gln Ala Ser Arg Pro Tyr Ser Phe Tyr Ser
            900             905             910
Ser Leu Ile Ser Tyr Glu Glu Asp Gln Arg Gln Gly Ala Glu Pro Arg
            915             920             925
Lys Asn Phe Val Lys Pro Asn Glu Thr Lys Thr Tyr Phe Trp Lys Val
            930             935             940
Gln His His Met Ala Pro Thr Lys Asp Glu Phe Asp Cys Lys Ala Trp
945             950             955             960
Ala Tyr Phe Ser Asp Val Asp Leu Glu Lys Asp Val His Ser Gly Leu
                965             970             975
Ile Gly Pro Leu Leu Val Cys His Thr Asn Thr Leu Asn Pro Ala His
            980             985             990
Gly Arg Gln Val Thr Val Gln Glu Phe Ala Leu Phe Phe Thr Ile Phe
            995             1000            1005
Asp Glu Thr Lys Ser Trp Tyr Phe Thr Glu Asn Met Glu Arg Asn
            1010            1015            1020
Cys Arg Ala Pro Cys Asn Ile Gln Met Glu Asp Pro Thr Phe Lys
    1025            1030            1035
Glu Asn Tyr Arg Phe His Ala Ile Asn Gly Tyr Ile Met Asp Thr
    1040            1045            1050
Leu Pro Gly Leu Val Met Ala Gln Asp Gln Arg Ile Arg Trp Tyr
    1055            1060            1065
Leu Leu Ser Met Gly Ser Asn Glu Asn Ile His Ser Ile His Phe
    1070            1075            1080
```

```
Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Trp Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395

Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr Leu
    1445                1450                1455

Thr Pro Arg Gly Val Arg Leu Gly Gly Gly Ser Gly Gly Gly Ser
    1460                1465                1470
```

-continued

```
Gly Gly Gly Ser Gly Gly Gly Ser Gln Val Gln Leu Val Gln Ser
        1475                1480                1485
Gly Gly Gly Leu Val Gln Ala Gly Asp Ser Leu Arg Leu Ser Cys
        1490                1495                1500
Ala Ala Ser Gly Arg Thr Phe Ile Arg Tyr Ala Met Ala Trp Phe
        1505                1510                1515
Arg Gln Ala Pro Gly Lys Glu Arg Glu Phe Val Ala Ala Ile Pro
        1520                1525                1530
Gln Ser Gly Gly Arg Ser Tyr Tyr Ala Asp Ser Val Lys Gly Arg
        1535                1540                1545
Phe Thr Ile Ser Arg Asp Asn Ala Lys Asn Thr Val Tyr Leu Gln
        1550                1555                1560
Met Asn Ser Leu Lys Pro Glu Asp Thr Ala Val Tyr Ser Cys Ala
        1565                1570                1575
Ala Thr Ser Thr Tyr Tyr Gly Arg Ser Ala Tyr Ser Ser His Ser
        1580                1585                1590
Gly Gly Tyr Asp Tyr Trp Gly Gln Gly Thr Gln Val Thr Val Ser
        1595                1600                1605
Ser Gly Gly Gly Ser Gly Gly Gly Ser Gly Gly Gly Ser Gly Gly
        1610                1615                1620
Gly Ser Gln Val Gln Leu Val Gln Ser Gly Gly Gly Leu Val Gln
        1625                1630                1635
Ala Gly Asp Ser Leu Arg Leu Ser Cys Ala Ala Ser Gly Arg Thr
        1640                1645                1650
Phe Ile Arg Tyr Ala Met Ala Trp Phe Arg Gln Ala Pro Gly Lys
        1655                1660                1665
Glu Arg Glu Phe Val Ala Ala Ile Pro Gln Ser Gly Gly Arg Ser
        1670                1675                1680
Tyr Tyr Ala Asp Ser Val Lys Gly Arg Phe Thr Ile Ser Arg Asp
        1685                1690                1695
Asn Ala Lys Asn Thr Val Tyr Leu Gln Met Asn Ser Leu Lys Pro
        1700                1705                1710
Glu Asp Thr Ala Val Tyr Ser Cys Ala Ala Thr Ser Thr Tyr Tyr
        1715                1720                1725
Gly Arg Ser Ala Tyr Ser Ser His Ser Gly Gly Tyr Asp Tyr Trp
        1730                1735                1740
Gly Gln Gly Thr Gln Val Thr Val Ser Ser
        1745                1750

<210> SEQ ID NO 20
<211> LENGTH: 2022
<212> TYPE: PRT
<213> ORGANISM: Artificial
<220> FEATURE:
<223> OTHER INFORMATION: Synthetic FVIII_KB0013bv_Cter-0013bv SEQ ID
      NO: 20

<400> SEQUENCE: 20

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60
```

```
Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
            210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480
```

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gly Gly Gly Ser Gln Val
        755                 760                 765

Gln Leu Val Gln Ser Gly Gly Gly Leu Val Gln Ala Gly Asp Ser Leu
    770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
                805                 810                 815

Ile Pro Gln Ser Gly Gly Arg Ser Tyr Tyr Ala Asp Ser Val Lys Gly
            820                 825                 830

Arg Phe Thr Ile Ser Arg Asp Asn Ala Lys Asn Thr Val Tyr Leu Gln
        835                 840                 845

Met Asn Ser Leu Lys Pro Glu Asp Thr Ala Val Tyr Ser Cys Ala Ala
    850                 855                 860

Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                885                 890                 895

Gly Ser Gly Gly Gly Ser Gly Gly Gly Ser Gly Gly Gly Ser Gln Val

```
            900             905             910
Gln Leu Val Gln Ser Gly Gly Leu Val Gln Ala Gly Asp Ser Leu
                915             920             925
Arg Leu Ser Cys Ala Ala Ser Gly Arg Thr Phe Ile Arg Tyr Ala Met
        930             935             940
Ala Trp Phe Arg Gln Ala Pro Gly Lys Glu Arg Glu Phe Val Ala Ala
945             950             955             960
Ile Pro Gln Ser Gly Gly Arg Ser Tyr Tyr Ala Asp Ser Val Lys Gly
                965             970             975
Arg Phe Thr Ile Ser Arg Asp Asn Ala Lys Asn Thr Val Tyr Leu Gln
            980             985             990
Met Asn Ser Leu Lys Pro Glu Asp Thr Ala Val Tyr Ser Cys Ala Ala
            995             1000            1005
Thr Ser Thr Tyr Tyr Gly Arg Ser Ala Tyr Ser Ser His Ser Gly
        1010            1015            1020
Gly Tyr Asp Tyr Trp Gly Gln Gly Thr Gln Val Thr Val Ser Ser
        1025            1030            1035
Gly Gly Gly Ser Glu Ile Thr Arg Thr Thr Leu Gln Ser Asp Gln
        1040            1045            1050
Glu Glu Ile Asp Tyr Asp Asp Thr Ile Ser Val Glu Met Lys Lys
        1055            1060            1065
Glu Asp Phe Asp Ile Tyr Asp Glu Asp Glu Asn Gln Ser Pro Arg
        1070            1075            1080
Ser Phe Gln Lys Lys Thr Arg His Tyr Phe Ile Ala Ala Val Glu
        1085            1090            1095
Arg Leu Trp Asp Tyr Gly Met Ser Ser Ser Pro His Val Leu Arg
        1100            1105            1110
Asn Arg Ala Gln Ser Gly Ser Val Pro Gln Phe Lys Lys Val Val
        1115            1120            1125
Phe Gln Glu Phe Thr Asp Gly Ser Phe Thr Gln Pro Leu Tyr Arg
        1130            1135            1140
Gly Glu Leu Asn Glu His Leu Gly Leu Leu Gly Pro Tyr Ile Arg
        1145            1150            1155
Ala Glu Val Glu Asp Asn Ile Met Val Thr Phe Arg Asn Gln Ala
        1160            1165            1170
Ser Arg Pro Tyr Ser Phe Tyr Ser Ser Leu Ile Ser Tyr Glu Glu
        1175            1180            1185
Asp Gln Arg Gln Gly Ala Glu Pro Arg Lys Asn Phe Val Lys Pro
        1190            1195            1200
Asn Glu Thr Lys Thr Tyr Phe Trp Lys Val Gln His His Met Ala
        1205            1210            1215
Pro Thr Lys Asp Glu Phe Asp Cys Lys Ala Trp Ala Tyr Phe Ser
        1220            1225            1230
Asp Val Asp Leu Glu Lys Asp Val His Ser Gly Leu Ile Gly Pro
        1235            1240            1245
Leu Leu Val Cys His Thr Asn Thr Leu Asn Pro Ala His Gly Arg
        1250            1255            1260
Gln Val Thr Val Gln Glu Phe Ala Leu Phe Phe Thr Ile Phe Asp
        1265            1270            1275
Glu Thr Lys Ser Trp Tyr Phe Thr Glu Asn Met Glu Arg Asn Cys
        1280            1285            1290
Arg Ala Pro Cys Asn Ile Gln Met Glu Asp Pro Thr Phe Lys Glu
        1295            1300            1305
```

```
Asn Tyr Arg Phe His Ala Ile Asn Gly Tyr Ile Met Asp Thr Leu
    1310                1315                1320

Pro Gly Leu Val Met Ala Gln Asp Gln Arg Ile Arg Trp Tyr Leu
    1325                1330                1335

Leu Ser Met Gly Ser Asn Glu Asn Ile His Ser Ile His Phe Ser
    1340                1345                1350

Gly His Val Phe Thr Val Arg Lys Lys Glu Tyr Lys Met Ala
    1355                1360                1365

Leu Tyr Asn Leu Tyr Pro Gly Val Phe Glu Thr Val Glu Met Leu
    1370                1375                1380

Pro Ser Lys Ala Gly Ile Trp Arg Val Glu Cys Leu Ile Gly Glu
    1385                1390                1395

His Leu His Ala Gly Met Ser Thr Leu Phe Leu Val Tyr Ser Asn
    1400                1405                1410

Lys Cys Gln Thr Pro Leu Gly Met Ala Ser Gly His Ile Arg Asp
    1415                1420                1425

Phe Gln Ile Thr Ala Ser Gly Gln Tyr Gly Gln Trp Ala Pro Lys
    1430                1435                1440

Leu Ala Arg Leu His Tyr Ser Gly Ser Ile Asn Ala Trp Ser Thr
    1445                1450                1455

Lys Glu Pro Phe Ser Trp Ile Lys Val Asp Leu Leu Ala Pro Met
    1460                1465                1470

Ile Ile His Gly Ile Lys Thr Gln Gly Ala Arg Gln Lys Phe Ser
    1475                1480                1485

Ser Leu Tyr Ile Ser Gln Phe Ile Ile Met Tyr Ser Leu Asp Gly
    1490                1495                1500

Lys Lys Trp Gln Thr Tyr Arg Gly Asn Ser Thr Gly Thr Leu Met
    1505                1510                1515

Val Phe Phe Gly Asn Val Asp Ser Ser Gly Ile Lys His Asn Ile
    1520                1525                1530

Phe Asn Pro Pro Ile Ile Ala Arg Tyr Ile Arg Leu His Pro Thr
    1535                1540                1545

His Tyr Ser Ile Arg Ser Thr Leu Arg Met Glu Trp Met Gly Cys
    1550                1555                1560

Asp Leu Asn Ser Cys Ser Met Pro Leu Gly Met Glu Ser Lys Ala
    1565                1570                1575

Ile Ser Asp Ala Gln Ile Thr Ala Ser Ser Tyr Phe Thr Asn Met
    1580                1585                1590

Phe Ala Thr Trp Ser Pro Ser Lys Ala Arg Leu His Leu Gln Gly
    1595                1600                1605

Arg Ser Asn Ala Trp Arg Pro Gln Val Asn Asn Pro Lys Glu Trp
    1610                1615                1620

Leu Gln Val Asp Phe Gln Lys Thr Met Lys Val Thr Gly Val Thr
    1625                1630                1635

Thr Gln Gly Val Lys Ser Leu Leu Thr Ser Met Tyr Val Lys Glu
    1640                1645                1650

Phe Leu Ile Ser Ser Ser Gln Asp Gly His Gln Trp Thr Leu Phe
    1655                1660                1665

Phe Gln Asn Gly Lys Val Lys Val Phe Gln Gly Asn Gln Asp Ser
    1670                1675                1680

Phe Thr Pro Val Val Asn Ser Leu Asp Pro Pro Leu Leu Thr Arg
    1685                1690                1695
```

```
Tyr Leu Arg Ile His Pro Gln Ser Trp Val His Gln Ile Ala Leu
    1700                1705                1710
Arg Met Glu Val Leu Gly Cys Glu Ala Gln Asp Leu Tyr Leu Thr
    1715                1720                1725
Pro Arg Gly Val Arg Leu Gly Gly Ser Gly Gly Gly Ser Gly
    1730                1735                1740
Gly Gly Ser Gly Gly Gly Ser Gln Val Gln Leu Val Gln Ser Gly
    1745                1750                1755
Gly Gly Leu Val Gln Ala Gly Asp Ser Leu Arg Leu Ser Cys Ala
    1760                1765                1770
Ala Ser Gly Arg Thr Phe Ile Arg Tyr Ala Met Ala Trp Phe Arg
    1775                1780                1785
Gln Ala Pro Gly Lys Glu Arg Glu Phe Val Ala Ala Ile Pro Gln
    1790                1795                1800
Ser Gly Gly Arg Ser Tyr Tyr Ala Asp Ser Val Lys Gly Arg Phe
    1805                1810                1815
Thr Ile Ser Arg Asp Asn Ala Lys Asn Thr Val Tyr Leu Gln Met
    1820                1825                1830
Asn Ser Leu Lys Pro Glu Asp Thr Ala Val Tyr Ser Cys Ala Ala
    1835                1840                1845
Thr Ser Thr Tyr Tyr Gly Arg Ser Ala Tyr Ser Ser His Ser Gly
    1850                1855                1860
Gly Tyr Asp Tyr Trp Gly Gln Gly Thr Gln Val Thr Val Ser Ser
    1865                1870                1875
Gly Gly Gly Ser Gly Gly Ser Gly Gly Gly Ser Gly Gly Gly
    1880                1885                1890
Ser Gln Val Gln Leu Val Gln Ser Gly Gly Gly Leu Val Gln Ala
    1895                1900                1905
Gly Asp Ser Leu Arg Leu Ser Cys Ala Ala Ser Gly Arg Thr Phe
    1910                1915                1920
Ile Arg Tyr Ala Met Ala Trp Phe Arg Gln Ala Pro Gly Lys Glu
    1925                1930                1935
Arg Glu Phe Val Ala Ala Ile Pro Gln Ser Gly Gly Arg Ser Tyr
    1940                1945                1950
Tyr Ala Asp Ser Val Lys Gly Arg Phe Thr Ile Ser Arg Asp Asn
    1955                1960                1965
Ala Lys Asn Thr Val Tyr Leu Gln Met Asn Ser Leu Lys Pro Glu
    1970                1975                1980
Asp Thr Ala Val Tyr Ser Cys Ala Ala Thr Ser Thr Tyr Tyr Gly
    1985                1990                1995
Arg Ser Ala Tyr Ser Ser His Ser Gly Gly Tyr Asp Tyr Trp Gly
    2000                2005                2010
Gln Gly Thr Gln Val Thr Val Ser Ser
    2015                2020

<210> SEQ ID NO 21
<211> LENGTH: 2022
<212> TYPE: PRT
<213> ORGANISM: Artificial
<220> FEATURE:
<223> OTHER INFORMATION: Synthetic   FVIII_KB0013bv_Cter-0013bv_Y1680F
      SEQ ID NO: 21

<400> SEQUENCE: 21

Met Gln Ile Glu Leu Ser Thr Cys Phe Phe Leu Cys Leu Leu Arg Phe
1               5                   10                  15
```

```
Cys Phe Ser Ala Thr Arg Arg Tyr Tyr Leu Gly Ala Val Glu Leu Ser
             20                  25                  30

Trp Asp Tyr Met Gln Ser Asp Leu Gly Glu Leu Pro Val Asp Ala Arg
             35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
             115                 120                 125

Glu Gly Ala Glu Tyr Asp Asp Gln Thr Ser Gln Arg Glu Lys Glu Asp
 130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                 165                 170                 175

Tyr Leu Ser His Val Asp Leu Val Lys Asp Leu Asn Ser Gly Leu Ile
             180                 185                 190

Gly Ala Leu Leu Val Cys Arg Glu Gly Ser Leu Ala Lys Glu Lys Thr
             195                 200                 205

Gln Thr Leu His Lys Phe Ile Leu Leu Phe Ala Val Phe Asp Glu Gly
         210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                 245                 250                 255

Val Asn Arg Ser Leu Pro Gly Leu Ile Gly Cys His Arg Lys Ser Val
             260                 265                 270

Tyr Trp His Val Ile Gly Met Gly Thr Thr Pro Glu Val His Ser Ile
         275                 280                 285

Phe Leu Glu Gly His Thr Phe Leu Val Arg Asn His Arg Gln Ala Ser
 290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                 325                 330                 335

Asp Gly Met Glu Ala Tyr Val Lys Val Asp Ser Cys Pro Glu Glu Pro
             340                 345                 350

Gln Leu Arg Met Lys Asn Asn Glu Glu Ala Glu Asp Tyr Asp Asp Asp
         355                 360                 365

Leu Thr Asp Ser Glu Met Asp Val Val Arg Phe Asp Asp Asp Asn Ser
         370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
             405                 410                 415

Leu Val Leu Ala Pro Asp Asp Arg Ser Tyr Lys Ser Gln Tyr Leu Asn
                 420                 425                 430
```

-continued

```
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gly Gly Ser Gln Val
                755                 760                 765
Gln Leu Val Gln Ser Gly Gly Leu Val Gln Ala Gly Asp Ser Leu
    770                 775                 780
Arg Leu Ser Cys Ala Ala Ser Gly Arg Thr Phe Ile Arg Tyr Ala Met
785                 790                 795                 800
Ala Trp Phe Arg Gln Ala Pro Gly Lys Glu Arg Glu Phe Val Ala Ala
                805                 810                 815
Ile Pro Gln Ser Gly Gly Arg Ser Tyr Tyr Ala Asp Ser Val Lys Gly
            820                 825                 830
Arg Phe Thr Ile Ser Arg Asp Asn Ala Lys Asn Thr Val Tyr Leu Gln
        835                 840                 845
Met Asn Ser Leu Lys Pro Glu Asp Thr Ala Val Tyr Ser Cys Ala Ala
```

```
                850                 855                 860
Thr Ser Thr Tyr Tyr Gly Arg Ser Ala Tyr Ser Ser His Ser Gly Gly
865                 870                 875                 880

Tyr Asp Tyr Trp Gly Gln Gly Thr Gln Val Thr Val Ser Ser Gly Gly
                    885                 890                 895

Gly Ser Gly Gly Gly Ser Gly Gly Gly Ser Gly Gly Gly Ser Gln Val
                900                 905                 910

Gln Leu Val Gln Ser Gly Gly Gly Leu Val Gln Ala Gly Asp Ser Leu
            915                 920                 925

Arg Leu Ser Cys Ala Ala Ser Gly Arg Thr Phe Ile Arg Tyr Ala Met
        930                 935                 940

Ala Trp Phe Arg Gln Ala Pro Gly Lys Glu Arg Glu Phe Val Ala Ala
945                 950                 955                 960

Ile Pro Gln Ser Gly Gly Arg Ser Tyr Tyr Ala Asp Ser Val Lys Gly
                965                 970                 975

Arg Phe Thr Ile Ser Arg Asp Asn Ala Lys Asn Thr Val Tyr Leu Gln
            980                 985                 990

Met Asn Ser Leu Lys Pro Glu Asp Thr Ala Val Tyr Ser Cys Ala Ala
        995                 1000                1005

Thr Ser Thr Tyr Tyr Gly Arg Ser Ala Tyr Ser Ser His Ser Gly
    1010                1015                1020

Gly Tyr Asp Tyr Trp Gly Gln Gly Thr Gln Val Thr Val Ser Ser
    1025                1030                1035

Gly Gly Gly Ser Glu Ile Thr Arg Thr Thr Leu Gln Ser Asp Gln
    1040                1045                1050

Glu Glu Ile Asp Tyr Asp Asp Thr Ile Ser Val Glu Met Lys Lys
    1055                1060                1065

Glu Asp Phe Asp Ile Phe Asp Glu Asp Glu Asn Gln Ser Pro Arg
    1070                1075                1080

Ser Phe Gln Lys Lys Thr Arg His Tyr Phe Ile Ala Ala Val Glu
    1085                1090                1095

Arg Leu Trp Asp Tyr Gly Met Ser Ser Ser Pro His Val Leu Arg
    1100                1105                1110

Asn Arg Ala Gln Ser Gly Ser Val Pro Gln Phe Lys Lys Val Val
    1115                1120                1125

Phe Gln Glu Phe Thr Asp Gly Ser Phe Thr Gln Pro Leu Tyr Arg
    1130                1135                1140

Gly Glu Leu Asn Glu His Leu Gly Leu Leu Gly Pro Tyr Ile Arg
    1145                1150                1155

Ala Glu Val Glu Asp Asn Ile Met Val Thr Phe Arg Asn Gln Ala
    1160                1165                1170

Ser Arg Pro Tyr Ser Phe Tyr Ser Ser Leu Ile Ser Tyr Glu Glu
    1175                1180                1185

Asp Gln Arg Gln Gly Ala Glu Pro Arg Lys Asn Phe Val Lys Pro
    1190                1195                1200

Asn Glu Thr Lys Thr Tyr Phe Trp Lys Val Gln His His Met Ala
    1205                1210                1215

Pro Thr Lys Asp Glu Phe Asp Cys Lys Ala Trp Ala Tyr Phe Ser
    1220                1225                1230

Asp Val Asp Leu Glu Lys Asp Val His Ser Gly Leu Ile Gly Pro
    1235                1240                1245

Leu Leu Val Cys His Thr Asn Thr Leu Asn Pro Ala His Gly Arg
    1250                1255                1260
```

```
Gln Val Thr Val Gln Glu Phe Ala Leu Phe Phe Thr Ile Phe Asp
    1265            1270                1275

Glu Thr Lys Ser Trp Tyr Phe Thr Glu Asn Met Glu Arg Asn Cys
    1280            1285                1290

Arg Ala Pro Cys Asn Ile Gln Met Glu Asp Pro Thr Phe Lys Glu
    1295            1300                1305

Asn Tyr Arg Phe His Ala Ile Asn Gly Tyr Ile Met Asp Thr Leu
    1310            1315                1320

Pro Gly Leu Val Met Ala Gln Asp Gln Arg Ile Arg Trp Tyr Leu
    1325            1330                1335

Leu Ser Met Gly Ser Asn Glu Asn Ile His Ser Ile His Phe Ser
    1340            1345                1350

Gly His Val Phe Thr Val Arg Lys Lys Glu Glu Tyr Lys Met Ala
    1355            1360                1365

Leu Tyr Asn Leu Tyr Pro Gly Val Phe Glu Thr Val Glu Met Leu
    1370            1375                1380

Pro Ser Lys Ala Gly Ile Trp Arg Val Glu Cys Leu Ile Gly Glu
    1385            1390                1395

His Leu His Ala Gly Met Ser Thr Leu Phe Leu Val Tyr Ser Asn
    1400            1405                1410

Lys Cys Gln Thr Pro Leu Gly Met Ala Ser Gly His Ile Arg Asp
    1415            1420                1425

Phe Gln Ile Thr Ala Ser Gly Gln Tyr Gly Gln Trp Ala Pro Lys
    1430            1435                1440

Leu Ala Arg Leu His Tyr Ser Gly Ser Ile Asn Ala Trp Ser Thr
    1445            1450                1455

Lys Glu Pro Phe Ser Trp Ile Lys Val Asp Leu Leu Ala Pro Met
    1460            1465                1470

Ile Ile His Gly Ile Lys Thr Gln Gly Ala Arg Gln Lys Phe Ser
    1475            1480                1485

Ser Leu Tyr Ile Ser Gln Phe Ile Ile Met Tyr Ser Leu Asp Gly
    1490            1495                1500

Lys Lys Trp Gln Thr Tyr Arg Gly Asn Ser Thr Gly Thr Leu Met
    1505            1510                1515

Val Phe Phe Gly Asn Val Asp Ser Ser Gly Ile Lys His Asn Ile
    1520            1525                1530

Phe Asn Pro Pro Ile Ile Ala Arg Tyr Ile Arg Leu His Pro Thr
    1535            1540                1545

His Tyr Ser Ile Arg Ser Thr Leu Arg Met Glu Trp Met Gly Cys
    1550            1555                1560

Asp Leu Asn Ser Cys Ser Met Pro Leu Gly Met Glu Ser Lys Ala
    1565            1570                1575

Ile Ser Asp Ala Gln Ile Thr Ala Ser Ser Tyr Phe Thr Asn Met
    1580            1585                1590

Phe Ala Thr Trp Ser Pro Ser Lys Ala Arg Leu His Leu Gln Gly
    1595            1600                1605

Arg Ser Asn Ala Trp Arg Pro Gln Val Asn Asn Pro Lys Glu Trp
    1610            1615                1620

Leu Gln Val Asp Phe Gln Lys Thr Met Lys Val Thr Gly Val Thr
    1625            1630                1635

Thr Gln Gly Val Lys Ser Leu Leu Thr Ser Met Tyr Val Lys Glu
    1640            1645                1650
```

```
Phe Leu Ile Ser Ser Ser Gln Asp Gly His Gln Trp Thr Leu Phe
1655                1660                1665

Phe Gln Asn Gly Lys Val Lys Val Phe Gln Gly Asn Gln Asp Ser
1670                1675                1680

Phe Thr Pro Val Val Asn Ser Leu Asp Pro Pro Leu Leu Thr Arg
1685                1690                1695

Tyr Leu Arg Ile His Pro Gln Ser Trp Val His Gln Ile Ala Leu
1700                1705                1710

Arg Met Glu Val Leu Gly Cys Glu Ala Gln Asp Leu Tyr Leu Thr
1715                1720                1725

Pro Arg Gly Val Arg Leu Gly Gly Gly Ser Gly Gly Gly Ser Gly
1730                1735                1740

Gly Gly Ser Gly Gly Gly Ser Gln Val Gln Leu Val Gln Ser Gly
1745                1750                1755

Gly Gly Leu Val Gln Ala Gly Asp Ser Leu Arg Leu Ser Cys Ala
1760                1765                1770

Ala Ser Gly Arg Thr Phe Ile Arg Tyr Ala Met Ala Trp Phe Arg
1775                1780                1785

Gln Ala Pro Gly Lys Glu Arg Glu Phe Val Ala Ala Ile Pro Gln
1790                1795                1800

Ser Gly Gly Arg Ser Tyr Tyr Ala Asp Ser Val Lys Gly Arg Phe
1805                1810                1815

Thr Ile Ser Arg Asp Asn Ala Lys Asn Thr Val Tyr Leu Gln Met
1820                1825                1830

Asn Ser Leu Lys Pro Glu Asp Thr Ala Val Tyr Ser Cys Ala Ala
1835                1840                1845

Thr Ser Thr Tyr Tyr Gly Arg Ser Ala Tyr Ser Ser His Ser Gly
1850                1855                1860

Gly Tyr Asp Tyr Trp Gly Gln Gly Thr Gln Val Thr Val Ser Ser
1865                1870                1875

Gly Gly Gly Ser Gly Gly Gly Ser Gly Gly Gly Ser Gly Gly Gly
1880                1885                1890

Ser Gln Val Gln Leu Val Gln Ser Gly Gly Gly Leu Val Gln Ala
1895                1900                1905

Gly Asp Ser Leu Arg Leu Ser Cys Ala Ala Ser Gly Arg Thr Phe
1910                1915                1920

Ile Arg Tyr Ala Met Ala Trp Phe Arg Gln Ala Pro Gly Lys Glu
1925                1930                1935

Arg Glu Phe Val Ala Ala Ile Pro Gln Ser Gly Gly Arg Ser Tyr
1940                1945                1950

Tyr Ala Asp Ser Val Lys Gly Arg Phe Thr Ile Ser Arg Asp Asn
1955                1960                1965

Ala Lys Asn Thr Val Tyr Leu Gln Met Asn Ser Leu Lys Pro Glu
1970                1975                1980

Asp Thr Ala Val Tyr Ser Cys Ala Ala Thr Ser Thr Tyr Tyr Gly
1985                1990                1995

Arg Ser Ala Tyr Ser Ser His Ser Gly Gly Tyr Asp Tyr Trp Gly
2000                2005                2010

Gln Gly Thr Gln Val Thr Val Ser Ser
2015                2020
```

<210> SEQ ID NO 22
<211> LENGTH: 2042
<212> TYPE: PRT

<213> ORGANISM: Artificial
<220> FEATURE:
<223> OTHER INFORMATION: Synthetic FVIII_KB0013bv(6GGGS)_Cter-0013bv SEQ
    ID NO: 22

<400> SEQUENCE: 22

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380
```

```
Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
        405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gly Gly Ser Gln Val
            755                 760                 765

Gln Leu Val Gln Ser Gly Gly Leu Val Gln Ala Gly Asp Ser Leu
            770                 775                 780

Arg Leu Ser Cys Ala Ala Ser Gly Arg Thr Phe Ile Arg Tyr Ala Met
785                 790                 795                 800

Ala Trp Phe Arg Gln Ala Pro Gly Lys Glu Arg Glu Phe Val Ala Ala
```

```
                         805                 810                 815
Ile Pro Gln Ser Gly Gly Arg Ser Tyr Tyr Ala Asp Ser Val Lys Gly
                820                 825                 830
Arg Phe Thr Ile Ser Arg Asp Asn Ala Lys Asn Thr Val Tyr Leu Gln
                835                 840                 845
Met Asn Ser Leu Lys Pro Glu Asp Thr Ala Val Tyr Ser Cys Ala Ala
                850                 855                 860
Thr Ser Thr Tyr Tyr Gly Arg Ser Ala Tyr Ser Ser His Ser Gly Gly
865                 870                 875                 880
Tyr Asp Tyr Trp Gly Gln Gly Thr Gln Val Thr Val Ser Ser Gly Gly
                885                 890                 895
Gly Ser Gly Gly Gly Ser Gly Gly Gly Ser Gly Gly Gly Ser Gln Val
                900                 905                 910
Gln Leu Val Gln Ser Gly Gly Gly Leu Val Gln Ala Gly Asp Ser Leu
                915                 920                 925
Arg Leu Ser Cys Ala Ala Ser Gly Arg Thr Phe Ile Arg Tyr Ala Met
                930                 935                 940
Ala Trp Phe Arg Gln Ala Pro Gly Lys Glu Arg Glu Phe Val Ala Ala
945                 950                 955                 960
Ile Pro Gln Ser Gly Gly Arg Ser Tyr Tyr Ala Asp Ser Val Lys Gly
                965                 970                 975
Arg Phe Thr Ile Ser Arg Asp Asn Ala Lys Asn Thr Val Tyr Leu Gln
                980                 985                 990
Met Asn Ser Leu Lys Pro Glu Asp  Thr Ala Val Tyr Ser  Cys Ala Ala
                995                1000                1005
Thr Ser  Thr Tyr Tyr Gly Arg  Ser Ala Tyr Ser Ser  His Ser Gly
1010                1015                1020
Gly Tyr  Asp Tyr Trp Gly Gln  Gly Thr Gln Val Thr  Val Ser Ser
1025                1030                1035
Gly Gly  Gly Ser Gly Gly Gly  Ser Gly Gly Gly Ser  Gly Gly Gly
1040                1045                1050
Ser Gly  Gly Gly Ser Gly Gly  Gly Ser Glu Ile Thr  Arg Thr Thr
1055                1060                1065
Leu Gln  Ser Asp Gln Glu Glu  Ile Asp Tyr Asp Asp  Thr Ile Ser
1070                1075                1080
Val Glu  Met Lys Lys Glu Asp  Phe Asp Ile Tyr Asp  Glu Asp Glu
1085                1090                1095
Asn Gln  Ser Pro Arg Ser Phe  Gln Lys Lys Thr Arg  His Tyr Phe
1100                1105                1110
Ile Ala  Ala Val Glu Arg Leu  Trp Asp Tyr Gly Met  Ser Ser Ser
1115                1120                1125
Pro His  Val Leu Arg Asn Arg  Ala Gln Ser Gly Ser  Val Pro Gln
1130                1135                1140
Phe Lys  Lys Val Val Phe Gln  Glu Phe Thr Asp Gly  Ser Phe Thr
1145                1150                1155
Gln Pro  Leu Tyr Arg Gly Glu  Leu Asn Glu His Leu  Gly Leu Leu
1160                1165                1170
Gly Pro  Tyr Ile Arg Ala Glu  Val Glu Asp Asn Ile  Met Val Thr
1175                1180                1185
Phe Arg  Asn Gln Ala Ser Arg  Pro Tyr Ser Phe Tyr  Ser Ser Leu
1190                1195                1200
Ile Ser  Tyr Glu Glu Asp Gln  Arg Gln Gly Ala Glu  Pro Arg Lys
1205                1210                1215
```

```
Asn Phe Val Lys Pro Asn Glu Thr Lys Thr Tyr Phe Trp Lys Val
    1220             1225                 1230

Gln His His Met Ala Pro Thr Lys Asp Glu Phe Asp Cys Lys Ala
    1235             1240                 1245

Trp Ala Tyr Phe Ser Asp Val Asp Leu Gly Lys Asp Val His Ser
    1250             1255                 1260

Gly Leu Ile Gly Pro Leu Leu Val Cys His Thr Asn Thr Leu Asn
    1265             1270                 1275

Pro Ala His Gly Arg Gln Val Thr Val Gln Glu Phe Ala Leu Phe
    1280             1285                 1290

Phe Thr Ile Phe Asp Glu Thr Lys Ser Trp Tyr Phe Thr Glu Asn
    1295             1300                 1305

Met Glu Arg Asn Cys Arg Ala Pro Cys Asn Ile Gln Met Glu Asp
    1310             1315                 1320

Pro Thr Phe Lys Glu Asn Tyr Arg Phe His Ala Ile Asn Gly Tyr
    1325             1330                 1335

Ile Met Asp Thr Leu Pro Gly Leu Val Met Ala Gln Asp Gln Arg
    1340             1345                 1350

Ile Arg Trp Tyr Leu Leu Ser Met Gly Ser Asn Glu Asn Ile His
    1355             1360                 1365

Ser Ile His Phe Ser Gly His Val Phe Thr Val Arg Lys Lys Glu
    1370             1375                 1380

Glu Tyr Lys Met Ala Leu Tyr Asn Leu Tyr Pro Gly Val Phe Glu
    1385             1390                 1395

Thr Val Glu Met Leu Pro Ser Lys Ala Gly Ile Trp Arg Val Glu
    1400             1405                 1410

Cys Leu Ile Gly Glu His Leu His Ala Gly Met Ser Thr Leu Phe
    1415             1420                 1425

Leu Val Tyr Ser Asn Lys Cys Gln Thr Pro Leu Gly Met Ala Ser
    1430             1435                 1440

Gly His Ile Arg Asp Phe Gln Ile Thr Ala Ser Gly Gln Tyr Gly
    1445             1450                 1455

Gln Trp Ala Pro Lys Leu Ala Arg Leu His Tyr Ser Gly Ser Ile
    1460             1465                 1470

Asn Ala Trp Ser Thr Lys Glu Pro Phe Ser Trp Ile Lys Val Asp
    1475             1480                 1485

Leu Leu Ala Pro Met Ile Ile His Gly Ile Lys Thr Gln Gly Ala
    1490             1495                 1500

Arg Gln Lys Phe Ser Ser Leu Tyr Ile Ser Gln Phe Ile Ile Met
    1505             1510                 1515

Tyr Ser Leu Asp Gly Lys Lys Trp Gln Thr Tyr Arg Gly Asn Ser
    1520             1525                 1530

Thr Gly Thr Leu Met Val Phe Phe Gly Asn Val Asp Ser Ser Gly
    1535             1540                 1545

Ile Lys His Asn Ile Phe Asn Pro Pro Ile Ile Ala Arg Tyr Ile
    1550             1555                 1560

Arg Leu His Pro Thr His Tyr Ser Ile Arg Ser Thr Leu Arg Met
    1565             1570                 1575

Glu Trp Met Gly Cys Asp Leu Asn Ser Cys Ser Met Pro Leu Gly
    1580             1585                 1590

Met Glu Ser Lys Ala Ile Ser Asp Ala Gln Ile Thr Ala Ser Ser
    1595             1600                 1605
```

```
Tyr Phe Thr Asn Met Phe Ala Thr Trp Ser Pro Ser Lys Ala Arg
1610                1615                1620

Leu His Leu Gln Gly Arg Ser Asn Ala Trp Arg Pro Gln Val Asn
1625                1630                1635

Asn Pro Lys Glu Trp Leu Gln Val Asp Phe Gln Lys Thr Met Lys
1640                1645                1650

Val Thr Gly Val Thr Thr Gln Gly Val Lys Ser Leu Leu Thr Ser
1655                1660                1665

Met Tyr Val Lys Glu Phe Leu Ile Ser Ser Ser Gln Asp Gly His
1670                1675                1680

Gln Trp Thr Leu Phe Phe Gln Asn Gly Lys Val Lys Val Phe Gln
1685                1690                1695

Gly Asn Gln Asp Ser Phe Thr Pro Val Val Asn Ser Leu Asp Pro
1700                1705                1710

Pro Leu Leu Thr Arg Tyr Leu Arg Ile His Pro Gln Ser Trp Val
1715                1720                1725

His Gln Ile Ala Leu Arg Met Glu Val Leu Gly Cys Glu Ala Gln
1730                1735                1740

Asp Leu Tyr Leu Thr Pro Arg Gly Val Arg Leu Gly Gly Gly Ser
1745                1750                1755

Gly Gly Gly Ser Gly Gly Gly Ser Gly Gly Gly Ser Gln Val Gln
1760                1765                1770

Leu Val Gln Ser Gly Gly Gly Leu Val Gln Ala Gly Asp Ser Leu
1775                1780                1785

Arg Leu Ser Cys Ala Ala Ser Gly Arg Thr Phe Ile Arg Tyr Ala
1790                1795                1800

Met Ala Trp Phe Arg Gln Ala Pro Gly Lys Glu Arg Glu Phe Val
1805                1810                1815

Ala Ala Ile Pro Gln Ser Gly Gly Arg Ser Tyr Tyr Ala Asp Ser
1820                1825                1830

Val Lys Gly Arg Phe Thr Ile Ser Arg Asp Asn Ala Lys Asn Thr
1835                1840                1845

Val Tyr Leu Gln Met Asn Ser Leu Lys Pro Glu Asp Thr Ala Val
1850                1855                1860

Tyr Ser Cys Ala Ala Thr Ser Thr Tyr Tyr Gly Arg Ser Ala Tyr
1865                1870                1875

Ser Ser His Ser Gly Gly Tyr Asp Tyr Trp Gly Gln Gly Thr Gln
1880                1885                1890

Val Thr Val Ser Ser Gly Gly Gly Ser Gly Gly Gly Ser Gly Gly
1895                1900                1905

Gly Ser Gly Gly Gly Ser Gln Val Gln Leu Val Gln Ser Gly Gly
1910                1915                1920

Gly Leu Val Gln Ala Gly Asp Ser Leu Arg Leu Ser Cys Ala Ala
1925                1930                1935

Ser Gly Arg Thr Phe Ile Arg Tyr Ala Met Ala Trp Phe Arg Gln
1940                1945                1950

Ala Pro Gly Lys Glu Arg Glu Phe Val Ala Ala Ile Pro Gln Ser
1955                1960                1965

Gly Gly Arg Ser Tyr Tyr Ala Asp Ser Val Lys Gly Arg Phe Thr
1970                1975                1980

Ile Ser Arg Asp Asn Ala Lys Asn Thr Val Tyr Leu Gln Met Asn
1985                1990                1995

Ser Leu Lys Pro Glu Asp Thr Ala Val Tyr Ser Cys Ala Ala Thr
```

```
                    2000                2005                2010

Ser Thr Tyr Tyr Gly Arg Ser Ala Tyr Ser Ser His Ser Gly Gly
        2015                2020                2025

Tyr Asp Tyr Trp Gly Gln Gly Thr Gln Val Thr Val Ser Ser
        2030                2035                2040

<210> SEQ ID NO 23
<211> LENGTH: 2042
<212> TYPE: PRT
<213> ORGANISM: Artificial
<220> FEATURE:
<223> OTHER INFORMATION: Synthetic
      FVIII_KB0013bv(6GGGS)_Cter-0013bv_Y1680F SEQ ID NO: 23

<400> SEQUENCE: 23

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320
```

-continued

```
Asp Leu Gly Gln Phe Leu Leu Phe Cys His Ile Ser Ser His Gln His
            325                 330                 335

Asp Gly Met Glu Ala Tyr Val Lys Val Asp Ser Cys Pro Glu Pro
        340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
```

```
                    740                 745                 750
Asn Asn Ala Ile Glu Pro Arg Ser Phe Ser Gly Gly Gly Ser Gln Val
                755                 760                 765
Gln Leu Val Gln Ser Gly Gly Gly Leu Val Gln Ala Gly Asp Ser Leu
                770                 775                 780
Arg Leu Ser Cys Ala Ala Ser Gly Arg Thr Phe Ile Arg Tyr Ala Met
785                 790                 795                 800
Ala Trp Phe Arg Gln Ala Pro Gly Lys Glu Arg Glu Phe Val Ala Ala
                805                 810                 815
Ile Pro Gln Ser Gly Gly Arg Ser Tyr Tyr Ala Asp Ser Val Lys Gly
                820                 825                 830
Arg Phe Thr Ile Ser Arg Asp Asn Ala Lys Asn Thr Val Tyr Leu Gln
                835                 840                 845
Met Asn Ser Leu Lys Pro Glu Asp Thr Ala Val Tyr Ser Cys Ala Ala
                850                 855                 860
Thr Ser Thr Tyr Tyr Gly Arg Ser Ala Tyr Ser Ser His Ser Gly Gly
865                 870                 875                 880
Tyr Asp Tyr Trp Gly Gln Gly Thr Gln Val Thr Val Ser Ser Gly Gly
                885                 890                 895
Gly Ser Gly Gly Gly Ser Gly Gly Ser Gly Gly Gly Ser Gln Val
                900                 905                 910
Gln Leu Val Gln Ser Gly Gly Gly Leu Val Gln Ala Gly Asp Ser Leu
                915                 920                 925
Arg Leu Ser Cys Ala Ala Ser Gly Arg Thr Phe Ile Arg Tyr Ala Met
                930                 935                 940
Ala Trp Phe Arg Gln Ala Pro Gly Lys Glu Arg Glu Phe Val Ala Ala
945                 950                 955                 960
Ile Pro Gln Ser Gly Gly Arg Ser Tyr Tyr Ala Asp Ser Val Lys Gly
                965                 970                 975
Arg Phe Thr Ile Ser Arg Asp Asn Ala Lys Asn Thr Val Tyr Leu Gln
                980                 985                 990
Met Asn Ser Leu Lys Pro Glu Asp Thr Ala Val Tyr Ser Cys Ala Ala
                995                1000                1005
Thr Ser Thr Tyr Tyr Gly Arg Ser Ala Tyr Ser Ser His Ser Gly
                1010                1015                1020
Gly Tyr Asp Tyr Trp Gly Gln Gly Thr Gln Val Thr Val Ser Ser
                1025                1030                1035
Gly Gly Gly Ser Gly Gly Gly Ser Gly Gly Gly Ser Gly Gly Gly
                1040                1045                1050
Ser Gly Gly Gly Ser Gly Gly Gly Ser Glu Ile Thr Arg Thr Thr
                1055                1060                1065
Leu Gln Ser Asp Gln Glu Glu Ile Asp Tyr Asp Asp Thr Ile Ser
                1070                1075                1080
Val Glu Met Lys Lys Glu Asp Phe Asp Ile Phe Asp Glu Asp Glu
                1085                1090                1095
Asn Gln Ser Pro Arg Ser Phe Gln Lys Lys Thr Arg His Tyr Phe
                1100                1105                1110
Ile Ala Ala Val Glu Arg Leu Trp Asp Tyr Gly Met Ser Ser Ser
                1115                1120                1125
Pro His Val Leu Arg Asn Arg Ala Gln Ser Gly Ser Val Pro Gln
                1130                1135                1140
Phe Lys Lys Val Val Phe Gln Glu Phe Thr Asp Gly Ser Phe Thr
                1145                1150                1155
```

```
Gln Pro Leu Tyr Arg Gly Glu Leu Asn Glu His Leu Gly Leu Leu
    1160            1165                1170

Gly Pro Tyr Ile Arg Ala Glu Val Glu Asp Asn Ile Met Val Thr
    1175            1180                1185

Phe Arg Asn Gln Ala Ser Arg Pro Tyr Ser Phe Tyr Ser Ser Leu
    1190            1195                1200

Ile Ser Tyr Glu Glu Asp Gln Arg Gln Gly Ala Glu Pro Arg Lys
    1205            1210                1215

Asn Phe Val Lys Pro Asn Glu Thr Lys Thr Tyr Phe Trp Lys Val
    1220            1225                1230

Gln His His Met Ala Pro Thr Lys Asp Glu Phe Asp Cys Lys Ala
    1235            1240                1245

Trp Ala Tyr Phe Ser Asp Val Asp Leu Glu Lys Asp Val His Ser
    1250            1255                1260

Gly Leu Ile Gly Pro Leu Leu Val Cys His Thr Asn Thr Leu Asn
    1265            1270                1275

Pro Ala His Gly Arg Gln Val Thr Val Gln Glu Phe Ala Leu Phe
    1280            1285                1290

Phe Thr Ile Phe Asp Glu Thr Lys Ser Trp Tyr Phe Thr Glu Asn
    1295            1300                1305

Met Glu Arg Asn Cys Arg Ala Pro Cys Asn Ile Gln Met Glu Asp
    1310            1315                1320

Pro Thr Phe Lys Glu Asn Tyr Arg Phe His Ala Ile Asn Gly Tyr
    1325            1330                1335

Ile Met Asp Thr Leu Pro Gly Leu Val Met Ala Gln Asp Gln Arg
    1340            1345                1350

Ile Arg Trp Tyr Leu Leu Ser Met Gly Ser Asn Glu Asn Ile His
    1355            1360                1365

Ser Ile His Phe Ser Gly His Val Phe Thr Val Arg Lys Lys Glu
    1370            1375                1380

Glu Tyr Lys Met Ala Leu Tyr Asn Leu Tyr Pro Gly Val Phe Glu
    1385            1390                1395

Thr Val Glu Met Leu Pro Ser Lys Ala Gly Ile Trp Arg Val Glu
    1400            1405                1410

Cys Leu Ile Gly Glu His Leu His Ala Gly Met Ser Thr Leu Phe
    1415            1420                1425

Leu Val Tyr Ser Asn Lys Cys Gln Thr Pro Leu Gly Met Ala Ser
    1430            1435                1440

Gly His Ile Arg Asp Phe Gln Ile Thr Ala Ser Gly Gln Tyr Gly
    1445            1450                1455

Gln Trp Ala Pro Lys Leu Ala Arg Leu His Tyr Ser Gly Ser Ile
    1460            1465                1470

Asn Ala Trp Ser Thr Lys Glu Pro Phe Ser Trp Ile Lys Val Asp
    1475            1480                1485

Leu Leu Ala Pro Met Ile Ile His Gly Ile Lys Thr Gln Gly Ala
    1490            1495                1500

Arg Gln Lys Phe Ser Ser Leu Tyr Ile Ser Gln Phe Ile Ile Met
    1505            1510                1515

Tyr Ser Leu Asp Gly Lys Lys Trp Gln Thr Tyr Arg Gly Asn Ser
    1520            1525                1530

Thr Gly Thr Leu Met Val Phe Phe Gly Asn Val Asp Ser Ser Gly
    1535            1540                1545
```

```
Ile Lys His Asn Ile Phe Asn Pro Pro Ile Ile Ala Arg Tyr Ile
    1550            1555                1560

Arg Leu His Pro Thr His Tyr Ser Ile Arg Ser Thr Leu Arg Met
    1565            1570                1575

Glu Trp Met Gly Cys Asp Leu Asn Ser Cys Ser Met Pro Leu Gly
    1580            1585                1590

Met Glu Ser Lys Ala Ile Ser Asp Ala Gln Ile Thr Ala Ser Ser
    1595            1600                1605

Tyr Phe Thr Asn Met Phe Ala Thr Trp Ser Pro Ser Lys Ala Arg
    1610            1615                1620

Leu His Leu Gln Gly Arg Ser Asn Ala Trp Arg Pro Gln Val Asn
    1625            1630                1635

Asn Pro Lys Glu Trp Leu Gln Val Asp Phe Gln Lys Thr Met Lys
    1640            1645                1650

Val Thr Gly Val Thr Thr Gln Gly Val Lys Ser Leu Leu Thr Ser
    1655            1660                1665

Met Tyr Val Lys Glu Phe Leu Ile Ser Ser Ser Gln Asp Gly His
    1670            1675                1680

Gln Trp Thr Leu Phe Phe Gln Asn Gly Lys Val Lys Val Phe Gln
    1685            1690                1695

Gly Asn Gln Asp Ser Phe Thr Pro Val Val Asn Ser Leu Asp Pro
    1700            1705                1710

Pro Leu Leu Thr Arg Tyr Leu Arg Ile His Pro Gln Ser Trp Val
    1715            1720                1725

His Gln Ile Ala Leu Arg Met Glu Val Leu Gly Cys Glu Ala Gln
    1730            1735                1740

Asp Leu Tyr Leu Thr Pro Arg Gly Val Arg Leu Gly Gly Gly Ser
    1745            1750                1755

Gly Gly Gly Ser Gly Gly Gly Ser Gly Gly Gly Ser Gln Val Gln
    1760            1765                1770

Leu Val Gln Ser Gly Gly Gly Leu Val Gln Ala Gly Asp Ser Leu
    1775            1780                1785

Arg Leu Ser Cys Ala Ala Ser Gly Arg Thr Phe Ile Arg Tyr Ala
    1790            1795                1800

Met Ala Trp Phe Arg Gln Ala Pro Gly Lys Glu Arg Glu Phe Val
    1805            1810                1815

Ala Ala Ile Pro Gln Ser Gly Gly Arg Ser Tyr Tyr Ala Asp Ser
    1820            1825                1830

Val Lys Gly Arg Phe Thr Ile Ser Arg Asp Asn Ala Lys Asn Thr
    1835            1840                1845

Val Tyr Leu Gln Met Asn Ser Leu Lys Pro Glu Asp Thr Ala Val
    1850            1855                1860

Tyr Ser Cys Ala Ala Thr Ser Thr Tyr Tyr Gly Arg Ser Ala Tyr
    1865            1870                1875

Ser Ser His Ser Gly Gly Tyr Asp Tyr Trp Gln Gly Thr Gln
    1880            1885                1890

Val Thr Val Ser Ser Gly Gly Gly Ser Gly Gly Ser Gly Gly
    1895            1900                1905

Gly Ser Gly Gly Gly Ser Gln Val Gln Leu Val Gln Ser Gly Gly
    1910            1915                1920

Gly Leu Val Gln Ala Gly Asp Ser Leu Arg Leu Ser Cys Ala Ala
    1925            1930                1935
```

-continued

```
Ser Gly Arg Thr Phe Ile Arg Tyr Ala Met Ala Trp Phe Arg Gln
    1940            1945            1950

Ala Pro Gly Lys Glu Arg Glu Phe Val Ala Ala Ile Pro Gln Ser
    1955            1960            1965

Gly Gly Arg Ser Tyr Tyr Ala Asp Ser Val Lys Gly Arg Phe Thr
    1970            1975            1980

Ile Ser Arg Asp Asn Ala Lys Asn Thr Val Tyr Leu Gln Met Asn
    1985            1990            1995

Ser Leu Lys Pro Glu Asp Thr Ala Val Tyr Ser Cys Ala Ala Thr
    2000            2005            2010

Ser Thr Tyr Tyr Gly Arg Ser Ala Tyr Ser Ser His Ser Gly Gly
    2015            2020            2025

Tyr Asp Tyr Trp Gly Gln Gly Thr Gln Val Thr Val Ser Ser
    2030            2035            2040
```